(12) United States Patent
Zhong et al.

(10) Patent No.: US 11,331,019 B2
(45) Date of Patent: May 17, 2022

(54) NANOPARTICLE SENSOR HAVING A NANOFIBROUS MEMBRANE SCAFFOLD

(71) Applicant: The Research Foundation for The State University of New York, Binghamton, NY (US)

(72) Inventors: Chuan-Jian Zhong, Endwell, NY (US); Mark D. Poliks, Vestal, NY (US); Benjamin S. Hsiao, Setauket, NY (US); Ning Kang, Vestal, NY (US); Shan Yan, Vestal, NY (US); Jing Li, Vestal, NY (US); Shiyao Shan, Vestal, NY (US); Jin Luo, Vestal, NY (US)

(73) Assignee: The Research Foundation for The State University of New York, Binghamton, NY (US)

( * ) Notice: Subject to any disclaimer, the term of this patent is extended or adjusted under 35 U.S.C. 154(b) by 797 days.

(21) Appl. No.: 16/057,314

(22) Filed: Aug. 7, 2018

(65) Prior Publication Data
US 2019/0038190 A1 Feb. 7, 2019

Related U.S. Application Data

(60) Provisional application No. 62/542,067, filed on Aug. 7, 2017.

(51) Int. Cl.
*A61B 5/1477* (2006.01)
*A61B 5/00* (2006.01)
(Continued)

(52) U.S. Cl.
CPC ............ *A61B 5/1477* (2013.01); *A61B 5/082* (2013.01); *A61B 5/14517* (2013.01);
(Continued)

(58) Field of Classification Search
CPC .................. A61B 5/14517; A61B 5/15407
See application file for complete search history.

(56) References Cited

U.S. PATENT DOCUMENTS

| 4,636,767 A | 1/1987 | Barger et al. |
| 4,759,210 A | 7/1988 | Wohltjen |

(Continued)

*Primary Examiner* — Puya Agahi
(74) *Attorney, Agent, or Firm* — Hoffberg & Associates; Steven M. Hoffberg

(57) ABSTRACT

Nanoparticle-fibrous membrane composites are provided as tunable interfacial scaffolds for flexible chemical sensors and biosensors by assembling gold nanoparticles (Au NPs) in a fibrous membrane. The gold nanoparticles are functionalized with organic, polymeric and/or biological molecules. The fibrous membranes may include different filter papers, with one example featuring a multilayered fibrous membrane consisting of a cellulose nanofiber (CN) top layer, an electrospun polyacrylonitrile (PAN) nanofibrous midlayer (or alternate material), and a nonwoven polyethylene terephthalate (PET) fibrous support layer, with the nanoparticles provided on the fibrous membranes through interparticle molecular/polymeric linkages and nanoparticle-nanofibrous interactions. Molecular linkers may be employed to tune hydrogen bonding and electrostatic and/or hydrophobic/hydrophilic interactions to provide sensor specificity to gases or liquids. The sensors act as chemiresistor-type sensors. A preferred implementation is a sweat sensor.

20 Claims, 29 Drawing Sheets

(51) Int. Cl.
*A61B 5/145* (2006.01)
*B33Y 80/00* (2015.01)
*A61B 5/08* (2006.01)

(52) U.S. Cl.
CPC ............ *A61B 5/4266* (2013.01); *B33Y 80/00* (2014.12); *A61B 5/145* (2013.01); *A61B 2560/0412* (2013.01); *A61B 2562/0285* (2013.01); *A61B 2562/0295* (2013.01); *A61B 2562/12* (2013.01)

(56) References Cited

U.S. PATENT DOCUMENTS

| | | |
|---|---|---|
| 4,847,594 A | 7/1989 | Stetter |
| 4,886,625 A | 12/1989 | Albarella et al. |
| 4,900,817 A | 2/1990 | Batzel et al. |
| 4,992,244 A | 2/1991 | Grate |
| 5,045,285 A | 9/1991 | Kolesar, Jr. |
| 5,071,770 A | 12/1991 | Kolesar, Jr. |
| 5,089,294 A | 2/1992 | Ratcliffe |
| 5,210,217 A | 5/1993 | Albarella et al. |
| 5,224,972 A | 7/1993 | Frye et al. |
| 5,238,729 A | 8/1993 | Debe |
| 5,279,795 A | 1/1994 | Hughes et al. |
| 5,280,183 A | 1/1994 | Batzel et al. |
| 5,302,935 A | 4/1994 | Chatterjee |
| 5,321,146 A | 6/1994 | Royster, Jr. et al. |
| 5,387,462 A | 2/1995 | Debe |
| 5,433,971 A | 7/1995 | Royster, Jr. et al. |
| 5,469,369 A | 11/1995 | Rose-Pehrsson et al. |
| 5,498,323 A | 3/1996 | Lewenstam et al. |
| 5,512,882 A | 4/1996 | Stetter et al. |
| 5,536,473 A | 7/1996 | Monkman et al. |
| 5,550,062 A | 8/1996 | Wohltjen et al. |
| 5,571,401 A | 11/1996 | Lewis et al. |
| 5,589,396 A | 12/1996 | Frye et al. |
| 5,629,435 A | 5/1997 | Royster, Jr. et al. |
| 5,674,752 A | 10/1997 | Buckley et al. |
| 5,698,083 A | 12/1997 | Glass |
| 5,698,089 A | 12/1997 | Lewis et al. |
| 5,729,203 A | 3/1998 | Oka et al. |
| 5,788,833 A | 8/1998 | Lewis et al. |
| 5,858,186 A | 1/1999 | Glass |
| 5,891,398 A | 4/1999 | Lewis et al. |
| 5,911,872 A | 6/1999 | Lewis et al. |
| 5,951,846 A | 9/1999 | Lewis et al. |
| 5,959,191 A | 9/1999 | Lewis et al. |
| 5,976,466 A | 11/1999 | Ratner et al. |
| 6,004,494 A | 12/1999 | Debe |
| 6,010,616 A | 1/2000 | Lewis et al. |
| 6,013,229 A | 1/2000 | Lewis et al. |
| 6,015,869 A | 1/2000 | Grate et al. |
| 6,017,440 A | 1/2000 | Lewis et al. |
| 6,085,576 A | 7/2000 | Sunshine et al. |
| 6,093,308 A | 7/2000 | Lewis et al. |
| 6,170,318 B1 | 1/2001 | Lewis |
| 6,198,953 B1 | 3/2001 | Webster et al. |
| 6,221,673 B1 | 4/2001 | Snow et al. |
| 6,238,085 B1 | 5/2001 | Higashi et al. |
| 6,244,096 B1 | 6/2001 | Lewis et al. |
| 6,290,911 B1 | 9/2001 | Lewis et al. |
| 6,319,724 B1 | 11/2001 | Lewis et al. |
| 6,331,244 B1 | 12/2001 | Lewis et al. |
| 6,350,369 B1 | 2/2002 | Lewis et al. |
| 6,359,444 B1 | 3/2002 | Grimes |
| 6,361,944 B1 | 3/2002 | Mirkin et al. |
| 6,387,329 B1 | 5/2002 | Lewis et al. |
| 6,397,661 B1 | 6/2002 | Grimes et al. |
| 6,408,250 B1 | 6/2002 | Grate et al. |
| 6,417,340 B1 | 7/2002 | Mirkin et al. |
| 6,418,783 B2 | 7/2002 | Sunshine et al. |
| 6,421,588 B1 | 7/2002 | Janata |
| 6,422,061 B1 | 7/2002 | Sunshine et al. |
| 6,458,327 B1 | 10/2002 | Vossmeyer |
| 6,495,324 B1 | 12/2002 | Mirkin et al. |
| 6,506,564 B1 | 1/2003 | Mirkin et al. |
| 6,541,617 B1 | 4/2003 | Bamdad et al. |
| 6,582,921 B2 | 6/2003 | Mirkin et al. |
| 6,607,484 B2 | 8/2003 | Suzuki et al. |
| 6,610,491 B2 | 8/2003 | Mirkin et al. |
| 6,613,660 B2 | 9/2003 | Kahlert et al. |
| 6,645,721 B2 | 11/2003 | Mirkin et al. |
| 6,673,548 B2 | 1/2004 | Mirkin et al. |
| 6,677,122 B2 | 1/2004 | Mirkin et al. |
| 6,682,895 B2 | 1/2004 | Mirkin et al. |
| 6,709,825 B2 | 3/2004 | Mirkin et al. |
| 6,720,147 B2 | 4/2004 | Mirkin et al. |
| 6,720,411 B2 | 4/2004 | Mirkin et al. |
| 6,730,269 B2 | 5/2004 | Mirkin et al. |
| 6,740,491 B2 | 5/2004 | Mirkin et al. |
| 6,750,016 B2 | 6/2004 | Mirkin et al. |
| 6,759,199 B2 | 7/2004 | Mirkin et al. |
| 6,767,702 B2 | 7/2004 | Mirkin et al. |
| 6,773,884 B2 | 8/2004 | Mirkin et al. |
| 6,777,186 B2 | 8/2004 | Mirkin et al. |
| 6,812,334 B1 | 11/2004 | Mirkin et al. |
| 6,818,753 B2 | 11/2004 | Mirkin et al. |
| 6,819,247 B2 | 11/2004 | Birnbach et al. |
| 6,828,432 B2 | 12/2004 | Mirkin et al. |
| 6,861,221 B2 | 3/2005 | Mirkin et al. |
| 6,878,814 B2 | 4/2005 | Mirkin et al. |
| 6,882,940 B2 | 4/2005 | Potts et al. |
| 6,893,396 B2 | 5/2005 | Schulze et al. |
| 6,902,895 B2 | 6/2005 | Mirkin et al. |
| 6,903,207 B2 | 6/2005 | Mirkin et al. |
| 6,942,615 B2 | 9/2005 | Suzuki et al. |
| 6,962,786 B2 | 11/2005 | Mirkin et al. |
| 6,969,761 B2 | 11/2005 | Mirkin et al. |
| 6,984,491 B2 | 1/2006 | Mirkin et al. |
| 6,985,078 B2 | 1/2006 | Suzuki et al. |
| 6,986,989 B2 | 1/2006 | Mirkin et al. |
| 7,029,852 B2 | 4/2006 | Liebholz et al. |
| 7,034,677 B2 | 4/2006 | Steinthal et al. |
| 7,044,908 B1 | 5/2006 | Montalbo et al. |
| 7,052,854 B2 | 5/2006 | Melker et al. |
| 7,098,320 B1 | 8/2006 | Mirkin et al. |
| 7,109,933 B2 | 9/2006 | Ito et al. |
| 7,122,152 B2 | 10/2006 | Lewis et al. |
| 7,128,716 B2 | 10/2006 | Higurashi et al. |
| 7,136,716 B2 | 11/2006 | Hsiung et al. |
| 7,138,090 B2 | 11/2006 | Blok |
| 7,144,553 B2 | 12/2006 | Lewis et al. |
| 7,144,949 B2 | 12/2006 | Kaner et al. |
| 7,168,294 B2 | 1/2007 | Porter et al. |
| 7,169,556 B2 | 1/2007 | Park et al. |
| 7,171,312 B2 | 1/2007 | Steinthal et al. |
| 7,171,331 B2 | 1/2007 | Vock et al. |
| 7,174,277 B2 | 2/2007 | Vock et al. |
| 7,175,885 B2 | 2/2007 | Lewis et al. |
| 7,179,421 B1 | 2/2007 | Ho |
| 7,187,960 B2 | 3/2007 | Abreu |
| 7,189,353 B2 | 3/2007 | Lewis et al. |
| 7,189,360 B1 | 3/2007 | Ho |
| 7,189,867 B1 | 3/2007 | Wynne et al. |
| 7,191,805 B2 | 3/2007 | Cohen et al. |
| 7,195,780 B2 | 3/2007 | Dennis et al. |
| 7,201,035 B2 | 4/2007 | Sunshine |
| 7,208,587 B2 | 4/2007 | Mirkin et al. |
| 7,211,439 B2 | 5/2007 | Vossmeyer et al. |
| 7,211,637 B2 | 5/2007 | Blok |
| 7,226,530 B2 | 6/2007 | Weiller et al. |
| 7,229,593 B1 | 6/2007 | Ho |
| 7,233,781 B2 | 6/2007 | Hunter et al. |
| 7,242,310 B2 | 7/2007 | Hotton et al. |
| 7,250,499 B2 | 7/2007 | Mirkin et al. |
| 7,253,004 B2 | 8/2007 | Vossmeyer et al. |
| 7,259,252 B2 | 8/2007 | Mirkin et al. |
| 7,265,560 B2 | 9/2007 | West et al. |
| 7,267,948 B2 | 9/2007 | Vo-Dinh |
| 7,272,530 B2 | 9/2007 | Hsiung et al. |
| 7,285,090 B2 | 10/2007 | Stivoric et al. |
| 7,288,415 B2 | 10/2007 | Huang |
| 7,313,447 B2 | 12/2007 | Hsiung et al. |
| 7,340,941 B1 | 3/2008 | Fruhberger et al. |

(56) References Cited

U.S. PATENT DOCUMENTS

| | | |
|---|---|---|
| 7,342,479 B2 | 3/2008 | Glatkowski et al. |
| 7,347,974 B1 | 3/2008 | Snow et al. |
| 7,353,136 B2 | 4/2008 | Vock et al. |
| 7,353,137 B2 | 4/2008 | Vock et al. |
| 7,356,420 B2 | 4/2008 | Vilanova et al. |
| 7,359,802 B1 | 4/2008 | Lewis et al. |
| 7,383,072 B2 | 6/2008 | Edmonson et al. |
| 7,387,010 B2 | 6/2008 | Sunshine |
| 7,395,693 B2 | 7/2008 | Porter et al. |
| 7,397,072 B2 | 7/2008 | Dodabalapur et al. |
| 7,404,928 B2 | 7/2008 | Foos et al. |
| 7,407,484 B2 | 8/2008 | Korman |
| 7,421,883 B2 | 9/2008 | Khadkikar et al. |
| 7,435,386 B2 | 10/2008 | Medintz et al. |
| 7,438,079 B2 | 10/2008 | Cohen et al. |
| 7,440,844 B2 | 10/2008 | Barta et al. |
| 7,449,050 B2 | 11/2008 | Wohltjen et al. |
| 7,463,142 B2 | 12/2008 | Lindsay |
| 7,471,185 B2 | 12/2008 | Sunshine et al. |
| 7,477,994 B2 | 1/2009 | Sunshine et al. |
| 7,485,419 B2 | 2/2009 | Lu et al. |
| 7,486,979 B2 | 2/2009 | Matlock |
| 7,489,252 B2 | 2/2009 | Long et al. |
| 7,501,091 B2 | 3/2009 | Munoz et al. |
| 7,527,821 B2 | 5/2009 | Nakayama et al. |
| 7,531,136 B2 | 5/2009 | Besnard et al. |
| 7,531,137 B2 | 5/2009 | Uluyol |
| 7,534,560 B2 | 5/2009 | Lu et al. |
| 7,538,538 B2 | 5/2009 | Dodabalapur et al. |
| 7,550,310 B2 | 6/2009 | Goodman et al. |
| 7,552,031 B2 | 6/2009 | Vock et al. |
| 7,555,327 B2 | 6/2009 | Matlock |
| 7,556,775 B2 | 7/2009 | McGill et al. |
| 7,559,902 B2 | 7/2009 | Ting et al. |
| 7,569,354 B2 | 8/2009 | Okano et al. |
| 7,574,244 B2 | 8/2009 | Eghbal et al. |
| 7,574,245 B2 | 8/2009 | Arizaga Ballesteros |
| 7,590,439 B2 | 9/2009 | Raridan et al. |
| 7,595,023 B2 | 9/2009 | Lewis et al. |
| 7,595,734 B2 | 9/2009 | Long et al. |
| 7,598,878 B2 | 10/2009 | Goldreich |
| 7,611,628 B1 | 11/2009 | Hinds, III |
| 7,612,185 B2 | 11/2009 | Lu et al. |
| 7,620,520 B2 | 11/2009 | Vock et al. |
| 7,627,451 B2 | 12/2009 | Vock et al. |
| 7,645,422 B2 | 1/2010 | Blok et al. |
| 7,647,084 B2 | 1/2010 | Eghbal et al. |
| 7,650,177 B2 | 1/2010 | Hoarau et al. |
| 7,657,294 B2 | 2/2010 | Eghbal et al. |
| 7,657,295 B2 | 2/2010 | Coakley et al. |
| 7,657,296 B2 | 2/2010 | Raridan et al. |
| 7,658,612 B2 | 2/2010 | Lee et al. |
| 7,673,528 B2 | 3/2010 | Yoon et al. |
| 7,684,843 B2 | 3/2010 | Coakley et al. |
| 7,693,559 B2 | 4/2010 | Raridan et al. |
| 7,695,738 B2 | 4/2010 | Lin et al. |
| 7,701,332 B2 | 4/2010 | Anderson |
| 7,708,947 B2 | 5/2010 | West et al. |
| 7,711,506 B2 | 5/2010 | Burdett et al. |
| 7,726,175 B2 | 6/2010 | Porter et al. |
| 7,731,517 B2 | 6/2010 | Lee et al. |
| 7,737,322 B2 | 6/2010 | Ales, III et al. |
| 7,738,937 B2 | 6/2010 | Coakley et al. |
| 7,753,685 B2 | 7/2010 | Lee et al. |
| 7,760,101 B2 | 7/2010 | Ales, III et al. |
| 7,793,675 B2 | 9/2010 | Cohen et al. |
| 7,799,276 B2 | 9/2010 | Hartmann-Thompson |
| 7,799,554 B2 | 9/2010 | Mazumdar et al. |
| 7,801,687 B1 | 9/2010 | Li et al. |
| 7,811,234 B2 | 10/2010 | McGrath |
| 7,816,491 B2 | 10/2010 | Trent et al. |
| 7,825,815 B2 | 11/2010 | Shears et al. |
| 7,827,011 B2 | 11/2010 | DeVaul et al. |
| 7,840,359 B2 | 11/2010 | Hsiung et al. |
| 7,856,339 B2 | 12/2010 | Vock et al. |
| 7,860,725 B2 | 12/2010 | Gopinathan et al. |
| 7,863,376 B2 | 1/2011 | Costanzo et al. |
| 7,869,850 B2 | 1/2011 | Hoarau et al. |
| 7,880,026 B2 | 2/2011 | Ni et al. |
| 7,881,762 B2 | 2/2011 | Kling et al. |
| 7,881,862 B2 | 2/2011 | Pei et al. |
| 7,889,954 B2 | 2/2011 | Sailor et al. |
| 7,904,285 B2 | 3/2011 | McNabb |
| 7,911,010 B2 | 3/2011 | Stetter |
| 7,912,561 B2 | 3/2011 | Hsiung et al. |
| 7,927,558 B2 | 4/2011 | Kirollos et al. |
| 7,939,130 B2 | 5/2011 | Joseph et al. |
| 7,950,271 B2 | 5/2011 | Novak et al. |
| 7,955,561 B2 | 6/2011 | Lewis et al. |
| 7,959,567 B2 | 6/2011 | Stivoric et al. |
| 7,966,132 B2 | 6/2011 | Lewis et al. |
| 7,985,424 B2 | 7/2011 | Tomalia et al. |
| 7,998,415 B2 | 8/2011 | Hartmann-Thompson |
| 7,998,416 B2 | 8/2011 | Hartmann-Thompson |
| 8,000,903 B1 | 8/2011 | Li |
| 8,012,326 B2 | 9/2011 | Weiller et al. |
| 8,012,420 B2 | 9/2011 | Ramamurthy et al. |
| 8,012,743 B2 | 9/2011 | Bamdad et al. |
| 8,030,100 B2 | 10/2011 | Besnard et al. |
| 8,032,199 B2 | 10/2011 | Linti et al. |
| 8,036,842 B2 | 10/2011 | DeVaul et al. |
| 8,060,171 B2 | 11/2011 | Hoarau et al. |
| 8,063,307 B2 | 11/2011 | Bukshpun et al. |
| 8,067,393 B2 | 11/2011 | Suda et al. |
| 8,070,508 B2 | 12/2011 | Flagler |
| 8,071,935 B2 | 12/2011 | Besko et al. |
| 8,087,283 B2 | 1/2012 | Wang et al. |
| 8,088,341 B2 | 1/2012 | Martin |
| 8,094,009 B2 | 1/2012 | Allen et al. |
| 8,097,926 B2 | 1/2012 | De Graff et al. |
| 8,105,538 B2 | 1/2012 | Ramamurthy et al. |
| 8,107,920 B2 | 1/2012 | Ben Ayed |
| 8,123,834 B2 | 2/2012 | Masel et al. |
| 8,123,841 B2 | 2/2012 | Masel et al. |
| 8,125,331 B2 | 2/2012 | Allen et al. |
| 8,126,675 B2 | 2/2012 | Vock et al. |
| 8,152,908 B2 | 4/2012 | Masel et al. |
| 8,153,439 B2 | 4/2012 | Zamborini et al. |
| 8,157,730 B2 | 4/2012 | LeBoeuf et al. |
| 8,157,731 B2 | 4/2012 | Teller et al. |
| 8,168,438 B2 | 5/2012 | Zamborini et al. |
| 8,175,671 B2 | 5/2012 | Hoarau |
| 8,178,045 B2 | 5/2012 | Cambron et al. |
| 8,187,887 B2 | 5/2012 | Swager et al. |
| 8,190,224 B2 | 5/2012 | Hoarau |
| 8,190,225 B2 | 5/2012 | Hoarau |
| 8,195,264 B2 | 6/2012 | Hoarau |
| 8,199,007 B2 | 6/2012 | Coakley et al. |
| 8,204,786 B2 | 6/2012 | LeBoeuf et al. |
| 8,216,854 B2 | 7/2012 | Ballerstadt et al. |
| 8,219,170 B2 | 7/2012 | Hausmann et al. |
| 8,228,188 B2 | 7/2012 | Key et al. |
| 8,231,746 B1 | 7/2012 | Bellitto |
| 8,246,910 B2 | 8/2012 | Dhirani et al. |
| 8,251,903 B2 | 8/2012 | LeBoeuf et al. |
| 8,268,630 B2 | 9/2012 | Fedder et al. |
| 8,269,029 B2 | 9/2012 | Masel et al. |
| 8,272,250 B2 | 9/2012 | Wang et al. |
| 8,275,635 B2 | 9/2012 | Stivoric et al. |
| 8,280,469 B2 | 10/2012 | Baker, Jr. |
| 8,280,681 B2 | 10/2012 | Vock et al. |
| 8,280,682 B2 | 10/2012 | Vock et al. |
| 8,282,967 B2 | 10/2012 | Schoenfisch et al. |
| 8,283,414 B2 | 10/2012 | Yu et al. |
| 8,284,046 B2 | 10/2012 | Allen et al. |
| 8,285,493 B2 | 10/2012 | Sunshine et al. |
| 8,285,560 B2 | 10/2012 | Gopinathan et al. |
| 8,308,489 B2 | 11/2012 | Lee et al. |
| 8,309,028 B2 | 11/2012 | Raguse et al. |
| 8,310,016 B2 | 11/2012 | Stetter |
| 8,311,602 B2 | 11/2012 | Eghbal et al. |
| 8,315,685 B2 | 11/2012 | Arizaga Ballesteros |
| 8,323,188 B2 | 12/2012 | Tran |
| 8,323,694 B2 | 12/2012 | Hainfeld |

(56) References Cited

U.S. PATENT DOCUMENTS

| | | |
|---|---|---|
| 8,323,888 B2 | 12/2012 | Mirkin et al. |
| 8,323,982 B2 | 12/2012 | LeBoeuf et al. |
| 8,328,420 B2 | 12/2012 | Abreu |
| 8,336,402 B2 | 12/2012 | Glezer et al. |
| 8,352,010 B2 | 1/2013 | Matlock |
| 8,352,049 B2 | 1/2013 | Hsiung et al. |
| 8,352,172 B2 | 1/2013 | Pei et al. |
| 8,358,214 B2 | 1/2013 | Amigo et al. |
| 8,366,630 B2 | 2/2013 | Haick et al. |
| 8,369,936 B2 | 2/2013 | Farringdon et al. |
| 8,374,825 B2 | 2/2013 | Vock et al. |
| 8,376,013 B2 | 2/2013 | Bourke, Jr. et al. |
| 8,382,590 B2 | 2/2013 | Stivoric et al. |
| 8,383,415 B2 | 2/2013 | Ayi et al. |
| 8,386,002 B2 | 2/2013 | Matlock |
| 8,389,958 B2 | 3/2013 | Vo-Dinh et al. |
| 8,394,330 B1 | 3/2013 | Lewis et al. |
| 8,396,527 B2 | 3/2013 | Hoarau |
| 8,396,687 B2 | 3/2013 | Vock et al. |
| 8,398,546 B2 | 3/2013 | Pacione et al. |
| 8,409,510 B2 | 4/2013 | McGill et al. |
| 8,412,147 B2 | 4/2013 | Hunter et al. |
| 8,426,208 B2 | 4/2013 | Swager et al. |
| 8,426,214 B2 | 4/2013 | Stayton et al. |
| 8,426,932 B2 | 4/2013 | Stetter |
| 8,428,675 B2 | 4/2013 | McKenna |
| 8,428,904 B2 | 4/2013 | Vock et al. |
| 8,441,081 B2 | 5/2013 | Arora et al. |
| 8,448,532 B2 | 5/2013 | Martin et al. |
| 8,449,471 B2 | 5/2013 | Tran |
| 8,449,824 B2 | 5/2013 | Sun |
| 8,452,366 B2 | 5/2013 | Gilland |
| 8,461,354 B2 | 6/2013 | Babudri et al. |
| 8,467,133 B2 | 6/2013 | Miller |
| 8,472,120 B2 | 6/2013 | Border et al. |
| 8,477,425 B2 | 7/2013 | Border et al. |
| 8,481,324 B2 | 7/2013 | Haick et al. |
| 8,482,859 B2 | 7/2013 | Border et al. |
| 8,486,720 B2 | 7/2013 | Banerjee et al. |
| 8,488,246 B2 | 7/2013 | Border et al. |
| 8,497,130 B2 | 7/2013 | Raguse et al. |
| 8,498,811 B2 | 7/2013 | Lundquist et al. |
| RE44,408 E | 8/2013 | Lindsay |
| 8,501,921 B2 | 8/2013 | Bamdad et al. |
| 8,507,200 B2 | 8/2013 | Mirkin et al. |
| 8,512,242 B2 | 8/2013 | LeBoeuf et al. |
| 8,515,515 B2 | 8/2013 | McKenna et al. |
| 8,515,537 B2 | 8/2013 | Cinbis et al. |
| 8,519,726 B2 | 8/2013 | Sun |
| 8,524,457 B2 | 9/2013 | Patterson |
| 8,527,028 B2 | 9/2013 | Kurzweil et al. |
| 8,527,213 B2 | 9/2013 | Kailas et al. |
| 8,528,185 B2 | 9/2013 | Raridan et al. |
| 8,536,667 B2 | 9/2013 | de Graff et al. |
| 8,553,223 B2 | 10/2013 | McKenna |
| 8,560,044 B2 | 10/2013 | Kurzweil et al. |
| 8,562,878 B1 | 10/2013 | Martin et al. |
| 8,567,232 B2 | 10/2013 | Ackley et al. |
| 8,569,691 B2 | 10/2013 | Cambron et al. |
| 8,571,620 B2 | 10/2013 | Cinbis et al. |
| 8,579,834 B2 | 11/2013 | Davis et al. |
| 8,598,046 B2 | 12/2013 | Pachauri et al. |
| 8,618,330 B2 | 12/2013 | Snow |
| 8,618,509 B2 | 12/2013 | Vo-Dinh et al. |
| 8,636,670 B2 | 1/2014 | Ferren et al. |
| 8,638,228 B2 | 1/2014 | Amigo et al. |
| 8,641,612 B2 | 2/2014 | Teller et al. |
| 8,652,409 B2 | 2/2014 | LeBoeuf et al. |
| 8,652,778 B2 | 2/2014 | Bowman et al. |
| 8,655,441 B2 | 2/2014 | Fletcher et al. |
| 8,660,814 B2 | 2/2014 | Vock et al. |
| 8,665,087 B2 | 3/2014 | Greene et al. |
| 8,666,471 B2 | 3/2014 | Rogers et al. |
| 8,679,859 B2 | 3/2014 | Yan et al. |
| 8,684,900 B2 | 4/2014 | Tran |
| 8,688,406 B2 | 4/2014 | Vock et al. |
| 8,690,799 B2 | 4/2014 | Telfort et al. |
| 8,691,390 B2 | 4/2014 | Ramamurthy |
| 8,694,267 B2 | 4/2014 | Sunshine et al. |
| 8,695,401 B2 | 4/2014 | Wang et al. |
| 8,696,616 B2 | 4/2014 | Baynham et al. |
| 8,702,607 B2 | 4/2014 | LeBoeuf et al. |
| 8,702,627 B2 | 4/2014 | Telfort et al. |
| 8,703,439 B1 | 4/2014 | Lester |
| 8,703,500 B2 | 4/2014 | Zang et al. |
| 8,707,760 B2 | 4/2014 | Chou et al. |
| 8,708,904 B2 | 4/2014 | Stivoric et al. |
| 8,714,983 B2 | 5/2014 | Kil |
| 8,715,206 B2 | 5/2014 | Telfort et al. |
| 8,717,558 B2 | 5/2014 | Gu et al. |
| 8,721,562 B2 | 5/2014 | Abreu |
| 8,731,512 B2 | 5/2014 | Borras et al. |
| 8,736,287 B2 | 5/2014 | Dhirani et al. |
| 8,744,783 B2 | 6/2014 | Templeman |
| 8,755,535 B2 | 6/2014 | Telfort et al. |
| 8,758,772 B2 | 6/2014 | Mehra et al. |
| 8,759,791 B1 | 6/2014 | Hug et al. |
| 8,764,657 B2 | 7/2014 | Curry et al. |
| 8,770,203 B2 | 7/2014 | Bourke, Jr. et al. |
| 8,771,613 B2 | 7/2014 | Martin et al. |
| 8,781,548 B2 | 7/2014 | Besko et al. |
| 8,788,002 B2 | 7/2014 | LeBoeuf et al. |
| 8,790,400 B2 | 7/2014 | Boyden et al. |
| 8,795,173 B2 | 8/2014 | Poh et al. |
| 8,795,359 B2 | 8/2014 | Boyden et al. |
| 8,798,702 B2 | 8/2014 | Trumble |
| 8,805,465 B2 | 8/2014 | Hodge et al. |
| 8,808,373 B2 | 8/2014 | Boyden et al. |
| 8,812,130 B2 | 8/2014 | Stahmann et al. |
| 8,816,116 B2 | 8/2014 | Snow |
| 8,828,733 B2 | 9/2014 | Porter et al. |
| 8,834,020 B2 | 9/2014 | Abreu |
| 8,844,057 B2 | 9/2014 | Root et al. |
| 8,846,406 B1 | 9/2014 | Martin et al. |
| 8,849,379 B2 | 9/2014 | Abreu |
| 8,852,098 B2 | 10/2014 | Teller et al. |
| 8,870,766 B2 | 10/2014 | Stivoric et al. |
| 8,877,636 B1 | 11/2014 | Hunter et al. |
| 8,883,964 B2 | 11/2014 | Yu et al. |
| 8,884,382 B2 | 11/2014 | Stetter et al. |
| 8,888,701 B2 | 11/2014 | LeBoeuf et al. |
| 8,889,420 B2 | 11/2014 | Zang et al. |
| 8,900,516 B2 | 12/2014 | Joseph et al. |
| 8,903,661 B2 | 12/2014 | Haick et al. |
| 8,904,849 B2 | 12/2014 | Norman et al. |
| 8,906,831 B2 | 12/2014 | Eid et al. |
| 8,920,731 B2 | 12/2014 | Nhan et al. |
| 8,920,971 B2 | 12/2014 | Stromme et al. |
| 8,927,615 B2 | 1/2015 | Bourke, Jr. et al. |
| 8,929,963 B2 | 1/2015 | Lisogurski |
| 8,929,965 B2 | 1/2015 | LeBoeuf et al. |
| 8,935,195 B2 | 1/2015 | Precup et al. |
| 8,940,092 B1 | 1/2015 | Yeo et al. |
| 8,942,776 B2 | 1/2015 | LeBoeuf et al. |
| 8,945,943 B2 | 2/2015 | Lu et al. |
| 8,951,473 B2 | 2/2015 | Wang et al. |
| 8,951,561 B2 | 2/2015 | Vo-Dinh et al. |
| 8,956,658 B2 | 2/2015 | Schoenfisch et al. |
| 8,956,863 B2 | 2/2015 | Karp et al. |
| 8,957,253 B2 | 2/2015 | Snow |
| 8,961,414 B2 | 2/2015 | Teller et al. |
| 8,961,415 B2 | 2/2015 | LeBoeuf et al. |
| 8,962,029 B2 | 2/2015 | Schoenfisch et al. |
| 8,962,912 B2 | 2/2015 | Sasgary et al. |
| 8,964,298 B2 | 2/2015 | Haddick et al. |
| 8,965,473 B2 | 2/2015 | Hoarau et al. |
| 8,968,196 B2 | 3/2015 | Teller et al. |
| 8,978,444 B2 | 3/2015 | Chou et al. |
| 8,984,954 B2 | 3/2015 | Merrell et al. |
| 8,986,615 B1 | 3/2015 | Ancona et al. |
| 8,989,053 B1 | 3/2015 | Skaaksrud et al. |
| 8,993,349 B2 | 3/2015 | Bruchez et al. |
| 8,999,244 B2 | 4/2015 | Haick et al. |
| 8,999,245 B2 | 4/2015 | Wang et al. |

(56) References Cited

U.S. PATENT DOCUMENTS

| | | |
|---|---|---|
| 8,999,947 B2 | 4/2015 | Mirkin et al. |
| 9,000,137 B2 | 4/2015 | Tanner et al. |
| 9,004,131 B2 | 4/2015 | Bourke, Jr. et al. |
| 9,011,349 B2 | 4/2015 | Abreu |
| 9,012,156 B2 | 4/2015 | Patterson |
| 9,017,773 B2 | 4/2015 | D'Arcy et al. |
| 9,020,752 B2 | 4/2015 | Lundquist et al. |
| 9,028,405 B2 | 5/2015 | Tran |
| 9,033,876 B2 | 5/2015 | Teller et al. |
| 9,034,266 B2 | 5/2015 | Virji et al. |
| 9,034,275 B2 | 5/2015 | Lee et al. |
| 9,034,659 B2 | 5/2015 | Bhattacharyya et al. |
| 9,042,596 B2 | 5/2015 | Connor |
| 9,044,180 B2 | 6/2015 | LeBoeuf et al. |
| 9,050,471 B2 | 6/2015 | Skelton et al. |
| 9,058,703 B2 | 6/2015 | Ricci |
| 9,060,714 B2 | 6/2015 | Bajcsy et al. |
| 9,067,070 B2 | 6/2015 | Connor |
| 9,067,181 B2 | 6/2015 | Rybtchinski et al. |
| 9,072,941 B2 | 7/2015 | Duda et al. |
| 9,078,610 B2 | 7/2015 | McKenna |
| 9,080,942 B2 | 7/2015 | Zhong et al. |
| 9,097,890 B2 | 8/2015 | Miller et al. |
| 9,097,891 B2 | 8/2015 | Border et al. |
| 9,102,520 B2 | 8/2015 | Han et al. |
| 9,114,107 B2 | 8/2015 | Chaiken et al. |
| 9,119,533 B2 | 9/2015 | Ghaffari |
| 9,120,677 B2 | 9/2015 | Watson et al. |
| 9,125,625 B2 | 9/2015 | Wang et al. |
| 9,128,281 B2 | 9/2015 | Osterhout et al. |
| 9,129,295 B2 | 9/2015 | Border et al. |
| 9,132,217 B2 | 9/2015 | Soykan et al. |
| 9,134,534 B2 | 9/2015 | Border et al. |
| 9,141,994 B2 | 9/2015 | Amigo et al. |
| 9,144,488 B2 | 9/2015 | Boyden et al. |
| 9,144,489 B2 | 9/2015 | Boyden et al. |
| 9,147,144 B2 | 9/2015 | Potyrailo et al. |
| 9,147,338 B2 | 9/2015 | Hunter et al. |
| RE45,766 E | 10/2015 | Lindsay |
| 9,157,109 B2 | 10/2015 | Brennan et al. |
| 9,157,842 B1 | 10/2015 | Ancona et al. |
| 9,162,063 B2 | 10/2015 | Stahmann et al. |
| 9,165,117 B2 | 10/2015 | Teller et al. |
| 9,174,055 B2 | 11/2015 | Davis et al. |
| 9,174,190 B2 | 11/2015 | Bourke, Jr. et al. |
| 9,174,873 B2 | 11/2015 | Laukkanen et al. |
| 9,182,231 B2 | 11/2015 | Skaaksrud |
| 9,182,232 B2 | 11/2015 | Skaaksrud et al. |
| 9,182,596 B2 | 11/2015 | Border et al. |
| 9,186,060 B2 | 11/2015 | De Graff et al. |
| 9,186,098 B2 | 11/2015 | Lee et al. |
| 9,198,605 B2 | 12/2015 | Contant |
| 9,198,617 B2 | 12/2015 | Kurzweil et al. |
| 9,201,071 B2 | 12/2015 | Mehra et al. |
| 9,204,808 B2 | 12/2015 | Riedel |
| 9,211,185 B2 | 12/2015 | Boyden et al. |
| 9,212,055 B2 | 12/2015 | Zhou et al. |
| 9,215,992 B2 | 12/2015 | Donnay et al. |
| 9,216,155 B2 | 12/2015 | Thaxton et al. |
| 9,216,528 B2 | 12/2015 | Raridan et al. |
| 9,217,722 B2 | 12/2015 | Mirsky et al. |
| 9,222,884 B2 | 12/2015 | Im et al. |
| 9,223,134 B2 | 12/2015 | Miller et al. |
| 9,229,227 B2 | 1/2016 | Border et al. |
| 9,234,757 B2 | 1/2016 | Skaaksrud et al. |
| 9,242,857 B2 | 1/2016 | Ostroff et al. |
| 9,243,128 B2 | 1/2016 | Kumamoto et al. |
| 9,246,122 B2 | 1/2016 | Shinotsuka et al. |
| 9,250,238 B2 | 2/2016 | Low et al. |
| 9,254,099 B2 | 2/2016 | Connor |
| 9,254,383 B2 | 2/2016 | Simon et al. |
| 9,254,437 B2 | 2/2016 | Short et al. |
| 9,256,906 B2 | 2/2016 | Amigo et al. |
| 9,258,350 B2 | 2/2016 | Root et al. |
| 9,260,683 B2 | 2/2016 | Belbruno et al. |
| 9,262,772 B2 | 2/2016 | Stivoric et al. |
| 9,265,453 B2 | 2/2016 | Curry et al. |
| 9,265,949 B2 | 2/2016 | Salo et al. |
| 9,267,793 B2 | 2/2016 | Vock et al. |
| 9,267,908 B2 | 2/2016 | Wang et al. |
| 9,267,964 B2 | 2/2016 | Flanders et al. |
| 9,269,000 B2 | 2/2016 | Korhonen et al. |
| 9,270,627 B1 | 2/2016 | Koo |
| 9,272,091 B2 | 3/2016 | Skelton et al. |
| 9,274,108 B2 | 3/2016 | Yoo et al. |
| 9,276,238 B2 | 3/2016 | Shinotsuka et al. |
| 9,277,867 B2 | 3/2016 | Kurzweil et al. |
| 9,282,574 B2 | 3/2016 | Kuroda |
| 9,283,275 B2 | 3/2016 | Vo-Dinh et al. |
| 9,285,589 B2 | 3/2016 | Osterhout et al. |
| 9,289,175 B2 | 3/2016 | LeBoeuf et al. |
| 9,290,799 B2 | 3/2016 | Chen et al. |
| 9,301,092 B2 | 3/2016 | Huang |
| 9,301,719 B2 | 4/2016 | Abreu |
| 9,302,116 B2 | 4/2016 | Vo-Dinh et al. |
| 9,310,372 B2 | 4/2016 | Patterson |
| 9,315,848 B2 | 4/2016 | Haick et al. |
| 9,315,942 B2 | 4/2016 | Nuopponen et al. |
| 9,316,645 B2 | 4/2016 | Rose-Petruck et al. |
| 9,320,813 B2 | 4/2016 | Peyman |
| 9,320,842 B2 | 4/2016 | Orhan et al. |
| 9,321,030 B2 | 4/2016 | Sukhishvili et al. |
| 9,326,730 B2 | 5/2016 | Boyden et al. |
| 9,326,731 B2 | 5/2016 | Naing et al. |
| 9,333,071 B2 | 5/2016 | Boyden et al. |
| 9,333,163 B2 | 5/2016 | Farokhzad et al. |
| 9,339,372 B2 | 5/2016 | Boyden et al. |
| 9,340,416 B2 | 5/2016 | Maune et al. |
| 9,341,843 B2 | 5/2016 | Border et al. |
| 9,349,234 B2 | 5/2016 | Ricci |
| 9,351,669 B2 | 5/2016 | Stafford |
| 9,360,509 B2 | 6/2016 | Naughton et al. |
| 9,366,862 B2 | 6/2016 | Haddick et al. |
| 9,376,690 B2 | 6/2016 | Mirkin et al. |
| 9,377,426 B2 | 6/2016 | Myung et al. |
| 9,384,609 B2 | 7/2016 | Ricci |
| 9,389,260 B2 | 7/2016 | Potyrailo et al. |
| 9,393,396 B2 | 7/2016 | Peyman |
| 9,396,486 B2 | 7/2016 | Stivoric et al. |
| 9,398,856 B2 | 7/2016 | Abreu |
| 9,402,242 B2 | 7/2016 | Skaaksrud et al. |
| 9,403,851 B2 | 8/2016 | Schoenfisch et al. |
| 9,403,852 B2 | 8/2016 | Schoenfisch et al. |
| 9,408,572 B2 | 8/2016 | Abreu |
| 9,410,949 B2 | 8/2016 | Singamaneni et al. |
| 9,412,273 B2 | 8/2016 | Ricci |
| 9,415,125 B2 | 8/2016 | Chen et al. |
| 9,416,493 B2 | 8/2016 | Hillebrand et al. |
| 9,426,433 B1 | 8/2016 | Mazzarella et al. |
| 9,429,536 B2 | 8/2016 | BelBruno et al. |
| 9,437,628 B1 | 9/2016 | Ma et al. |
| 9,439,566 B2 | 9/2016 | Arne et al. |
| 9,439,567 B2 | 9/2016 | Carter et al. |
| 9,439,797 B2 | 9/2016 | Baym et al. |
| 9,439,868 B2 | 9/2016 | Scherman et al. |
| 9,440,195 B2 | 9/2016 | Montemagno |
| 9,442,070 B1 | 9/2016 | Hug et al. |
| 9,442,100 B2 | 9/2016 | Connor |
| 9,445,720 B2 | 9/2016 | Janna et al. |
| 9,445,767 B2 | 9/2016 | Abreu |
| 9,446,150 B2 | 9/2016 | Lanza et al. |
| 9,447,129 B2 | 9/2016 | Johnson et al. |
| 9,448,219 B2 | 9/2016 | Arora et al. |
| 9,449,084 B2 | 9/2016 | Chong et al. |
| 9,453,774 B2 | 9/2016 | Bao et al. |
| 9,453,811 B2 | 9/2016 | Duesberg et al. |
| 9,456,755 B2 | 10/2016 | Soykan et al. |
| 9,459,222 B2 | 10/2016 | Swager et al. |
| 9,459,223 B1 | 10/2016 | Alqahtani et al. |
| 9,462,979 B2 | 10/2016 | Lisogurski et al. |
| 9,476,862 B2 | 10/2016 | Motayed et al. |
| 9,486,512 B2 | 11/2016 | Kim et al. |
| 9,494,524 B2 | 11/2016 | Mager et al. |
| 9,494,541 B2 | 11/2016 | Potyrailo et al. |

(56) References Cited

U.S. PATENT DOCUMENTS

| | | |
|---|---|---|
| 9,504,423 B1 | 11/2016 | Bardy et al. |
| 9,506,056 B2 | 11/2016 | Mirkin et al. |
| 9,508,956 B2 | 11/2016 | Shinotsuka et al. |
| 9,510,316 B2 | 11/2016 | Skaaksrud |
| 9,510,784 B2 | 12/2016 | Benson et al. |
| 9,511,329 B2 | 12/2016 | Chu et al. |
| 9,514,278 B2 | 12/2016 | Bahorich |
| 9,514,632 B2 | 12/2016 | Hunter et al. |
| 9,515,417 B2 | 12/2016 | Fries et al. |
| 9,518,956 B2 | 12/2016 | Chung et al. |
| 9,521,962 B2 | 12/2016 | LeBoeuf |
| 9,522,317 B2 | 12/2016 | Bleich et al. |
| 9,524,597 B2 | 12/2016 | Ricci |
| 9,526,913 B2 | 12/2016 | Vo-Dinh et al. |
| 9,526,914 B2 | 12/2016 | Vo-Dinh et al. |
| 9,529,385 B2 | 12/2016 | Connor |
| 9,532,737 B2 | 1/2017 | Karan et al. |
| 9,532,956 B2 | 1/2017 | Radovic-Moreno et al. |
| 9,534,024 B2 | 1/2017 | Gundlach et al. |
| 9,536,122 B2 | 1/2017 | Potyrailo |
| 9,536,449 B2 | 1/2017 | Connor |
| 9,538,657 B2 | 1/2017 | Potyrailo et al. |
| 9,538,921 B2 | 1/2017 | LeBoeuf et al. |
| 9,538,980 B2 | 1/2017 | Telfort et al. |
| 9,540,422 B2 | 1/2017 | Gundlach et al. |
| 9,545,221 B2 | 1/2017 | Adhikari et al. |
| 9,555,392 B2 | 1/2017 | Thomas et al. |
| 9,556,473 B2 | 1/2017 | Bernitz et al. |
| 9,557,340 B2 | 1/2017 | Foehr et al. |
| 9,563,833 B2 | 2/2017 | Swager et al. |
| 9,563,995 B2 | 2/2017 | Freathy |
| 9,567,225 B2 | 2/2017 | Lin et al. |
| 9,567,645 B2 | 2/2017 | Fan et al. |
| 9,567,646 B2 | 2/2017 | Fan et al. |
| 9,572,647 B2 | 2/2017 | Couse et al. |
| 9,579,024 B2 | 2/2017 | Nyberg et al. |
| 9,579,040 B2 | 2/2017 | Rafferty et al. |
| 9,579,523 B2 | 2/2017 | Bourke, Jr. et al. |
| 9,581,590 B2 | 2/2017 | Alocilja et al. |
| 9,582,035 B2 | 2/2017 | Connor |
| 9,582,072 B2 | 2/2017 | Connor |
| 9,582,080 B1 | 2/2017 | Tilton et al. |
| 9,582,833 B2 | 2/2017 | Amigo et al. |
| 9,589,686 B2 | 3/2017 | Potyrailo et al. |
| 9,590,438 B2 | 3/2017 | Dalton et al. |
| 9,591,607 B2 | 3/2017 | Skaaksrud |
| 9,592,007 B2 | 3/2017 | Nuovo et al. |
| 9,592,198 B2 | 3/2017 | Hood et al. |
| 9,594,402 B2 | 3/2017 | Hiroki et al. |
| 9,597,004 B2 | 3/2017 | Hughes et al. |
| 9,598,282 B2 | 3/2017 | Han et al. |
| 9,598,544 B2 | 3/2017 | Jiang et al. |
| 9,598,736 B2 | 3/2017 | Fan et al. |
| 9,598,785 B2 | 3/2017 | Patolsky et al. |
| 9,603,560 B2 | 3/2017 | Monty et al. |
| 9,604,168 B2 | 3/2017 | Menkhaus et al. |
| 9,606,245 B1 | 3/2017 | Czarnecki et al. |
| 9,613,521 B2 | 4/2017 | Hunter et al. |
| 9,613,659 B2 | 4/2017 | Maser et al. |
| 9,615,798 B2 | 4/2017 | Kasahara et al. |
| 9,619,213 B2 | 4/2017 | Gupta et al. |
| 9,620,000 B2 | 4/2017 | Wang et al. |
| 9,622,725 B2 | 4/2017 | Pizer et al. |
| 9,623,352 B2 | 4/2017 | Kas et al. |
| 9,623,381 B2 | 4/2017 | Rybtchinski et al. |
| 9,624,275 B2 | 4/2017 | Gundlach et al. |
| 9,625,330 B2 | 4/2017 | Park et al. |
| 9,625,341 B2 | 4/2017 | Haick et al. |
| 9,630,011 B2 | 4/2017 | Lipani |
| 9,630,022 B2 | 4/2017 | Bourke, Jr. et al. |
| 9,632,050 B2 | 4/2017 | Zhong et al. |
| 9,636,061 B2 | 5/2017 | Nyberg et al. |
| 9,636,992 B2 | 5/2017 | Biderman et al. |
| 9,636,993 B2 | 5/2017 | Biderman |
| 9,637,380 B2 | 5/2017 | Turner et al. |
| 9,637,799 B2 | 5/2017 | Fan et al. |
| 9,637,830 B2 | 5/2017 | Wang et al. |
| 9,638,653 B2 | 5/2017 | Potyrailo et al. |
| 9,643,091 B2 | 5/2017 | Vock et al. |
| 9,645,133 B2 | 5/2017 | Pizer et al. |
| 9,649,391 B2 | 5/2017 | Farokhzad et al. |
| 9,654,200 B2 | 5/2017 | Mazzarella et al. |
| 9,658,178 B2 | 5/2017 | Surman et al. |
| 9,658,196 B2 | 5/2017 | Chou et al. |
| 9,662,069 B2 | 5/2017 | De Graff et al. |
| 9,662,299 B2 | 5/2017 | Ostroff et al. |
| 9,662,388 B2 | 5/2017 | Vo-Dinh et al. |
| 9,662,389 B2 | 5/2017 | Vo-Dinh et al. |
| 9,664,674 B2 | 5/2017 | Taslim et al. |
| 9,669,699 B2 | 6/2017 | Biderman et al. |
| 9,669,700 B2 | 6/2017 | Biderman et al. |
| 9,674,812 B2 | 6/2017 | Skaaksrud et al. |
| 9,678,059 B2 | 6/2017 | Haick et al. |
| 9,683,974 B2 | 6/2017 | Wang et al. |
| 9,686,499 B2 | 6/2017 | Ekambaram et al. |
| 9,687,183 B2 | 6/2017 | Donnay et al. |
| 9,688,750 B2 | 6/2017 | Ruvo et al. |
| 9,689,826 B2 | 6/2017 | Haick et al. |
| 9,691,428 B2 | 6/2017 | Maser et al. |
| 9,691,873 B2 | 6/2017 | Rogers et al. |
| 9,696,311 B2 | 7/2017 | Haick et al. |
| 9,696,833 B2 | 7/2017 | McMillen |
| 9,701,190 B2 | 7/2017 | Biderman et al. |
| 9,701,784 B2 | 7/2017 | Rybtchinski et al. |
| 9,703,751 B2 | 7/2017 | White et al. |
| 9,704,205 B2 | 7/2017 | Akutagawa et al. |
| 9,707,466 B2 | 7/2017 | Bleich et al. |
| 9,709,559 B2 | 7/2017 | Banerjee et al. |
| 9,713,447 B2 | 7/2017 | Caduff et al. |
| 9,714,370 B2 | 7/2017 | Mrozek et al. |
| 9,717,455 B2 | 8/2017 | Manion et al. |
| 9,717,685 B2 | 8/2017 | Shih et al. |
| 9,719,089 B2 | 8/2017 | Mirkin et al. |
| 2001/0029774 A1 | 10/2001 | Grate et al. |
| 2001/0041366 A1 | 11/2001 | Lewis et al. |
| 2001/0049471 A1 | 12/2001 | Suzuki et al. |
| 2002/0002414 A1 | 1/2002 | Hsiung et al. |
| 2002/0004995 A1 | 1/2002 | France et al. |
| 2002/0005580 A1 | 1/2002 | Goodman et al. |
| 2002/0014415 A1 | 2/2002 | Nakayama et al. |
| 2002/0017125 A1 | 2/2002 | Lewis et al. |
| 2002/0028988 A1 | 3/2002 | Suzuki et al. |
| 2002/0045274 A1 | 4/2002 | Huang |
| 2002/0045275 A1 | 4/2002 | Huang |
| 2002/0081232 A1 | 6/2002 | Lewis et al. |
| 2002/0081397 A1 | 6/2002 | McGill et al. |
| 2002/0098119 A1 | 7/2002 | Goodman |
| 2002/0106709 A1 | 8/2002 | Potts et al. |
| 2002/0110901 A1 | 8/2002 | Huang |
| 2002/0120203 A1 | 8/2002 | Higurashi et al. |
| 2002/0127574 A1 | 9/2002 | Mirkin et al. |
| 2002/0131901 A1 | 9/2002 | Monkman et al. |
| 2002/0132361 A1 | 9/2002 | Vossmeyer et al. |
| 2002/0137058 A1 | 9/2002 | Mirkin et al. |
| 2002/0137070 A1 | 9/2002 | Mirkin et al. |
| 2002/0137071 A1 | 9/2002 | Mirkin et al. |
| 2002/0137072 A1 | 9/2002 | Mirkin et al. |
| 2002/0141901 A1 | 10/2002 | Lewis et al. |
| 2002/0142477 A1 | 10/2002 | Lewis et al. |
| 2002/0146720 A1 | 10/2002 | Mirkin et al. |
| 2002/0149466 A1 | 10/2002 | Sunshine et al. |
| 2002/0155442 A1 | 10/2002 | Mirkin et al. |
| 2002/0155458 A1 | 10/2002 | Mirkin et al. |
| 2002/0155459 A1 | 10/2002 | Mirkin et al. |
| 2002/0155461 A1 | 10/2002 | Mirkin et al. |
| 2002/0155462 A1 | 10/2002 | Mirkin et al. |
| 2002/0160381 A1 | 10/2002 | Mirkin et al. |
| 2002/0164605 A1 | 11/2002 | Mirkin et al. |
| 2002/0164643 A1 | 11/2002 | Huang |
| 2002/0172953 A1 | 11/2002 | Mirkin et al. |
| 2002/0178789 A1 | 12/2002 | Sunshine et al. |
| 2002/0182611 A1 | 12/2002 | Mirkin et al. |
| 2002/0182613 A1 | 12/2002 | Mirkin et al. |
| 2002/0197390 A1 | 12/2002 | Lewis et al. |

(56) References Cited

U.S. PATENT DOCUMENTS

| | | |
|---|---|---|
| 2002/0198574 A1 | 12/2002 | Gumpert |
| 2003/0010097 A1 | 1/2003 | Porter et al. |
| 2003/0022169 A1 | 1/2003 | Mirkin et al. |
| 2003/0024814 A1 | 2/2003 | Stetter |
| 2003/0044805 A1 | 3/2003 | Mirkin et al. |
| 2003/0049630 A1 | 3/2003 | Mirkin et al. |
| 2003/0049631 A1 | 3/2003 | Mirkin et al. |
| 2003/0054358 A1 | 3/2003 | Mirkin et al. |
| 2003/0059777 A1 | 3/2003 | Mirkin et al. |
| 2003/0059820 A1 | 3/2003 | Vo-Dinh |
| 2003/0068622 A1 | 4/2003 | Mirkin et al. |
| 2003/0069002 A1 | 4/2003 | Hunter et al. |
| 2003/0076968 A1 | 4/2003 | Rast |
| 2003/0083756 A1 | 5/2003 | Hsiung et al. |
| 2003/0087242 A1 | 5/2003 | Mirkin et al. |
| 2003/0109056 A1 | 6/2003 | Vossmeyer et al. |
| 2003/0109951 A1 | 6/2003 | Hsiung et al. |
| 2003/0124528 A1 | 7/2003 | Mirkin et al. |
| 2003/0136960 A1 | 7/2003 | Goodman et al. |
| 2003/0143538 A1 | 7/2003 | Mirkin et al. |
| 2003/0144746 A1 | 7/2003 | Hsiung et al. |
| 2003/0148282 A1 | 8/2003 | Mirkin et al. |
| 2003/0159927 A1 | 8/2003 | Lewis et al. |
| 2003/0163287 A1 | 8/2003 | Vock et al. |
| 2003/0165882 A1 | 9/2003 | Huang et al. |
| 2003/0165987 A1 | 9/2003 | Huang |
| 2003/0180783 A1 | 9/2003 | Mirkin et al. |
| 2003/0181795 A1 | 9/2003 | Suzuki et al. |
| 2003/0194205 A1 | 10/2003 | Suzuki et al. |
| 2003/0195398 A1 | 10/2003 | Suzuki et al. |
| 2003/0198956 A1 | 10/2003 | Makowski et al. |
| 2003/0204132 A1 | 10/2003 | Suzuki et al. |
| 2003/0207296 A1 | 11/2003 | Park et al. |
| 2003/0215903 A1 | 11/2003 | Hyman et al. |
| 2004/0018587 A1 | 1/2004 | Makowski et al. |
| 2004/0018633 A1 | 1/2004 | Foos et al. |
| 2004/0018642 A1 | 1/2004 | Huang |
| 2004/0029183 A1 | 2/2004 | Liebholz et al. |
| 2004/0029288 A1 | 2/2004 | Snow et al. |
| 2004/0033165 A1 | 2/2004 | Lewis et al. |
| 2004/0042933 A1 | 3/2004 | Lewis et al. |
| 2004/0059212 A1 | 3/2004 | Abreu |
| 2004/0072231 A1 | 4/2004 | Mirkin et al. |
| 2004/0076681 A1 | 4/2004 | Dennis et al. |
| 2004/0110220 A1 | 6/2004 | Mirkin et al. |
| 2004/0133081 A1 | 7/2004 | Teller et al. |
| 2004/0135684 A1 | 7/2004 | Steinthal et al. |
| 2004/0147038 A1 | 7/2004 | Lewis et al. |
| 2004/0152956 A1 | 8/2004 | Korman |
| 2004/0152957 A1 | 8/2004 | Stivoric et al. |
| 2004/0158194 A1 | 8/2004 | Wolff et al. |
| 2004/0192072 A1 | 9/2004 | Snow et al. |
| 2004/0194534 A1 | 10/2004 | Porter et al. |
| 2004/0200722 A1 | 10/2004 | Starling et al. |
| 2004/0202856 A1 | 10/2004 | Blok |
| 2004/0204915 A1 | 10/2004 | Steinthal et al. |
| 2004/0204920 A1 | 10/2004 | Zimmermann et al. |
| 2004/0211243 A1 | 10/2004 | Porter et al. |
| 2004/0215402 A1 | 10/2004 | Hsiung et al. |
| 2004/0219520 A1 | 11/2004 | Mirkin et al. |
| 2004/0223876 A1 | 11/2004 | Kirollos et al. |
| 2004/0237631 A1 | 12/2004 | Cohen et al. |
| 2004/0242976 A1 | 12/2004 | Abreu |
| 2005/0000830 A1 | 1/2005 | Glatkowski et al. |
| 2005/0016276 A1 | 1/2005 | Guan et al. |
| 2005/0022581 A1 | 2/2005 | Sunshine |
| 2005/0037374 A1 | 2/2005 | Melker et al. |
| 2005/0048414 A1 | 3/2005 | Harnack et al. |
| 2005/0059030 A1 | 3/2005 | Bao et al. |
| 2005/0059031 A1 | 3/2005 | Bruchez et al. |
| 2005/0065230 A1 | 3/2005 | Huang |
| 2005/0072213 A1 | 4/2005 | Besnard et al. |
| 2005/0080322 A1 | 4/2005 | Korman |
| 2005/0080566 A1 | 4/2005 | Vock et al. |
| 2005/0090015 A1 | 4/2005 | Hartmann-Thompson |
| 2005/0119540 A1 | 6/2005 | Potts et al. |
| 2005/0121999 A1 | 6/2005 | Edmonson et al. |
| 2005/0126909 A1 | 6/2005 | Weiller et al. |
| 2005/0130174 A1 | 6/2005 | Bao et al. |
| 2005/0130240 A1 | 6/2005 | Lin et al. |
| 2005/0131139 A1 | 6/2005 | Kaner et al. |
| 2005/0148828 A1 | 7/2005 | Lindsay |
| 2005/0150778 A1 | 7/2005 | Lewis et al. |
| 2005/0159922 A1 | 7/2005 | Hsiung et al. |
| 2005/0176029 A1 | 8/2005 | Heller et al. |
| 2005/0177317 A1 | 8/2005 | Hsiung et al. |
| 2005/0194012 A1 | 9/2005 | Ito et al. |
| 2005/0195118 A1 | 9/2005 | Ito et al. |
| 2005/0202358 A1 | 9/2005 | Donnelly |
| 2005/0216114 A1 | 9/2005 | Hsiung et al. |
| 2005/0241935 A1 | 11/2005 | Lewis et al. |
| 2005/0244978 A1 | 11/2005 | Uluyol |
| 2005/0250094 A1 | 11/2005 | Storhoff et al. |
| 2005/0263394 A1 | 12/2005 | Lewis et al. |
| 2005/0272114 A1 | 12/2005 | Darzins et al. |
| 2005/0272881 A1 | 12/2005 | Blok |
| 2005/0280814 A1 | 12/2005 | Iuliano |
| 2005/0287552 A1 | 12/2005 | Lin et al. |
| 2006/0014172 A1 | 1/2006 | Muller et al. |
| 2006/0034731 A1 | 2/2006 | Lewis et al. |
| 2006/0040318 A1 | 2/2006 | Melker et al. |
| 2006/0052983 A1 | 3/2006 | Vock et al. |
| 2006/0053871 A1 | 3/2006 | Porter et al. |
| 2006/0057597 A1 | 3/2006 | Tai et al. |
| 2006/0057613 A1 | 3/2006 | Ramakrishnan et al. |
| 2006/0068378 A1 | 3/2006 | Mirkin et al. |
| 2006/0099113 A1 | 5/2006 | Lewis et al. |
| 2006/0099715 A1 | 5/2006 | Munoz et al. |
| 2006/0124195 A1 | 6/2006 | Cohen et al. |
| 2006/0124448 A1 | 6/2006 | Jayaraman et al. |
| 2006/0143645 A1 | 6/2006 | Vock et al. |
| 2006/0144123 A1 | 7/2006 | Sunshine |
| 2006/0174941 A1 | 8/2006 | Cohen et al. |
| 2006/0208254 A1 | 9/2006 | Goodman et al. |
| 2006/0244618 A1 | 11/2006 | Hotton et al. |
| 2006/0249385 A1 | 11/2006 | Stetter |
| 2006/0252999 A1 | 11/2006 | Devaul et al. |
| 2006/0253011 A1 | 11/2006 | Edmonson et al. |
| 2006/0254369 A1 | 11/2006 | Yoon et al. |
| 2006/0257883 A1 | 11/2006 | Bjoraker et al. |
| 2006/0259163 A1 | 11/2006 | Hsiung et al. |
| 2006/0270922 A1* | 11/2006 | Brauker ............... A61B 5/6848 600/345 |
| 2006/0275720 A1 | 12/2006 | Hotton et al. |
| 2006/0282225 A1 | 12/2006 | Sunshine et al. |
| 2006/0292033 A1 | 12/2006 | Blok et al. |
| 2006/0293714 A1 | 12/2006 | Salo et al. |
| 2007/0016096 A1 | 1/2007 | McNabb |
| 2007/0018779 A1 | 1/2007 | Sunshine et al. |
| 2007/0059763 A1 | 3/2007 | Okano et al. |
| 2007/0063850 A1 | 3/2007 | Devaul et al. |
| 2007/0087383 A1 | 4/2007 | Wu et al. |
| 2007/0087400 A1 | 4/2007 | Darzins et al. |
| 2007/0095678 A1 | 5/2007 | West et al. |
| 2007/0100666 A1 | 5/2007 | Stivoric et al. |
| 2007/0106138 A1 | 5/2007 | Beiski et al. |
| 2007/0111753 A1 | 5/2007 | Vock et al. |
| 2007/0112542 A1 | 5/2007 | Vock et al. |
| 2007/0114138 A1 | 5/2007 | Krasteva et al. |
| 2007/0117207 A1 | 5/2007 | West et al. |
| 2007/0118328 A1 | 5/2007 | Vock et al. |
| 2007/0119236 A1 | 5/2007 | Porter et al. |
| 2007/0122829 A1 | 5/2007 | Ballerstadt et al. |
| 2007/0125181 A1 | 6/2007 | Ofek et al. |
| 2007/0126061 A1 | 6/2007 | Dodabalapur et al. |
| 2007/0127164 A1 | 6/2007 | Ofek et al. |
| 2007/0131021 A1 | 6/2007 | Khadkikar et al. |
| 2007/0142799 A1 | 6/2007 | Ales et al. |
| 2007/0151449 A1 | 7/2007 | Wohltjen et al. |
| 2007/0152811 A1 | 7/2007 | Anderson |
| 2007/0154903 A1 | 7/2007 | Marla et al. |
| 2007/0173886 A1 | 7/2007 | Rousso et al. |
| 2007/0180892 A1 | 8/2007 | Sunshine |
| 2007/0187239 A1 | 8/2007 | Weiller et al. |

(56) References Cited

U.S. PATENT DOCUMENTS

| | | |
|---|---|---|
| 2007/0197878 A1 | 8/2007 | Shklarski |
| 2007/0197881 A1 | 8/2007 | Wolf et al. |
| 2007/0208542 A1 | 9/2007 | Vock et al. |
| 2007/0219434 A1 | 9/2007 | Abreu |
| 2007/0229294 A1 | 10/2007 | Vossmeyer et al. |
| 2007/0231947 A1 | 10/2007 | Joseph et al. |
| 2007/0235348 A1 | 10/2007 | Nagahara et al. |
| 2007/0252710 A1 | 11/2007 | Long et al. |
| 2007/0252711 A1 | 11/2007 | Long et al. |
| 2007/0255176 A1 | 11/2007 | Rondoni et al. |
| 2007/0258894 A1 | 11/2007 | Melker et al. |
| 2007/0269821 A1 | 11/2007 | Mazumdar et al. |
| 2007/0270672 A1 | 11/2007 | Hayter |
| 2007/0275690 A1 | 11/2007 | Hunter et al. |
| 2007/0298006 A1 | 12/2007 | Tomalia et al. |
| 2008/0003530 A1 | 1/2008 | Donnelly et al. |
| 2008/0017507 A1 | 1/2008 | Ramamurthy et al. |
| 2008/0025876 A1 | 1/2008 | Ramamurthy |
| 2008/0027679 A1 | 1/2008 | Shklarski |
| 2008/0030330 A1 | 2/2008 | Vock et al. |
| 2008/0054382 A1 | 3/2008 | Stetter |
| 2008/0077331 A1 | 3/2008 | Lewis et al. |
| 2008/0077440 A1 | 3/2008 | Doron |
| 2008/0081963 A1 | 4/2008 | Naghavi et al. |
| 2008/0091097 A1 | 4/2008 | Linti et al. |
| 2008/0101994 A1 | 5/2008 | Virji et al. |
| 2008/0103751 A1 | 5/2008 | Hsiung et al. |
| 2008/0146334 A1 | 6/2008 | Kil |
| 2008/0146701 A1 | 6/2008 | Sain et al. |
| 2008/0146892 A1 | 6/2008 | LeBoeuf et al. |
| 2008/0161654 A1 | 7/2008 | Teller et al. |
| 2008/0161655 A1 | 7/2008 | Teller et al. |
| 2008/0162088 A1 | 7/2008 | DeVaul et al. |
| 2008/0167535 A1 | 7/2008 | Stivoric et al. |
| 2008/0167536 A1 | 7/2008 | Teller et al. |
| 2008/0167537 A1 | 7/2008 | Teller et al. |
| 2008/0167538 A1 | 7/2008 | Teller et al. |
| 2008/0167539 A1 | 7/2008 | Teller et al. |
| 2008/0171919 A1 | 7/2008 | Stivoric et al. |
| 2008/0171920 A1 | 7/2008 | Teller et al. |
| 2008/0171921 A1 | 7/2008 | Teller et al. |
| 2008/0171922 A1 | 7/2008 | Teller et al. |
| 2008/0220535 A1 | 9/2008 | LeBoeuf et al. |
| 2008/0226995 A1 | 9/2008 | Costanzo et al. |
| 2008/0236251 A1 | 10/2008 | Tepper et al. |
| 2008/0241071 A1 | 10/2008 | West et al. |
| 2008/0241964 A1 | 10/2008 | Kaieda et al. |
| 2008/0245675 A1 | 10/2008 | Joseph et al. |
| 2008/0246629 A1 | 10/2008 | Tsui et al. |
| 2008/0262376 A1 | 10/2008 | Price |
| 2008/0262743 A1 | 10/2008 | Lewis et al. |
| 2008/0275309 A1 | 11/2008 | Stivoric et al. |
| 2008/0278140 A1 | 11/2008 | Dodabalapur et al. |
| 2008/0278181 A1 | 11/2008 | Zhong et al. |
| 2008/0279946 A1 | 11/2008 | Hainfeld |
| 2008/0287342 A1 | 11/2008 | Yu et al. |
| 2008/0287769 A1 | 11/2008 | Kurzweil et al. |
| 2008/0287770 A1 | 11/2008 | Kurzweil et al. |
| 2008/0294058 A1 | 11/2008 | Shklarski |
| 2008/0306357 A1 | 12/2008 | Korman |
| 2008/0318678 A1 | 12/2008 | Stivoric et al. |
| 2008/0319682 A1 | 12/2008 | Holland et al. |
| 2008/0319781 A1 | 12/2008 | Stivoric et al. |
| 2008/0319786 A1 | 12/2008 | Stivoric et al. |
| 2008/0319787 A1 | 12/2008 | Stivoric et al. |
| 2008/0319796 A1 | 12/2008 | Stivoric et al. |
| 2008/0319855 A1 | 12/2008 | Stivoric et al. |
| 2008/0320029 A1 | 12/2008 | Stivoric et al. |
| 2008/0320030 A1 | 12/2008 | Stivoric et al. |
| 2009/0004612 A1 | 1/2009 | West |
| 2009/0006457 A1 | 1/2009 | Stivoric et al. |
| 2009/0006458 A1 | 1/2009 | Stivoric et al. |
| 2009/0007636 A1 | 1/2009 | Starling |
| 2009/0007777 A1 | 1/2009 | Cohen et al. |
| 2009/0018412 A1 | 1/2009 | Schmitt |
| 2009/0042200 A1 | 2/2009 | Okano et al. |
| 2009/0042739 A1 | 2/2009 | Okano et al. |
| 2009/0049890 A1 | 2/2009 | Zhong et al. |
| 2009/0084162 A1 | 4/2009 | Besnard et al. |
| 2009/0090168 A1 | 4/2009 | Porter et al. |
| 2009/0093985 A1 | 4/2009 | Burdett et al. |
| 2009/0105605 A1 | 4/2009 | Abreu |
| 2009/0112071 A1 | 4/2009 | LeBoeuf et al. |
| 2009/0130421 A1 | 5/2009 | Ramamurthy |
| 2009/0130773 A1 | 5/2009 | Ayi et al. |
| 2009/0148690 A1 | 6/2009 | Krasteva et al. |
| 2009/0171166 A1 | 7/2009 | Amundson et al. |
| 2009/0174547 A1 | 7/2009 | Greene et al. |
| 2009/0177068 A1 | 7/2009 | Stivoric et al. |
| 2009/0196796 A1 | 8/2009 | Landini et al. |
| 2009/0201120 A1 | 8/2009 | Sunshine et al. |
| 2009/0212941 A1 | 8/2009 | Vock et al. |
| 2009/0214618 A1 | 8/2009 | Schoenfisch et al. |
| 2009/0214762 A1 | 8/2009 | Lewis et al. |
| 2009/0216461 A1 | 8/2009 | Sunshine et al. |
| 2009/0227059 A1 | 9/2009 | Besnard et al. |
| 2009/0234587 A1 | 9/2009 | Hsiung et al. |
| 2009/0246142 A1 | 10/2009 | Bhatia et al. |
| 2009/0256215 A1 | 10/2009 | Novak et al. |
| 2009/0260423 A1 | 10/2009 | Munoz et al. |
| 2009/0261987 A1 | 10/2009 | Sun |
| 2009/0263287 A1 | 10/2009 | Hartmann-Thompson |
| 2009/0269003 A1 | 10/2009 | Scully et al. |
| 2009/0273354 A1 | 11/2009 | Dhirani et al. |
| 2009/0294692 A1 | 12/2009 | Bourke, Jr. et al. |
| 2009/0309614 A1 | 12/2009 | Goodman et al. |
| 2009/0312615 A1 | 12/2009 | Caduff et al. |
| 2009/0315728 A1 | 12/2009 | Michael et al. |
| 2009/0322513 A1 | 12/2009 | Hwang et al. |
| 2009/0325215 A1 | 12/2009 | Okano et al. |
| 2009/0325812 A1 | 12/2009 | Mirkin et al. |
| 2010/0001211 A1 | 1/2010 | Huang et al. |
| 2010/0003316 A1 | 1/2010 | Vo Dinh et al. |
| 2010/0008619 A1 | 1/2010 | Sailor |
| 2010/0009872 A1 | 1/2010 | Eid et al. |
| 2010/0016568 A1 | 1/2010 | Okano et al. |
| 2010/0016569 A1 | 1/2010 | Okano et al. |
| 2010/0016783 A1 | 1/2010 | Bourke, Jr. et al. |
| 2010/0018862 A1 | 1/2010 | Okano et al. |
| 2010/0021933 A1 | 1/2010 | Okano et al. |
| 2010/0028559 A1 | 2/2010 | Yan et al. |
| 2010/0060465 A1 | 3/2010 | Stetter |
| 2010/0062232 A1 | 3/2010 | Schauer et al. |
| 2010/0069621 A1 | 3/2010 | Maune et al. |
| 2010/0073016 A1 | 3/2010 | Arora et al. |
| 2010/0076692 A1 | 3/2010 | Vock et al. |
| 2010/0081895 A1 | 4/2010 | Zand |
| 2010/0099957 A1 | 4/2010 | Wang |
| 2010/0102975 A1 | 4/2010 | Vossmeyer et al. |
| 2010/0121227 A1 | 5/2010 | Stirling et al. |
| 2010/0122832 A1 | 5/2010 | Bukshpun et al. |
| 2010/0132547 A1 | 6/2010 | Masel et al. |
| 2010/0140597 A1 | 6/2010 | Babudri et al. |
| 2010/0152621 A1 | 6/2010 | Janna et al. |
| 2010/0176952 A1 | 7/2010 | Bajcsy et al. |
| 2010/0188110 A1 | 7/2010 | Sun |
| 2010/0191474 A1 | 7/2010 | Haick |
| 2010/0196920 A1 | 8/2010 | Lee et al. |
| 2010/0203648 A1 | 8/2010 | Porter et al. |
| 2010/0204676 A1 | 8/2010 | Cardullo |
| 2010/0209301 A1 | 8/2010 | Hartmann-Thompson |
| 2010/0217099 A1 | 8/2010 | LeBoeuf et al. |
| 2010/0225337 A1 | 9/2010 | Zamborini et al. |
| 2010/0229658 A1 | 9/2010 | Glezer et al. |
| 2010/0234579 A1 | 9/2010 | Mirkin et al. |
| 2010/0240962 A1 | 9/2010 | Contant |
| 2010/0241464 A1 | 9/2010 | Amigo et al. |
| 2010/0241465 A1 | 9/2010 | Amigo et al. |
| 2010/0249557 A1 | 9/2010 | Besko et al. |
| 2010/0261263 A1 | 10/2010 | Vo-Dinh et al. |
| 2010/0272612 A1 | 10/2010 | Ramamurthy |
| 2010/0273665 A1 | 10/2010 | Haick et al. |
| 2010/0276302 A1 | 11/2010 | Raguse et al. |
| 2010/0286532 A1 | 11/2010 | Farringdon et al. |

(56) References Cited

U.S. PATENT DOCUMENTS

| | | |
|---|---|---|
| 2010/0290992 A1 | 11/2010 | Seela et al. |
| 2011/0003610 A1 | 1/2011 | Key et al. |
| 2011/0004072 A1 | 1/2011 | Fletcher et al. |
| 2011/0010107 A1 | 1/2011 | Fedder et al. |
| 2011/0012096 A1 | 1/2011 | Carmeli et al. |
| 2011/0015872 A1 | 1/2011 | Haick et al. |
| 2011/0021970 A1 | 1/2011 | Vo-Dinh et al. |
| 2011/0034912 A1 | 2/2011 | De Graff et al. |
| 2011/0035190 A1 | 2/2011 | DeVaul et al. |
| 2011/0054202 A1 | 3/2011 | Snow |
| 2011/0054359 A1 | 3/2011 | Sazonov et al. |
| 2011/0065807 A1 | 3/2011 | Radovic-Moreno et al. |
| 2011/0070835 A1 | 3/2011 | Borras et al. |
| 2011/0081724 A1 | 4/2011 | Swager et al. |
| 2011/0082484 A1 | 4/2011 | Saravia et al. |
| 2011/0089051 A1 | 4/2011 | Wang et al. |
| 2011/0092825 A1 | 4/2011 | Gopinathan et al. |
| 2011/0098112 A1 | 4/2011 | LeBoeuf et al. |
| 2011/0098197 A1 | 4/2011 | Chung et al. |
| 2011/0098591 A1 | 4/2011 | Haick et al. |
| 2011/0106627 A1 | 5/2011 | LeBoeuf et al. |
| 2011/0114244 A1 | 5/2011 | Yoo et al. |
| 2011/0114511 A1 | 5/2011 | Sjong |
| 2011/0125409 A1 | 5/2011 | Hsiung et al. |
| 2011/0127446 A1 | 6/2011 | Star et al. |
| 2011/0129537 A1 | 6/2011 | Vo-Dinh et al. |
| 2011/0136139 A1 | 6/2011 | Bruchez et al. |
| 2011/0145162 A1 | 6/2011 | Vock et al. |
| 2011/0171137 A1 | 7/2011 | Patolsky et al. |
| 2011/0171749 A1 | 7/2011 | Alocilja et al. |
| 2011/0176130 A1 | 7/2011 | Gu et al. |
| 2011/0184649 A1 | 7/2011 | Ofek |
| 2011/0191044 A1 | 8/2011 | Stafford |
| 2011/0206740 A1 | 8/2011 | Karp et al. |
| 2011/0213225 A1 | 9/2011 | Bernstein et al. |
| 2011/0213271 A1 | 9/2011 | Telfort et al. |
| 2011/0213272 A1 | 9/2011 | Telfort et al. |
| 2011/0213273 A1 | 9/2011 | Telfort et al. |
| 2011/0213274 A1 | 9/2011 | Telfort et al. |
| 2011/0223583 A1 | 9/2011 | Gordon et al. |
| 2011/0244584 A1 | 10/2011 | Haick et al. |
| 2011/0246086 A1 | 10/2011 | Huang et al. |
| 2011/0263920 A1 | 10/2011 | Bourke, Jr. et al. |
| 2011/0269632 A1 | 11/2011 | Haick et al. |
| 2011/0282828 A1 | 11/2011 | Precup et al. |
| 2011/0286889 A1 | 11/2011 | Ramamurthy et al. |
| 2011/0288574 A1 | 11/2011 | Curry et al. |
| 2011/0298613 A1 | 12/2011 | Ben Ayed |
| 2011/0300637 A1 | 12/2011 | Virji et al. |
| 2011/0319729 A1 | 12/2011 | Donnay et al. |
| 2011/0320136 A1 | 12/2011 | Sunshine et al. |
| 2012/0010642 A1 | 1/2012 | Lee et al. |
| 2012/0020033 A1 | 1/2012 | Pilditch et al. |
| 2012/0021055 A1 | 1/2012 | Schoenfisch et al. |
| 2012/0034169 A1 | 2/2012 | Schoenfisch et al. |
| 2012/0041574 A1 | 2/2012 | Hsiung et al. |
| 2012/0050038 A1 | 3/2012 | Stetter |
| 2012/0056632 A1 | 3/2012 | Dhirani et al. |
| 2012/0064134 A1 | 3/2012 | Bourke, Jr. et al. |
| 2012/0070376 A1 | 3/2012 | Ostroff et al. |
| 2012/0071362 A1 | 3/2012 | Nhan et al. |
| 2012/0071737 A1 | 3/2012 | Landini et al. |
| 2012/0075168 A1 | 3/2012 | Osterhout et al. |
| 2012/0087949 A1 | 4/2012 | Tan et al. |
| 2012/0090378 A1 | 4/2012 | Wang et al. |
| 2012/0095352 A1 | 4/2012 | Tran |
| 2012/0097917 A1 | 4/2012 | Zhou et al. |
| 2012/0123232 A1 | 5/2012 | Najarian et al. |
| 2012/0123960 A1 | 5/2012 | Vock et al. |
| 2012/0135437 A1 | 5/2012 | Brennan et al. |
| 2012/0143495 A1 | 6/2012 | Dantu |
| 2012/0143514 A1 | 6/2012 | Vock et al. |
| 2012/0143515 A1 | 6/2012 | Norman et al. |
| 2012/0146784 A1 | 6/2012 | Hines et al. |
| 2012/0149996 A1 | 6/2012 | Stivoric et al. |
| 2012/0150483 A1 | 6/2012 | Vock et al. |
| 2012/0156099 A1 | 6/2012 | Zhong et al. |
| 2012/0156135 A1 | 6/2012 | Farokhzad et al. |
| 2012/0157793 A1 | 6/2012 | MacDonald |
| 2012/0165617 A1 | 6/2012 | Vesto et al. |
| 2012/0165623 A1 | 6/2012 | Lynn et al. |
| 2012/0172783 A1 | 7/2012 | Harris et al. |
| 2012/0172792 A1 | 7/2012 | Baynham et al. |
| 2012/0186987 A1 | 7/2012 | Mirsky et al. |
| 2012/0190941 A1 | 7/2012 | Donnay et al. |
| 2012/0190942 A1 | 7/2012 | Donnay et al. |
| 2012/0190943 A1 | 7/2012 | Donnay et al. |
| 2012/0190951 A1 | 7/2012 | Curry et al. |
| 2012/0194418 A1 | 8/2012 | Osterhout et al. |
| 2012/0194419 A1 | 8/2012 | Osterhout et al. |
| 2012/0194420 A1 | 8/2012 | Osterhout et al. |
| 2012/0194549 A1 | 8/2012 | Osterhout et al. |
| 2012/0194550 A1 | 8/2012 | Osterhout et al. |
| 2012/0194551 A1 | 8/2012 | Osterhout et al. |
| 2012/0194552 A1 | 8/2012 | Osterhout et al. |
| 2012/0194553 A1 | 8/2012 | Osterhout et al. |
| 2012/0197093 A1 | 8/2012 | LeBoeuf et al. |
| 2012/0197098 A1 | 8/2012 | Donnay et al. |
| 2012/0197222 A1 | 8/2012 | Donnay et al. |
| 2012/0197737 A1 | 8/2012 | LeBoeuf et al. |
| 2012/0200488 A1 | 8/2012 | Osterhout et al. |
| 2012/0200499 A1 | 8/2012 | Osterhout et al. |
| 2012/0200601 A1 | 8/2012 | Osterhout et al. |
| 2012/0203081 A1 | 8/2012 | LeBoeuf et al. |
| 2012/0203453 A1 | 8/2012 | Lundquist et al. |
| 2012/0203491 A1 | 8/2012 | Sun et al. |
| 2012/0203511 A1 | 8/2012 | DeVaul et al. |
| 2012/0206322 A1 | 8/2012 | Osterhout et al. |
| 2012/0206323 A1 | 8/2012 | Osterhout et al. |
| 2012/0206334 A1 | 8/2012 | Osterhout et al. |
| 2012/0206335 A1 | 8/2012 | Osterhout et al. |
| 2012/0206485 A1 | 8/2012 | Osterhout et al. |
| 2012/0209088 A1 | 8/2012 | Romem |
| 2012/0212242 A1 | 8/2012 | Masel et al. |
| 2012/0212398 A1 | 8/2012 | Border et al. |
| 2012/0212399 A1 | 8/2012 | Border et al. |
| 2012/0212400 A1 | 8/2012 | Border et al. |
| 2012/0212406 A1 | 8/2012 | Osterhout et al. |
| 2012/0212414 A1 | 8/2012 | Osterhout et al. |
| 2012/0212484 A1 | 8/2012 | Haddick et al. |
| 2012/0212499 A1 | 8/2012 | Haddick et al. |
| 2012/0215076 A1 | 8/2012 | Yang et al. |
| 2012/0218172 A1 | 8/2012 | Border et al. |
| 2012/0218301 A1 | 8/2012 | Miller |
| 2012/0226111 A1 | 9/2012 | LeBoeuf et al. |
| 2012/0226112 A1 | 9/2012 | LeBoeuf et al. |
| 2012/0226130 A1 | 9/2012 | De Graff et al. |
| 2012/0229661 A1 | 9/2012 | Sekiguchi et al. |
| 2012/0235883 A1 | 9/2012 | Border et al. |
| 2012/0235884 A1 | 9/2012 | Miller et al. |
| 2012/0235885 A1 | 9/2012 | Miller et al. |
| 2012/0235886 A1 | 9/2012 | Border et al. |
| 2012/0235887 A1 | 9/2012 | Border et al. |
| 2012/0235900 A1 | 9/2012 | Border et al. |
| 2012/0236030 A1 | 9/2012 | Border et al. |
| 2012/0236031 A1 | 9/2012 | Haddick et al. |
| 2012/0242678 A1 | 9/2012 | Border et al. |
| 2012/0242697 A1 | 9/2012 | Border et al. |
| 2012/0242698 A1 | 9/2012 | Haddick et al. |
| 2012/0244807 A1 | 9/2012 | Kuroda |
| 2012/0245439 A1 | 9/2012 | Andre et al. |
| 2012/0245447 A1 | 9/2012 | Karan et al. |
| 2012/0246788 A1 | 10/2012 | Harrell et al. |
| 2012/0249797 A1 | 10/2012 | Haddick et al. |
| 2012/0263648 A1 | 10/2012 | Shapiro et al. |
| 2012/0263793 A1 | 10/2012 | Vitaliano |
| 2012/0265296 A1 | 10/2012 | McNamara et al. |
| 2012/0265477 A1 | 10/2012 | Vock et al. |
| 2012/0270205 A1 | 10/2012 | Patel et al. |
| 2012/0273354 A1 | 11/2012 | Orhan et al. |
| 2012/0277546 A1 | 11/2012 | Soykan et al. |
| 2012/0282594 A1 | 11/2012 | Chen et al. |
| 2012/0283577 A1 | 11/2012 | LeBoeuf et al. |
| 2012/0283578 A1 | 11/2012 | LeBoeuf et al. |

(56) References Cited

U.S. PATENT DOCUMENTS

| | | |
|---|---|---|
| 2012/0295360 A1 | 11/2012 | Swager et al. |
| 2012/0296175 A1 | 11/2012 | Poh et al. |
| 2012/0296184 A1 | 11/2012 | LeBoeuf et al. |
| 2012/0296191 A1 | 11/2012 | McGrath et al. |
| 2012/0301360 A1 | 11/2012 | Meinhold et al. |
| 2012/0315322 A1 | 12/2012 | Chakravarthy et al. |
| 2013/0013333 A1 | 1/2013 | Gopinathan et al. |
| 2013/0022755 A1 | 1/2013 | D'Arcy |
| 2013/0023714 A1 | 1/2013 | Johnston et al. |
| 2013/0030711 A1 | 1/2013 | Korhonen |
| 2013/0034599 A1 | 2/2013 | Thaxton et al. |
| 2013/0034915 A1 | 2/2013 | Ballerstadt et al. |
| 2013/0040399 A1 | 2/2013 | BelBruno et al. |
| 2013/0046485 A1 | 2/2013 | Norman et al. |
| 2013/0057720 A1 | 3/2013 | Kawaji et al. |
| 2013/0059396 A1 | 3/2013 | LeBoeuf et al. |
| 2013/0059758 A1 | 3/2013 | Haick et al. |
| 2013/0060480 A1 | 3/2013 | Korhonen et al. |
| 2013/0065319 A1 | 3/2013 | Zang et al. |
| 2013/0066168 A1 | 3/2013 | Yang et al. |
| 2013/0066395 A1 | 3/2013 | Simon et al. |
| 2013/0095499 A1 | 4/2013 | Rose-Petruck et al. |
| 2013/0096396 A1 | 4/2013 | Riedel |
| 2013/0096466 A1 | 4/2013 | Sarrafzadeh et al. |
| 2013/0103416 A1 | 4/2013 | Amigo et al. |
| 2013/0116405 A1 | 5/2013 | Yu et al. |
| 2013/0124039 A1 | 5/2013 | Abreu |
| 2013/0126363 A1 | 5/2013 | Raguse et al. |
| 2013/0127980 A1 | 5/2013 | Haddick et al. |
| 2013/0131519 A1 | 5/2013 | LeBoeuf et al. |
| 2013/0140649 A1 | 6/2013 | Rogers et al. |
| 2013/0143247 A1 | 6/2013 | Haick et al. |
| 2013/0144564 A1 | 6/2013 | DeVaul et al. |
| 2013/0151699 A1 | 6/2013 | Vock et al. |
| 2013/0156905 A1 | 6/2013 | Bourke, Jr. et al. |
| 2013/0158881 A1 | 6/2013 | Sunshine et al. |
| 2013/0162403 A1 | 6/2013 | Striemer et al. |
| 2013/0171060 A1 | 7/2013 | Vo-Dinh et al. |
| 2013/0171733 A1 | 7/2013 | Haick et al. |
| 2013/0172691 A1 | 7/2013 | Tran |
| 2013/0177598 A1 | 7/2013 | Desimone et al. |
| 2013/0183243 A1 | 7/2013 | LaBelle et al. |
| 2013/0183766 A1 | 7/2013 | Zang et al. |
| 2013/0196872 A1 | 8/2013 | Low et al. |
| 2013/0197319 A1 | 8/2013 | Monty et al. |
| 2013/0203073 A1 | 8/2013 | Mager et al. |
| 2013/0210023 A1 | 8/2013 | Tanner et al. |
| 2013/0210679 A1 | 8/2013 | Joseph et al. |
| 2013/0211788 A1 | 8/2013 | Sicurello et al. |
| 2013/0216989 A1 | 8/2013 | Cuthbert |
| 2013/0234724 A1 | 9/2013 | Kabasawa et al. |
| 2013/0236980 A1 | 9/2013 | Moretti et al. |
| 2013/0236981 A1 | 9/2013 | Haick et al. |
| 2013/0238276 A1 | 9/2013 | Vock et al. |
| 2013/0240758 A1 | 9/2013 | Bourke, Jr. et al. |
| 2013/0241726 A1 | 9/2013 | Hunter et al. |
| 2013/0245388 A1 | 9/2013 | Rafferty et al. |
| 2013/0245486 A1 | 9/2013 | Simon et al. |
| 2013/0252843 A1 | 9/2013 | Yan et al. |
| 2013/0252848 A1 | 9/2013 | Okano et al. |
| 2013/0259749 A1 | 10/2013 | Moretti et al. |
| 2013/0261010 A1 | 10/2013 | Bailey et al. |
| 2013/0274642 A1 | 10/2013 | Soykan et al. |
| 2013/0278631 A1 | 10/2013 | Border et al. |
| 2013/0288777 A1 | 10/2013 | Short et al. |
| 2013/0295688 A1 | 11/2013 | Bailey et al. |
| 2013/0311084 A1 | 11/2013 | Lundquist et al. |
| 2013/0311108 A1 | 11/2013 | Stetter et al. |
| 2013/0314303 A1 | 11/2013 | Osterhout et al. |
| 2013/0315816 A1 | 11/2013 | Watson et al. |
| 2013/0330231 A1 | 12/2013 | Swager et al. |
| 2013/0338470 A1 | 12/2013 | Ouwerkerk |
| 2013/0338768 A1 | 12/2013 | Boyden et al. |
| 2013/0338769 A1 | 12/2013 | Boyden et al. |
| 2013/0338770 A1 | 12/2013 | Boyden et al. |
| 2013/0338771 A1 | 12/2013 | Boyden et al. |
| 2013/0338772 A1 | 12/2013 | Boyden et al. |
| 2013/0338773 A1 | 12/2013 | Boyden et al. |
| 2013/0346148 A1 | 12/2013 | Roth et al. |
| 2014/0005426 A1 | 1/2014 | Schoenfisch et al. |
| 2014/0012105 A1 | 1/2014 | LeBoeuf et al. |
| 2014/0012145 A1 | 1/2014 | Kurzweil et al. |
| 2014/0015548 A1 | 1/2014 | Naughton et al. |
| 2014/0018638 A1 | 1/2014 | Chatterjee |
| 2014/0022058 A1 | 1/2014 | Striemer et al. |
| 2014/0024026 A1 | 1/2014 | Alocilja et al. |
| 2014/0031705 A1 | 1/2014 | Kurzweil et al. |
| 2014/0039290 A1 | 2/2014 | Graff et al. |
| 2014/0050793 A1 | 2/2014 | Chaiken et al. |
| 2014/0051946 A1 | 2/2014 | Arne et al. |
| 2014/0052567 A1 | 2/2014 | Bhardwaj et al. |
| 2014/0058124 A1 | 2/2014 | Schoenfisch et al. |
| 2014/0058272 A1 | 2/2014 | Naing et al. |
| 2014/0063054 A1 | 3/2014 | Osterhout et al. |
| 2014/0063055 A1 | 3/2014 | Osterhout et al. |
| 2014/0081175 A1 | 3/2014 | Telfort |
| 2014/0081578 A1 | 3/2014 | Connor |
| 2014/0081667 A1 | 3/2014 | Joao |
| 2014/0083869 A1 | 3/2014 | Manohar et al. |
| 2014/0088442 A1 | 3/2014 | Soykan et al. |
| 2014/0091811 A1 | 4/2014 | Potyrailo et al. |
| 2014/0094136 A1 | 4/2014 | Huang |
| 2014/0095102 A1 | 4/2014 | Potyrailo et al. |
| 2014/0106816 A1 | 4/2014 | Shimuta |
| 2014/0107362 A1 | 4/2014 | Snow |
| 2014/0107495 A1 | 4/2014 | Marinelli et al. |
| 2014/0107498 A1 | 4/2014 | Bower et al. |
| 2014/0107932 A1 | 4/2014 | Luna |
| 2014/0114699 A1 | 4/2014 | Amigo et al. |
| 2014/0115008 A1 | 4/2014 | Stivoric et al. |
| 2014/0120534 A1 | 5/2014 | Bernitz et al. |
| 2014/0122496 A1 | 5/2014 | Stivoric et al. |
| 2014/0122536 A1 | 5/2014 | Stivoric et al. |
| 2014/0122537 A1 | 5/2014 | Stivoric et al. |
| 2014/0127822 A1 | 5/2014 | Arora et al. |
| 2014/0143064 A1 | 5/2014 | Tran |
| 2014/0145736 A1 | 5/2014 | Myung et al. |
| 2014/0151631 A1 | 6/2014 | Duesberg et al. |
| 2014/0156698 A1 | 6/2014 | Stivoric et al. |
| 2014/0163303 A1 | 6/2014 | Bourke, Jr. et al. |
| 2014/0172358 A1 | 6/2014 | Vock et al. |
| 2014/0180018 A1 | 6/2014 | Stivoric et al. |
| 2014/0180024 A1 | 6/2014 | Stivoric et al. |
| 2014/0180025 A1 | 6/2014 | Stivoric et al. |
| 2014/0180598 A1 | 6/2014 | Stivoric et al. |
| 2014/0180720 A1 | 6/2014 | Stivoric et al. |
| 2014/0180993 A1 | 6/2014 | Stivoric et al. |
| 2014/0181108 A1 | 6/2014 | Stivoric et al. |
| 2014/0187872 A1 | 7/2014 | Stivoric et al. |
| 2014/0187873 A1 | 7/2014 | Stivoric et al. |
| 2014/0188874 A1 | 7/2014 | Stivoric et al. |
| 2014/0193925 A1 | 7/2014 | Bhattacharyya et al. |
| 2014/0197947 A1 | 7/2014 | Bahorich |
| 2014/0200426 A1 | 7/2014 | Taub et al. |
| 2014/0200432 A1 | 7/2014 | Banerji et al. |
| 2014/0202264 A1 | 7/2014 | Vock et al. |
| 2014/0203797 A1 | 7/2014 | Stivoric et al. |
| 2014/0203972 A1 | 7/2014 | Vock et al. |
| 2014/0206948 A1 | 7/2014 | Romem |
| 2014/0206955 A1 | 7/2014 | Stivoric et al. |
| 2014/0208828 A1 | 7/2014 | Von Waldkirch |
| 2014/0213854 A1 | 7/2014 | Stivoric et al. |
| 2014/0213855 A1 | 7/2014 | Teller et al. |
| 2014/0213856 A1 | 7/2014 | Teller et al. |
| 2014/0213857 A1 | 7/2014 | Teller et al. |
| 2014/0213938 A1 | 7/2014 | Stivoric et al. |
| 2014/0214552 A1 | 7/2014 | Stivoric et al. |
| 2014/0214836 A1 | 7/2014 | Stivoric et al. |
| 2014/0214873 A1 | 7/2014 | Stivoric et al. |
| 2014/0214874 A1 | 7/2014 | Stivoric et al. |
| 2014/0214903 A1 | 7/2014 | Stivoric et al. |
| 2014/0220525 A1 | 8/2014 | Stivoric et al. |
| 2014/0220703 A1 | 8/2014 | Patel et al. |
| 2014/0221730 A1 | 8/2014 | Stivoric et al. |

(56) References Cited

U.S. PATENT DOCUMENTS

| | | |
|---|---|---|
| 2014/0221769 A1 | 8/2014 | Teller et al. |
| 2014/0221770 A1 | 8/2014 | Teller et al. |
| 2014/0221773 A1 | 8/2014 | Stivoric et al. |
| 2014/0221774 A1 | 8/2014 | Teller et al. |
| 2014/0221775 A1 | 8/2014 | Stivoric et al. |
| 2014/0221776 A1 | 8/2014 | Stivoric et al. |
| 2014/0221849 A1 | 8/2014 | Farringdon et al. |
| 2014/0221850 A1 | 8/2014 | Farringdon et al. |
| 2014/0222117 A1 | 8/2014 | Bourke, Jr. et al. |
| 2014/0222174 A1 | 8/2014 | Teller et al. |
| 2014/0222732 A1 | 8/2014 | Stivoric et al. |
| 2014/0222733 A1 | 8/2014 | Stivoric et al. |
| 2014/0222734 A1 | 8/2014 | Stivoric et al. |
| 2014/0222735 A1 | 8/2014 | Stivoric et al. |
| 2014/0222804 A1 | 8/2014 | Stivoric et al. |
| 2014/0222847 A1 | 8/2014 | Stivoric et al. |
| 2014/0222848 A1 | 8/2014 | Stivoric et al. |
| 2014/0222849 A1 | 8/2014 | Stivoric et al. |
| 2014/0222850 A1 | 8/2014 | Stivoric et al. |
| 2014/0222851 A1 | 8/2014 | Stivoric et al. |
| 2014/0223406 A1 | 8/2014 | Teller et al. |
| 2014/0223407 A1 | 8/2014 | Teller et al. |
| 2014/0223421 A1 | 8/2014 | Carter et al. |
| 2014/0232516 A1 | 8/2014 | Stivoric et al. |
| 2014/0242237 A1 | 8/2014 | Belbruno et al. |
| 2014/0243934 A1 | 8/2014 | Vo-Dinh et al. |
| 2014/0249381 A1 | 9/2014 | LeBoeuf et al. |
| 2014/0249763 A1 | 9/2014 | Shimuta |
| 2014/0267299 A1 | 9/2014 | Couse |
| 2014/0273029 A1 | 9/2014 | Bailey et al. |
| 2014/0274216 A1 | 9/2014 | Olodort |
| 2014/0274804 A1 | 9/2014 | Thomas et al. |
| 2014/0275716 A1 | 9/2014 | Connor |
| 2014/0275824 A1 | 9/2014 | Couse |
| 2014/0275828 A1 | 9/2014 | Osorio |
| 2014/0275838 A1 | 9/2014 | Osorio |
| 2014/0275840 A1 | 9/2014 | Osorio |
| 2014/0275855 A1 | 9/2014 | LeBoeuf et al. |
| 2014/0275898 A1 | 9/2014 | Taub et al. |
| 2014/0277649 A1 | 9/2014 | Chong et al. |
| 2014/0285402 A1 | 9/2014 | Rahman et al. |
| 2014/0287833 A1 | 9/2014 | LeBoeuf et al. |
| 2014/0288394 A1 | 9/2014 | LeBoeuf et al. |
| 2014/0288396 A1 | 9/2014 | LeBoeuf et al. |
| 2014/0288647 A1 | 9/2014 | Boyden et al. |
| 2014/0294927 A1 | 10/2014 | Thaxton et al. |
| 2014/0296663 A1 | 10/2014 | Boyden et al. |
| 2014/0296978 A1 | 10/2014 | Boyden et al. |
| 2014/0303452 A1 | 10/2014 | Ghaffari |
| 2014/0303508 A1 | 10/2014 | Plotnik-Peleg et al. |
| 2014/0303520 A1 | 10/2014 | Telfort et al. |
| 2014/0306814 A1 | 10/2014 | Ricci |
| 2014/0306834 A1 | 10/2014 | Ricci |
| 2014/0306835 A1 | 10/2014 | Ricci |
| 2014/0308636 A1 | 10/2014 | Stivoric et al. |
| 2014/0308639 A1 | 10/2014 | Stivoric et al. |
| 2014/0308902 A1 | 10/2014 | Ricci |
| 2014/0309838 A1 | 10/2014 | Ricci |
| 2014/0309919 A1 | 10/2014 | Ricci |
| 2014/0309930 A1 | 10/2014 | Ricci |
| 2014/0309939 A1 | 10/2014 | Stivoric et al. |
| 2014/0309940 A1 | 10/2014 | Stivoric et al. |
| 2014/0310105 A1 | 10/2014 | Stivoric et al. |
| 2014/0310223 A1 | 10/2014 | Stivoric et al. |
| 2014/0310274 A1 | 10/2014 | Stivoric et al. |
| 2014/0310275 A1 | 10/2014 | Stivoric et al. |
| 2014/0310276 A1 | 10/2014 | Stivoric et al. |
| 2014/0310284 A1 | 10/2014 | Stivoric et al. |
| 2014/0310294 A1 | 10/2014 | Stivoric et al. |
| 2014/0310295 A1 | 10/2014 | Stivoric et al. |
| 2014/0310296 A1 | 10/2014 | Stivoric et al. |
| 2014/0310297 A1 | 10/2014 | Stivoric et al. |
| 2014/0310298 A1 | 10/2014 | Stivoric et al. |
| 2014/0310379 A1 | 10/2014 | Ricci et al. |
| 2014/0310702 A1 | 10/2014 | Ricci et al. |
| 2014/0316229 A1 | 10/2014 | Tognetti et al. |
| 2014/0316885 A1 | 10/2014 | Stivoric et al. |
| 2014/0317039 A1 | 10/2014 | Stivoric et al. |
| 2014/0317042 A1 | 10/2014 | Stivoric et al. |
| 2014/0317119 A1 | 10/2014 | Stivoric et al. |
| 2014/0317135 A1 | 10/2014 | Stivoric et al. |
| 2014/0318990 A1 | 10/2014 | Star |
| 2014/0322823 A1 | 10/2014 | Alocilja et al. |
| 2014/0330043 A1 | 11/2014 | Snow |
| 2014/0335154 A1 | 11/2014 | Bot |
| 2014/0343370 A1 | 11/2014 | Stivoric et al. |
| 2014/0343371 A1 | 11/2014 | Skerik et al. |
| 2014/0343380 A1 | 11/2014 | Carter et al. |
| 2014/0343479 A1 | 11/2014 | Bourke et al. |
| 2014/0344208 A1 | 11/2014 | Ghasemzadeh et al. |
| 2014/0344282 A1 | 11/2014 | Stivoric et al. |
| 2014/0347187 A1 | 11/2014 | Freathey |
| 2014/0347491 A1 | 11/2014 | Connor |
| 2014/0349256 A1 | 11/2014 | Connor |
| 2014/0349257 A1 | 11/2014 | Connor |
| 2014/0350883 A1 | 11/2014 | Carter et al. |
| 2014/0363833 A1 | 12/2014 | Bhatia et al. |
| 2014/0364332 A1 | 12/2014 | Mehra et al. |
| 2014/0368643 A1 | 12/2014 | Siegel et al. |
| 2014/0371105 A1 | 12/2014 | Thomas et al. |
| 2014/0378676 A1 | 12/2014 | Lauraeus et al. |
| 2014/0378853 A1 | 12/2014 | McKinney et al. |
| 2015/0005188 A1 | 1/2015 | Levner et al. |
| 2015/0005680 A1 | 1/2015 | Lipani |
| 2015/0017258 A1 | 1/2015 | Azzazy et al. |
| 2015/0025338 A1 | 1/2015 | Lee et al. |
| 2015/0031571 A1 | 1/2015 | Wu et al. |
| 2015/0031967 A1 | 1/2015 | LeBoeuf et al. |
| 2015/0032505 A1 | 1/2015 | Kusukame et al. |
| 2015/0038874 A1 | 2/2015 | Abreu |
| 2015/0047091 A1 | 2/2015 | Fournier et al. |
| 2015/0054628 A1 | 2/2015 | Roth |
| 2015/0056627 A1 | 2/2015 | Karkkainen et al. |
| 2015/0057512 A1 | 2/2015 | Kapoor |
| 2015/0057515 A1* | 2/2015 | Hagen .............. G01N 27/3273 600/346 |
| 2015/0057516 A1 | 2/2015 | Mujeeb-U-Rahman et al. |
| 2015/0058110 A1 | 2/2015 | Roth |
| 2015/0058133 A1 | 2/2015 | Roth et al. |
| 2015/0061895 A1 | 3/2015 | Ricci |
| 2015/0063202 A1 | 3/2015 | Mazzarella et al. |
| 2015/0076007 A1 | 3/2015 | Compton et al. |
| 2015/0078140 A1 | 3/2015 | Riobo Aboy et al. |
| 2015/0079697 A1 | 3/2015 | Belbruno et al. |
| 2015/0080741 A1 | 3/2015 | LeBoeuf et al. |
| 2015/0080746 A1 | 3/2015 | Bleich et al. |
| 2015/0082920 A1 | 3/2015 | Haick et al. |
| 2015/0087935 A1 | 3/2015 | Davis et al. |
| 2015/0088007 A1 | 3/2015 | Bardy et al. |
| 2015/0093725 A1 | 4/2015 | Baarman et al. |
| 2015/0093774 A1 | 4/2015 | Tore et al. |
| 2015/0094914 A1 | 4/2015 | Abreu |
| 2015/0101392 A1 | 4/2015 | Foote |
| 2015/0102208 A1 | 4/2015 | Appelboom et al. |
| 2015/0111088 A1 | 4/2015 | Hiroki et al. |
| 2015/0111308 A1 | 4/2015 | Yu et al. |
| 2015/0112164 A1 | 4/2015 | Heikenfeld et al. |
| 2015/0112165 A1 | 4/2015 | Heikenfeld |
| 2015/0116093 A1 | 4/2015 | Swager et al. |
| 2015/0119657 A1 | 4/2015 | LeBoeuf et al. |
| 2015/0123641 A1 | 5/2015 | Dalton et al. |
| 2015/0126824 A1 | 5/2015 | LeBoeuf et al. |
| 2015/0126873 A1 | 5/2015 | Connor |
| 2015/0132857 A1 | 5/2015 | Belbruno et al. |
| 2015/0140397 A1 | 5/2015 | Tajima et al. |
| 2015/0141266 A1 | 5/2015 | Turner et al. |
| 2015/0141772 A1 | 5/2015 | LeBoeuf et al. |
| 2015/0145676 A1 | 5/2015 | Adhikari et al. |
| 2015/0148623 A1 | 5/2015 | Benaron |
| 2015/0148624 A1 | 5/2015 | Benaron |
| 2015/0148625 A1 | 5/2015 | Benaron |
| 2015/0148628 A1 | 5/2015 | Abreu |
| 2015/0148632 A1 | 5/2015 | Benaron |
| 2015/0148635 A1 | 5/2015 | Benaron |

(56) References Cited

U.S. PATENT DOCUMENTS

| | | |
|---|---|---|
| 2015/0148636 A1 | 5/2015 | Benaron |
| 2015/0148681 A1 | 5/2015 | Abreu |
| 2015/0150453 A1 | 6/2015 | Abreu |
| 2015/0150467 A1 | 6/2015 | Abreu |
| 2015/0157220 A1 | 6/2015 | Fish et al. |
| 2015/0164117 A1 | 6/2015 | Kaplan et al. |
| 2015/0164238 A1 | 6/2015 | Benson et al. |
| 2015/0164404 A1 | 6/2015 | Euliano et al. |
| 2015/0164409 A1 | 6/2015 | Benson et al. |
| 2015/0168365 A1 | 6/2015 | Connor |
| 2015/0170540 A1 | 6/2015 | Ford |
| 2015/0173674 A1 | 6/2015 | Hayes et al. |
| 2015/0178915 A1 | 6/2015 | Chatterjee et al. |
| 2015/0181840 A1 | 7/2015 | Tupin, Jr. et al. |
| 2015/0182322 A1 | 7/2015 | Couse et al. |
| 2015/0182543 A1 | 7/2015 | Schoenfisch et al. |
| 2015/0182843 A1 | 7/2015 | Esposito et al. |
| 2015/0185088 A1 | 7/2015 | Rabieirad et al. |
| 2015/0198606 A1 | 7/2015 | Bruchez et al. |
| 2015/0199010 A1 | 7/2015 | Coleman et al. |
| 2015/0202304 A1 | 7/2015 | Kaplan et al. |
| 2015/0202351 A1 | 7/2015 | Kaplan et al. |
| 2015/0211134 A1 | 7/2015 | Wang et al. |
| 2015/0216479 A1 | 8/2015 | Abreu |
| 2015/0216484 A1 | 8/2015 | Kasahara et al. |
| 2015/0231635 A1 | 8/2015 | Okano et al. |
| 2015/0232598 A1 | 8/2015 | Belbruno |
| 2015/0245797 A1 | 9/2015 | Teller et al. |
| 2015/0248651 A1 | 9/2015 | Akutagawa et al. |
| 2015/0248833 A1 | 9/2015 | Arne et al. |
| 2015/0251016 A1 | 9/2015 | Vo-Dinh et al. |
| 2015/0253317 A1 | 9/2015 | Singamaneni et al. |
| 2015/0253318 A1 | 9/2015 | Singamaneni et al. |
| 2015/0254724 A1 | 9/2015 | Kusukame et al. |
| 2015/0254964 A1 | 9/2015 | Raichman et al. |
| 2015/0259110 A1 | 9/2015 | Blackburn |
| 2015/0261254 A1 | 9/2015 | Hiroki et al. |
| 2015/0265214 A1 | 9/2015 | De Kok et al. |
| 2015/0265217 A1 | 9/2015 | Penders et al. |
| 2015/0265706 A1 | 9/2015 | Vo-Dinh et al. |
| 2015/0265725 A1 | 9/2015 | Peyman |
| 2015/0268207 A1 | 9/2015 | Motayed et al. |
| 2015/0269369 A1 | 9/2015 | Hamid |
| 2015/0271164 A1 | 9/2015 | Hamid |
| 2015/0272105 A1 | 10/2015 | Peterson |
| 2015/0272494 A1 | 10/2015 | Fuerst |
| 2015/0273521 A1 | 10/2015 | D'Arcy et al. |
| 2015/0276396 A1 | 10/2015 | Vock et al. |
| 2015/0276516 A1 | 10/2015 | Striemer |
| 2015/0276635 A1 | 10/2015 | Striemer |
| 2015/0276643 A1 | 10/2015 | Striemer |
| 2015/0276644 A1 | 10/2015 | Striemer |
| 2015/0276648 A1 | 10/2015 | Striemer |
| 2015/0276656 A1 | 10/2015 | Striemer |
| 2015/0281424 A1 | 10/2015 | Vock et al. |
| 2015/0281811 A1 | 10/2015 | Vock et al. |
| 2015/0282767 A1 | 10/2015 | Stivoric et al. |
| 2015/0299784 A1 | 10/2015 | Fan et al. |
| 2015/0301021 A1 | 10/2015 | Haick et al. |
| 2015/0301594 A1 | 10/2015 | Kitazawa et al. |
| 2015/0305682 A1 | 10/2015 | LeBoeuf et al. |
| 2015/0306505 A1 | 10/2015 | Vock et al. |
| 2015/0309316 A1 | 10/2015 | Osterhout et al. |
| 2015/0309535 A1 | 10/2015 | Connor |
| 2015/0309563 A1 | 10/2015 | Connor |
| 2015/0312712 A1 | 10/2015 | Vock et al. |
| 2015/0313496 A1 | 11/2015 | Connor |
| 2015/0316419 A1 | 11/2015 | Punnakkal |
| 2015/0320588 A1 | 11/2015 | Connor |
| 2015/0325100 A1 | 11/2015 | Hunter et al. |
| 2015/0327989 A1 | 11/2015 | Boyden et al. |
| 2015/0330025 A1 | 11/2015 | Marroquin et al. |
| 2015/0331512 A1 | 11/2015 | McMillen |
| 2015/0331997 A1 | 11/2015 | Joao |
| 2015/0335283 A1 | 11/2015 | Fish et al. |
| 2015/0335284 A1 | 11/2015 | Nuovo et al. |
| 2015/0339570 A1 | 11/2015 | Scheffler |
| 2015/0340891 A1 | 11/2015 | Fish et al. |
| 2015/0350752 A1 | 12/2015 | Solomon et al. |
| 2015/0351655 A1 | 12/2015 | Coleman |
| 2015/0351670 A1 | 12/2015 | Vanslyke et al. |
| 2015/0351671 A1 | 12/2015 | Vanslyke et al. |
| 2015/0351672 A1 | 12/2015 | Vanslyke et al. |
| 2015/0351673 A1 | 12/2015 | Vanslyke et al. |
| 2015/0355045 A1 | 12/2015 | Solomon et al. |
| 2015/0356093 A1 | 12/2015 | Abbas |
| 2015/0359457 A1 | 12/2015 | Blumenthal et al. |
| 2015/0359489 A1 | 12/2015 | Baudenbacher et al. |
| 2015/0363563 A1 | 12/2015 | Hallwachs |
| 2015/0366504 A1 | 12/2015 | Connor |
| 2015/0370320 A1 | 12/2015 | Connor |
| 2015/0374289 A1 | 12/2015 | Teller et al. |
| 2015/0379238 A1 | 12/2015 | Connor |
| 2016/0005503 A1 | 1/2016 | Bourke, Jr. et al. |
| 2016/0007933 A1 | 1/2016 | Duddy et al. |
| 2016/0008182 A1 | 1/2016 | Prokopuk et al. |
| 2016/0009169 A1 | 1/2016 | Biderman et al. |
| 2016/0009179 A1 | 1/2016 | Biderman et al. |
| 2016/0009181 A1 | 1/2016 | Biderman et al. |
| 2016/0009223 A1 | 1/2016 | Biderman et al. |
| 2016/0009293 A1 | 1/2016 | Biderman et al. |
| 2016/0009334 A1 | 1/2016 | Biderman et al. |
| 2016/0009335 A1 | 1/2016 | Biderman et al. |
| 2016/0009336 A1 | 1/2016 | Biderman et al. |
| 2016/0009337 A1 | 1/2016 | Biderman et al. |
| 2016/0009338 A1 | 1/2016 | Biderman |
| 2016/0009339 A1 | 1/2016 | Biderman et al. |
| 2016/0010136 A1 | 1/2016 | Nassar |
| 2016/0010151 A1 | 1/2016 | Fan et al. |
| 2016/0011003 A1 | 1/2016 | Biderman et al. |
| 2016/0011135 A1 | 1/2016 | Wang et al. |
| 2016/0011598 A1 | 1/2016 | Biderman et al. |
| 2016/0011599 A1 | 1/2016 | Biderman et al. |
| 2016/0012545 A1 | 1/2016 | Amigo et al. |
| 2016/0012652 A1 | 1/2016 | Biderman et al. |
| 2016/0012721 A1 | 1/2016 | Biderman et al. |
| 2016/0012723 A1 | 1/2016 | Biderman et al. |
| 2016/0012749 A1 | 1/2016 | Connor |
| 2016/0014205 A1 | 1/2016 | Biderman et al. |
| 2016/0014252 A1 | 1/2016 | Biderman et al. |
| 2016/0015267 A1 | 1/2016 | Bernstein et al. |
| 2016/0015268 A1 | 1/2016 | Bernstein et al. |
| 2016/0015280 A1 | 1/2016 | Hyde et al. |
| 2016/0015299 A1 | 1/2016 | Chan et al. |
| 2016/0015303 A1 | 1/2016 | Bernstein et al. |
| 2016/0015972 A1 | 1/2016 | Hyde et al. |
| 2016/0018257 A1 | 1/2016 | Mirov et al. |
| 2016/0018350 A1 | 1/2016 | Zhong et al. |
| 2016/0019813 A1 | 1/2016 | Mullen |
| 2016/0022210 A1 | 1/2016 | Nuovo et al. |
| 2016/0022976 A1 | 1/2016 | Peyman |
| 2016/0025634 A1 | 1/2016 | Chou et al. |
| 2016/0030078 A1 | 2/2016 | Lee et al. |
| 2016/0030809 A1 | 2/2016 | Wisbey et al. |
| 2016/0033861 A1 | 2/2016 | Omenetto et al. |
| 2016/0034663 A1 | 2/2016 | Nino et al. |
| 2016/0034764 A1 | 2/2016 | Connor |
| 2016/0038082 A1 | 2/2016 | Contant |
| 2016/0040998 A1 | 2/2016 | Ricci |
| 2016/0041820 A1 | 2/2016 | Ricci et al. |
| 2016/0042534 A1 | 2/2016 | Tremblay et al. |
| 2016/0045162 A1 | 2/2016 | De Graff et al. |
| 2016/0045654 A1 | 2/2016 | Connor |
| 2016/0051184 A1 | 2/2016 | Wisbey et al. |
| 2016/0051185 A1 | 2/2016 | Wisbey et al. |
| 2016/0051806 A1 | 2/2016 | Goldsmith |
| 2016/0054310 A1 | 2/2016 | Brennan et al. |
| 2016/0058328 A1 | 3/2016 | Hotta et al. |
| 2016/0058378 A1 | 3/2016 | Wisbey et al. |
| 2016/0058380 A1 | 3/2016 | Lee et al. |
| 2016/0060279 A1 | 3/2016 | Schoenfisch et al. |
| 2016/0062333 A1 | 3/2016 | Jayaraman |
| 2016/0066716 A1 | 3/2016 | Rao |
| 2016/0066894 A1 | 3/2016 | Barton-Sweeney |

(56) References Cited

U.S. PATENT DOCUMENTS

| | | |
|---|---|---|
| 2016/0067494 A1 | 3/2016 | Lipani |
| 2016/0073886 A1 | 3/2016 | Connor |
| 2016/0074276 A1 | 3/2016 | Scheuring et al. |
| 2016/0074511 A1 | 3/2016 | Lee et al. |
| 2016/0074661 A1 | 3/2016 | Lipani |
| 2016/0075175 A1 | 3/2016 | Biderman et al. |
| 2016/0075177 A1 | 3/2016 | Biderman et al. |
| 2016/0075226 A1 | 3/2016 | Biderman et al. |
| 2016/0082772 A1 | 3/2016 | Biderman et al. |
| 2016/0086193 A1 | 3/2016 | Hulaj |
| 2016/0089089 A1 | 3/2016 | Kakkar et al. |
| 2016/0095731 A1 | 4/2016 | Connor |
| 2016/0103104 A1 | 4/2016 | Gianchandani et al. |
| 2016/0110991 A1 | 4/2016 | Hunter et al. |
| 2016/0112684 A1 | 4/2016 | Connor |
| 2016/0112775 A1 | 4/2016 | Kim et al. |
| 2016/0113503 A1 | 4/2016 | Benaron |
| 2016/0117029 A1 | 4/2016 | Short et al. |
| 2016/0117937 A1 | 4/2016 | Penders et al. |
| 2016/0118640 A1 | 4/2016 | Miyake |
| 2016/0120433 A1 | 5/2016 | Hughes et al. |
| 2016/0120434 A1 | 5/2016 | Park et al. |
| 2016/0128615 A1 | 5/2016 | Curry et al. |
| 2016/0128638 A1 | 5/2016 | Altini et al. |
| 2016/0129280 A1 | 5/2016 | Douglas |
| 2016/0130056 A1 | 5/2016 | Nishijima et al. |
| 2016/0130335 A1 | 5/2016 | Ruvo et al. |
| 2016/0130370 A1 | 5/2016 | Carson et al. |
| 2016/0131615 A1 | 5/2016 | Sun et al. |
| 2016/0134642 A1 | 5/2016 | Hamid et al. |
| 2016/0140870 A1 | 5/2016 | Connor |
| 2016/0141718 A1 | 5/2016 | Ye et al. |
| 2016/0143547 A1 | 5/2016 | Benaron |
| 2016/0145683 A1 | 5/2016 | Fan et al. |
| 2016/0146799 A1 | 5/2016 | Robinson et al. |
| 2016/0148103 A1 | 5/2016 | Sarrafzadeh et al. |
| 2016/0148215 A1 | 5/2016 | Von Teichman et al. |
| 2016/0148531 A1 | 5/2016 | Bleich et al. |
| 2016/0148597 A1 | 5/2016 | Hamid et al. |
| 2016/0151628 A1 | 6/2016 | Simon et al. |
| 2016/0157779 A1 | 6/2016 | Baxi et al. |
| 2016/0161472 A1 | 6/2016 | Jungmann et al. |
| 2016/0165852 A1 | 6/2016 | Goldfain |
| 2016/0165853 A1 | 6/2016 | Goldfain |
| 2016/0166203 A1 | 6/2016 | Goldstein |
| 2016/0166786 A1 | 6/2016 | Kinzer |
| 2016/0166930 A1 | 6/2016 | Brav et al. |
| 2016/0169810 A1 | 6/2016 | Swager et al. |
| 2016/0169930 A1 | 6/2016 | Korhonen et al. |
| 2016/0171623 A1 | 6/2016 | Amigo et al. |
| 2016/0171846 A1 | 6/2016 | Brav et al. |
| 2016/0174039 A1 | 6/2016 | Huang |
| 2016/0174099 A1 | 6/2016 | Goldfain |
| 2016/0174857 A1 | 6/2016 | Eggers et al. |
| 2016/0174891 A1 | 6/2016 | Vilermo et al. |
| 2016/0174892 A1 | 6/2016 | Benson et al. |
| 2016/0174903 A1 | 6/2016 | Cutaia |
| 2016/0175251 A1 | 6/2016 | Ostroff et al. |
| 2016/0178392 A1 | 6/2016 | Goldfain |
| 2016/0180222 A1 | 6/2016 | Sierhuis et al. |
| 2016/0182625 A1 | 6/2016 | Trainin et al. |
| 2016/0184226 A1 | 6/2016 | Thaxton et al. |
| 2016/0184703 A1 | 6/2016 | Brav et al. |
| 2016/0185814 A1 | 6/2016 | Field et al. |
| 2016/0187654 A1 | 6/2016 | Border et al. |
| 2016/0189534 A1 | 6/2016 | Wang et al. |
| 2016/0195486 A1 | 7/2016 | Anvar et al. |
| 2016/0195504 A1 | 7/2016 | Swager et al. |
| 2016/0195566 A1 | 7/2016 | Vock et al. |
| 2016/0199249 A1 | 7/2016 | Dunham et al. |
| 2016/0202755 A1 | 7/2016 | Connor |
| 2016/0205450 A1 | 7/2016 | Gartseev et al. |
| 2016/0206232 A1 | 7/2016 | Bordelon |
| 2016/0209420 A1 | 7/2016 | Barnes et al. |
| 2016/0209648 A1 | 7/2016 | Haddick et al. |
| 2016/0210416 A1 | 7/2016 | Whitehurst |
| 2016/0217259 A1 | 7/2016 | Chan et al. |
| 2016/0222539 A1 | 8/2016 | Varadan et al. |
| 2016/0228574 A1 | 8/2016 | Farokhzad et al. |
| 2016/0228640 A1 | 8/2016 | Pindado et al. |
| 2016/0231267 A1 | 8/2016 | Swager et al. |
| 2016/0232625 A1 | 8/2016 | Akutagawa et al. |
| 2016/0232811 A9 | 8/2016 | Connor |
| 2016/0233469 A1 | 8/2016 | Kimura |
| 2016/0233946 A1 | 8/2016 | Wengrovitz et al. |
| 2016/0234176 A1 | 8/2016 | Chu et al. |
| 2016/0238591 A1 | 8/2016 | Deng et al. |
| 2016/0242646 A1 | 8/2016 | Obma |
| 2016/0243235 A1 | 8/2016 | Vo-Dinh et al. |
| 2016/0243927 A1 | 8/2016 | Biderman et al. |
| 2016/0245686 A1 | 8/2016 | Pal et al. |
| 2016/0249832 A1 | 9/2016 | Carter et al. |
| 2016/0249853 A1 | 9/2016 | Ricci |
| 2016/0258012 A2 | 9/2016 | Fan et al. |
| 2016/0258758 A1 | 9/2016 | Houston et al. |
| 2016/0262666 A1 | 9/2016 | Nyberg et al. |
| 2016/0262667 A1 | 9/2016 | Pizer et al. |
| 2016/0263393 A1 | 9/2016 | Vo-Dinh et al. |
| 2016/0265069 A1 | 9/2016 | Fan et al. |
| 2016/0267238 A1 | 9/2016 | Nag |
| 2016/0269692 A1 | 9/2016 | Mazzarella et al. |
| 2016/0270126 A1 | 9/2016 | Adams et al. |
| 2016/0270239 A1 | 9/2016 | Pizer et al. |
| 2016/0270671 A1 | 9/2016 | Madabushi et al. |
| 2016/0270700 A1 | 9/2016 | Baxi et al. |
| 2016/0270726 A1 | 9/2016 | Abreu |
| 2016/0274048 A1 | 9/2016 | Mehregany |
| 2016/0274086 A1 | 9/2016 | Rose-Petruck et al. |
| 2016/0277528 A1 | 9/2016 | Guilaume et al. |
| 2016/0278647 A1 | 9/2016 | Vogel et al. |
| 2016/0278700 A1 | 9/2016 | Lee et al. |
| 2016/0280069 A1 | 9/2016 | Laute et al. |
| 2016/0282302 A1 | 9/2016 | Raguse et al. |
| 2016/0287089 A1 | 10/2016 | Yi et al. |
| 2016/0287148 A1 | 10/2016 | Pizer et al. |
| 2016/0287164 A1 | 10/2016 | Manion et al. |
| 2016/0287166 A1 | 10/2016 | Tran |
| 2016/0290952 A1 | 10/2016 | Pizer et al. |
| 2016/0290980 A1 | 10/2016 | Swager et al. |
| 2016/0296839 A1 | 10/2016 | Brav et al. |
| 2016/0301581 A1 | 10/2016 | Carter et al. |
| 2016/0302730 A1 | 10/2016 | Odate |
| 2016/0307284 A1 | 10/2016 | Parsons |
| 2016/0310011 A1 | 10/2016 | Abreu |
| 2016/0313798 A1 | 10/2016 | Connor |
| 2016/0314564 A1 | 10/2016 | Jones et al. |
| 2016/0317049 A1 | 11/2016 | LeBoeuf et al. |
| 2016/0317060 A1 | 11/2016 | Connor |
| 2016/0321677 A1 | 11/2016 | Dobaj |
| 2016/0322744 A1 | 11/2016 | Murison |
| 2016/0324478 A1 | 11/2016 | Goldstein |
| 2016/0325111 A1 | 11/2016 | Bourke, Jr. et al. |
| 2016/0331235 A1 | 11/2016 | Nyberg et al. |
| 2016/0334398 A1 | 11/2016 | Weissleder et al. |
| 2016/0338626 A1 | 11/2016 | Wang et al. |
| 2016/0338627 A1 | 11/2016 | Lansdorp et al. |
| 2016/0338644 A1 | 11/2016 | Connor |
| 2016/0338646 A1 | 11/2016 | Lee et al. |
| 2016/0339428 A1 | 11/2016 | Kim et al. |
| 2016/0342744 A1 | 11/2016 | Joao |
| 2016/0349090 A1 | 12/2016 | Zevenbergen et al. |
| 2016/0349305 A1 | 12/2016 | Pal |
| 2016/0349790 A1 | 12/2016 | Connor |
| 2016/0351045 A1 | 12/2016 | Salter |
| 2016/0351874 A1 | 12/2016 | Kang et al. |
| 2016/0354543 A1 | 12/2016 | Cinar et al. |
| 2016/0360153 A1 | 12/2016 | Mazzarella et al. |
| 2016/0361014 A1 | 12/2016 | Kane et al. |
| 2016/0366065 A1 | 12/2016 | Kazanchian et al. |
| 2016/0367151 A1 | 12/2016 | Le et al. |
| 2016/0367202 A1 | 12/2016 | Carter et al. |
| 2016/0370310 A1 | 12/2016 | BelBruno et al. |
| 2016/0371372 A1 | 12/2016 | Chong et al. |
| 2016/0374577 A1 | 12/2016 | Baxi et al. |

(56) References Cited

U.S. PATENT DOCUMENTS

| | | |
|---|---|---|
| 2016/0374598 A1 | 12/2016 | Heikenfeld et al. |
| 2016/0374621 A1 | 12/2016 | LeBoeuf et al. |
| 2016/0375308 A1 | 12/2016 | Anderson |
| 2016/0376650 A1 | 12/2016 | Baranova et al. |
| 2017/0000359 A1 | 1/2017 | Kohli et al. |
| 2017/0000936 A1 | 1/2017 | Soykan et al. |
| 2017/0005958 A1 | 1/2017 | Frenkel et al. |
| 2017/0010658 A1 | 1/2017 | Tanaka et al. |
| 2017/0010664 A1 | 1/2017 | Tanaka et al. |
| 2017/0010665 A1 | 1/2017 | Tanaka et al. |
| 2017/0010667 A1 | 1/2017 | Tanaka et al. |
| 2017/0010672 A1 | 1/2017 | Tanaka et al. |
| 2017/0011182 A1 | 1/2017 | Whitehurst |
| 2017/0011602 A1 | 1/2017 | Brav et al. |
| 2017/0014067 A1 | 1/2017 | Peppou et al. |
| 2017/0014511 A1 | 1/2017 | Vitaliano et al. |
| 2017/0020390 A1 | 1/2017 | Flitsch et al. |
| 2017/0020391 A1 | 1/2017 | Flitsch et al. |
| 2017/0020417 A1 | 1/2017 | Stafford |
| 2017/0020431 A1 | 1/2017 | Flitsch et al. |
| 2017/0020440 A1 | 1/2017 | Flitsch et al. |
| 2017/0020441 A1 | 1/2017 | Flitsch et al. |
| 2017/0020442 A1 | 1/2017 | Flitsch et al. |
| 2017/0021040 A1 | 1/2017 | Vitaliano et al. |
| 2017/0023509 A1 | 1/2017 | Kim et al. |
| 2017/0024530 A1 | 1/2017 | Flitsch et al. |
| 2017/0024535 A1 | 1/2017 | Matz et al. |
| 2017/0024555 A1 | 1/2017 | Flitsch et al. |
| 2017/0024771 A1 | 1/2017 | Flitsch et al. |
| 2017/0026790 A1 | 1/2017 | Flitsch et al. |
| 2017/0027511 A1 | 2/2017 | Connor |
| 2017/0030877 A1 | 2/2017 | Miresmailli et al. |
| 2017/0032258 A1 | 2/2017 | Miresmailli et al. |
| 2017/0038326 A1 | 2/2017 | Motayed et al. |
| 2017/0043178 A1 | 2/2017 | Vo-Dinh et al. |
| 2017/0046740 A1 | 2/2017 | Abbas |
| 2017/0048257 A1 | 2/2017 | Hamid |
| 2017/0050046 A1 | 2/2017 | Walder et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0055906 A1* | 3/2017 | Bremer ............... A61B 5/6833 |
| 2017/0065183 A1 | 3/2017 | Abreu |
| 2017/0065636 A1 | 3/2017 | Moriarity et al. |
| 2017/0067021 A1 | 3/2017 | Moriarity et al. |
| 2017/0068790 A1 | 3/2017 | Fuerst |
| 2017/0078223 A1 | 3/2017 | Ricci et al. |
| 2017/0079574 A1 | 3/2017 | Rodriguez Restrepo et al. |
| 2017/0079594 A1 | 3/2017 | Telfort et al. |
| 2017/0080346 A1 | 3/2017 | Abbas |
| 2017/0086291 A1 | 3/2017 | Cotton et al. |
| 2017/0086709 A1 | 3/2017 | Khine et al. |
| 2017/0087363 A1 | 3/2017 | Costanzo et al. |
| 2017/0088875 A1 | 3/2017 | Li et al. |
| 2017/0090466 A1 | 3/2017 | Uomori |
| 2017/0091412 A1 | 3/2017 | Johnson |
| 2017/0091426 A1 | 3/2017 | Johnson |
| 2017/0091498 A1 | 3/2017 | Forster et al. |
| 2017/0093981 A1 | 3/2017 | Cameron |
| 2017/0094216 A1 | 3/2017 | Ekambaram et al. |
| 2017/0095153 A1 | 4/2017 | Bardy et al. |
| 2017/0095183 A1 | 4/2017 | Heikenfeld |
| 2017/0095184 A1 | 4/2017 | Heikenfeld |
| 2017/0095233 A1 | 4/2017 | Heikenfeld |
| 2017/0095670 A1 | 4/2017 | Ghaffari et al. |
| 2017/0095721 A1 | 4/2017 | Bleich et al. |
| 2017/0100035 A1 | 4/2017 | Heikenfeld |
| 2017/0100064 A1 | 4/2017 | Van Dorpe et al. |
| 2017/0100071 A1 | 4/2017 | Heikenfeld |
| 2017/0100072 A1 | 4/2017 | Heikenfeld |
| 2017/0100076 A1 | 4/2017 | Benson et al. |
| 2017/0100102 A1 | 4/2017 | Heikenfeld |
| 2017/0103166 A1 | 4/2017 | Oh et al. |
| 2017/0105104 A1 | 4/2017 | Ulmansky et al. |
| 2017/0105622 A1 | 4/2017 | Boesen et al. |
| 2017/0105646 A1 | 4/2017 | Bryenton et al. |
| 2017/0105662 A1 | 4/2017 | Silawan et al. |
| 2017/0109829 A1 | 4/2017 | Amigo et al. |
| 2017/0110678 A1 | 4/2017 | Zang et al. |
| 2017/0112379 A1 | 4/2017 | Swiston et al. |
| 2017/0112422 A1 | 4/2017 | Hatch |
| 2017/0112447 A1 | 4/2017 | Aumer et al. |
| 2017/0112671 A1 | 4/2017 | Goldstein |
| 2017/0113641 A1 | 4/2017 | Thieberger et al. |
| 2017/0113702 A1 | 4/2017 | Thieberger-Navon et al. |
| 2017/0116879 A1 | 4/2017 | Baarman et al. |
| 2017/0118551 A1 | 4/2017 | Wagner et al. |
| 2017/0119255 A1 | 5/2017 | Mahajan et al. |
| 2017/0119289 A1* | 5/2017 | Yoshioka ............. A61B 5/1455 |
| 2017/0119311 A1 | 5/2017 | Iwasaki et al. |
| 2017/0119820 A1 | 5/2017 | Moriarity et al. |
| 2017/0120052 A9 | 5/2017 | Simon et al. |
| 2017/0120107 A1 | 5/2017 | Wisbey |
| 2017/0121472 A1 | 5/2017 | Bourke, Jr. et al. |
| 2017/0121708 A1 | 5/2017 | Shapiro et al. |
| 2017/0124110 A1 | 5/2017 | Hajj et al. |
| 2017/0124276 A1 | 5/2017 | Tee |
| 2017/0127957 A1 | 5/2017 | Wisbey et al. |
| 2017/0130200 A1 | 5/2017 | Moriarity et al. |
| 2017/0131163 A1 | 5/2017 | LaBelle et al. |
| 2017/0131291 A1 | 5/2017 | Huang |
| 2017/0133873 A1 | 5/2017 | Dalton et al. |
| 2017/0135633 A1 | 5/2017 | Connor |
| 2017/0136264 A1 | 5/2017 | Hyde et al. |
| 2017/0136265 A1 | 5/2017 | Hyde et al. |
| 2017/0140482 A1 | 5/2017 | Salter |
| 2017/0140626 A1 | 5/2017 | Freathy |
| 2017/0142023 A1 | 5/2017 | Yadav et al. |
| 2017/0142113 A1 | 5/2017 | Bourgeois et al. |
| 2017/0151339 A1 | 6/2017 | White et al. |
| 2017/0156635 A1 | 6/2017 | Kuo et al. |
| 2017/0156641 A1 | 6/2017 | Nyberg et al. |
| 2017/0156662 A1 | 6/2017 | Goodall et al. |
| 2017/0157430 A1 | 6/2017 | Cheatham et al. |
| 2017/0157431 A1 | 6/2017 | Cheatham et al. |
| 2017/0160252 A1 | 6/2017 | Zang et al. |
| 2017/0162023 A1 | 6/2017 | Hunter et al. |
| 2017/0164865 A1 | 6/2017 | Rafferty et al. |
| 2017/0164866 A1 | 6/2017 | Rafferty et al. |
| 2017/0164876 A1* | 6/2017 | Hyde ................... A61B 5/4836 |
| 2017/0164878 A1 | 6/2017 | Connor |
| 2017/0166760 A1 | 6/2017 | Dietsch et al. |
| 2017/0167934 A1 | 6/2017 | Haick et al. |
| 2017/0168566 A1 | 6/2017 | Osterhout et al. |
| 2017/0172424 A1 | 6/2017 | Eggers et al. |
| 2017/0172463 A1 | 6/2017 | Papadopoulos et al. |
| 2017/0172470 A1 | 6/2017 | Begtrup et al. |
| 2017/0172484 A1 | 6/2017 | Sonner et al. |
| 2017/0173262 A1 | 6/2017 | Veltz |
| 2017/0173350 A1 | 6/2017 | Bourke, Jr. et al. |
| 2017/0177025 A1 | 6/2017 | Hiroki et al. |
| 2017/0181659 A1 | 6/2017 | Rafferty et al. |
| 2017/0181684 A1 | 6/2017 | Lian |
| 2017/0181711 A1 | 6/2017 | Cheng et al. |
| 2017/0184574 A1 | 6/2017 | Singaram et al. |
| 2017/0185731 A1 | 6/2017 | Ranieri et al. |
| 2017/0185743 A1 | 6/2017 | Moshkovitz et al. |
| 2017/0185745 A1 | 6/2017 | Wartski et al. |
| 2017/0188872 A1 | 7/2017 | Hughes et al. |
| 2017/0189481 A1 | 7/2017 | Kang et al. |
| 2017/0189751 A1 | 7/2017 | Knickerbocker et al. |
| 2017/0193395 A1 | 7/2017 | Limonad et al. |
| 2017/0196977 A1 | 7/2017 | Vo-Dinh et al. |
| 2017/0199979 A1 | 7/2017 | Reiner |
| 2017/0200296 A1 | 7/2017 | Jones et al. |
| 2017/0200898 A1 | 7/2017 | Noh |
| 2017/0205221 A1 | 7/2017 | Gong et al. |
| 2017/0206721 A1 | 7/2017 | Koo |
| 2017/0209095 A1 | 7/2017 | Wagner et al. |
| 2017/0210115 A1 | 7/2017 | Ohno et al. |
| 2017/0214020 A1 | 7/2017 | Yamaguchi et al. |
| 2017/0214963 A1 | 7/2017 | Di Franco et al. |
| 2017/0215742 A1 | 8/2017 | Wisbey et al. |

(56) References Cited

U.S. PATENT DOCUMENTS

| | | |
|---|---|---|
| 2017/0215745 A1 | 8/2017 | Felix et al. |
| 2017/0216671 A1 | 8/2017 | Wisbey et al. |
| 2017/0216672 A1 | 8/2017 | Wisbey et al. |
| 2017/0216673 A1 | 8/2017 | Armstrong et al. |
| 2017/0220772 A1 | 8/2017 | Vleugels et al. |

* cited by examiner

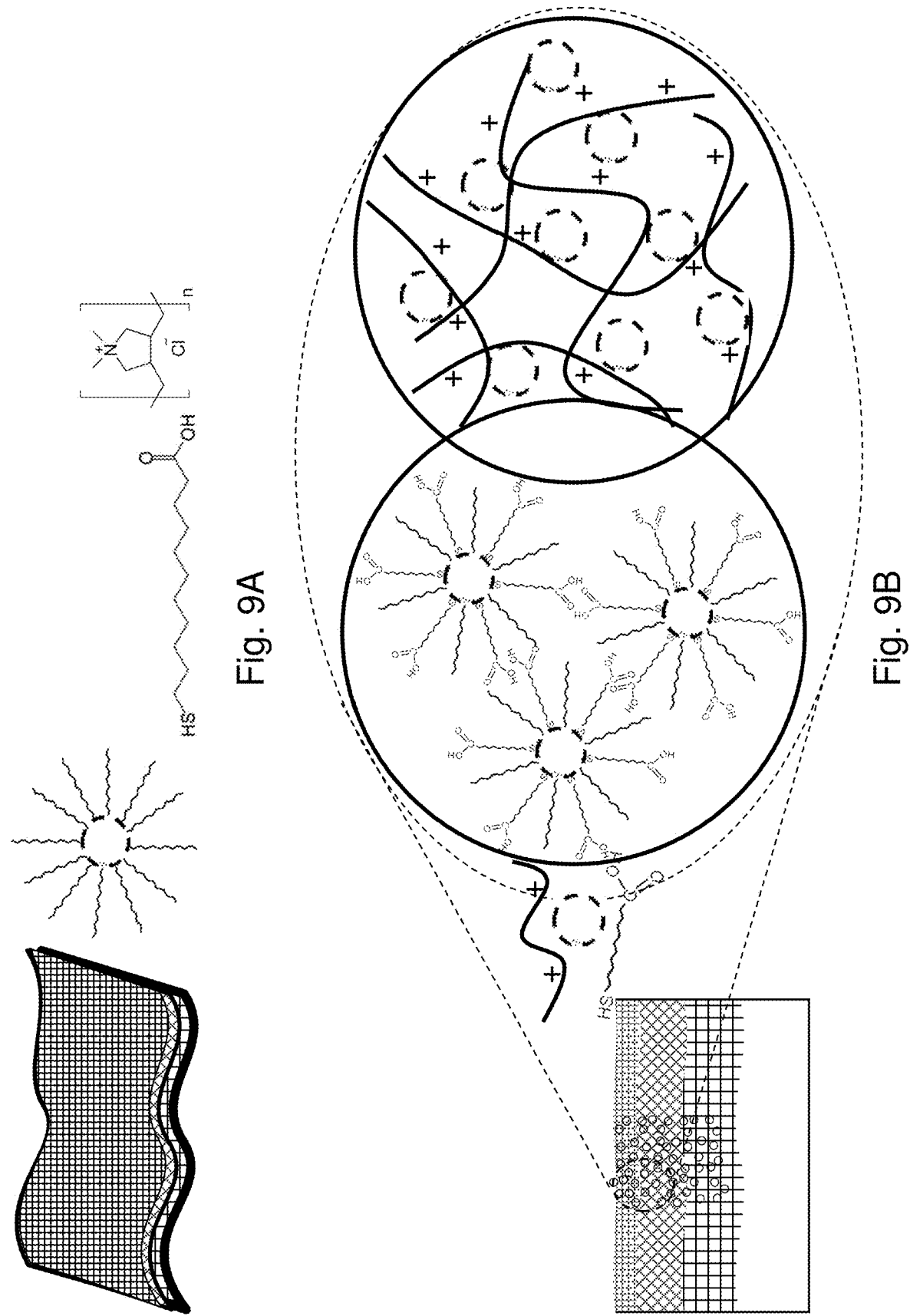

NANOPARTICLE SENSOR HAVING A NANOFIBROUS MEMBRANE SCAFFOLD

CROSS REFERENCE TO RELATED APPLICATION

The present application is a non-provisional of, and claims benefit of priority under 35 U.S.C. § 119(e) from, U.S. Provisional Patent Application 62/542,067, filed Aug. 7, 2017, the entirety of which is expressly incorporated herein by reference.

STATEMENT OF GOVERNMENT RIGHTS

This invention was made with government support under IIP-1640669, awarded by the National Science Foundation. The government has certain rights in the invention.

FIELD OF THE INVENTION

The present invention relates to the field of biological fluid sensors, and more particularly to sweat or biomarker secretion sensors.

BACKGROUND OF THE INVENTION

Sweating is primarily used to regulate body temperature by cooling the body down with secretion of water. The inability of human body to sweat properly is potentially harmful, and a complete absence of sweating (anhidrosis) or sweating less than normal (hypohidrosis) is an abnormal lack of sweat in response to heat, which is also one of the symptoms of some genetic diseases. As such, monitoring of the moisture levels from perspiration provides useful information for assessing the physical conditions, especially for people exposed to high temperature or experiencing long time exercise who face the risk of dehydration. The fact that sweat contains abundant information of medical significance has been an important driving force for the increasing interests in developing wearable sweat sensors. In addition to moisture, sweat is also rich with ions such as sodium, potassium and chlorine ranging from 10 to 80 mM. Monitoring the saltiness thus provides further useful information. Moreover, sweat may also contain biomarkers related to metabolites of the human body, e.g., glucose, lactate, and uric acid. While some progress has been made in developing sweat sensors, key challenges remain, including lack of multifunctionality, biocompatibility, and flexibility in some monitoring conditions, high cost in manufacturing, and insufficient sensitivity and selectivity, calling for breakthroughs in materials design and fabrication.

See, U.S. Pat. Nos. 5,729,203; 6,198,953; 6,882,940; 7,109,933; 7,187,960; 7,383,072; 8,032,199; 8,328,420; 8,527,028; 8,560,044; 8,721,562; 8,834,020; 8,849,379; 9,011,349; 9,028,405; 9,198,605; 9,198,617; 9,204,808; 9,254,437; 9,277,867; 9,301,719; 9,398,856; 9,408,572; 9,449,084; 9,510,784; 9,545,221; 9,563,995; 9,579,024; 9,579,040; 9,603,560; 9,622,725; 9,636,061; 9,645,133; 9,686,499; 9,704,205; 9,713,447; 9,717,455; 20020106709; 20040059212; 20040242976; 20050119540; 20050194012; 20050195118; 20060253011; 20070173886; 20070197878; 20070219434; 20080027679; 20080081963; 20080091097; 20080287769; 20080287770; 20080294058; 20090018412; 20090105605; 20090269003; 20090312615; 20100099957; 20100240962; 20120020033; 20120157793; 20120215076; 20120229661; 20130057720; 20130066168; 20130096396; 20130124039; 20130197319; 20130234724; 20130245388; 20130288777; 20140012145; 20140031705; 20140106816; 20140200432; 20140206948; 20140249763; 20140275828; 20140275838; 20140275840; 20140277649; 20140347187; 20150038874; 20150093725; 20150094914; 20150112164; 20150112165; 20150145676; 20150148628; 20150148681; 20150150453; 20150150467; 20150164238; 20150164409; 20150216479; 20150248651; 20150301594; 20150320588; 20160038082; 20160117029; 20160174892; 20160232625; 20160262666; 20160262667; 20160270239; 20160270726; 20160278700; 20160287148; 20160290952; 20160302730; 20160310011; 20160331235; 20160349790; 20160371372; 20160374598; 20170065183; 20170079574; 20170094216; 20170095183; 20170095184; 20170095233; 20170100035; 20170100071; 20170100072; 20170100076; 20170100102; 20170103166; 20170105104; 20170105646; 20170105662; 20170116879; 20170119311; 20170135633; 20170136264; 20170136265; 20170140626; 20170156641; 20170156662; 20170157430; 20170157431; 20170164865; 20170164866; 20170164876; 20170164878; 20170172470; 20170172484; 20170181659; and 20170181684.

Sensors formed using gold nanoparticles are known: see, U.S. Pat. Nos. 6,361,944; 6,417,340; 6,495,324; 6,506,564; 6,541,617; 6,582,921; 6,610,491; 6,645,721; 6,673,548; 6,677,122; 6,682,895; 6,709,825; 6,720,147; 6,720,411; 6,730,269; 6,740,491; 6,750,016; 6,759,199; 6,767,702; 6,773,884; 6,777,186; 6,812,334; 6,818,753; 6,828,432; 6,861,221; 6,878,814; 6,902,895; 6,903,207; 6,962,786; 6,969,761; 6,984,491; 6,986,989; 7,052,854; 7,098,320; 7,169,556; 7,195,780; 7,208,587; 7,250,499; 7,259,252; 7,267,948; 7,435,386; 7,485,419; 7,534,560; 7,569,354; 7,611,628; 7,612,185; 7,695,738; 7,799,554; 7,816,491; 7,863,376; 7,985,424; 8,012,743; 8,067,393; 8,216,854; 8,282,967; 8,283,414; 8,323,694; 8,323,888; 8,376,013; 8,383,415; 8,389,958; 8,426,214; 8,486,720; 8,501,921; 8,507,200; 8,524,457; 8,598,046; 8,618,509; 8,652,778; 8,666,471; 8,679,859; 8,703,439; 8,717,558; 8,758,772; 8,770,203; 8,883,964; 8,906,831; 8,920,971; 8,927,615; 8,945,943; 8,951,561; 8,956,658; 8,956,863; 8,962,029; 8,962,912; 8,993,349; 8,999,947; 9,000,137; 9,004,131; 9,012,156; 9,067,181; 9,102,520; 9,114,107; 9,157,109; 9,174,190; 9,174,873; 9,201,071; 9,216,155; 9,222,884; 9,242,857; 9,243,128; 9,246,122; 9,250,238; 9,274,108; 9,276,238; 9,283,275; 9,290,799; 9,302,116; 9,310,372; 9,315,942; 9,316,645; 9,320,813; 9,321,030; 9,333,163; 9,340,416; 9,376,690; 9,393,396; 9,403,851; 9,403,852; 9,410,949; 9,416,493; 9,437,628; 9,439,868; 9,440,195; 9,446,150; 9,447,129; 9,486,512; 9,494,524; 9,506,056; 9,508,956; 9,511,329; 9,526,913; 9,526,914; 9,532,956; 9,534,024; 9,540,422; 9,555,392; 9,556,473; 9,557,340; 9,567,645; 9,567,646; 9,579,523; 9,581,590; 9,592,198; 9,598,544; 9,598,736; 9,604,168; 9,623,352; 9,623,381; 9,624,275; 9,630,022; 9,637,380; 9,637,799; 9,637,830; 9,649,391; 9,662,299; 9,662,388; 9,662,389; 9,664,674; 9,688,750; 9,691,873; 9,701,784; 9,709,559; 9,717,685; 9,719,089; 20020127574; 20020137058; 20020137070; 20020137071; 20020137072; 20020146720; 20020155442; 20020155458; 20020155459; 20020155461; 20020155462; 20020160381; 20020164605; 20020172953; 20020182611; 20020182613; 20030022169; 20030044805; 20030049630; 20030049631; 20030054358; 20030059777; 20030059820; 20030068622; 20030087242; 20030124528; 20030143538; 20030148282; 20030180783; 20030198956; 20030207296; 20030215903; 20040018587; 20040072231; 20040076681; 20040110220; 20040219520; 20050037374; 20050059030; 20050059031; 20050130174; 20050130240; 20050176029; 20050250094; 20050272114; 20050287552; 20060014172; 20060040318; 20060057613; 20060068378; 20060257883;

20070059763; 20070087383; 20070087400; 20070122829; 20070125181; 20070127164; 20070154903; 20070258894; 20070269821; 20070298006; 20080146701; 20080226995; 20080241071; 20080241964; 20080279946; 20080287342; 20090042200; 20090042739; 20090130773; 20090214618; 20090246142; 20090294692; 20090325215; 20090325812; 20100003316; 20100009872; 20100016568; 20100016569; 20100016783; 20100018862; 20100021933; 20100028559; 20100062232; 20100069621; 20100196920; 20100234579; 20100261263; 20100290992; 20110012096; 20110021970; 20110065807; 20110098197; 20110114244; 20110114511; 20110129537; 20110136139; 20110171749; 20110176130; 20110206740; 20110263920; 20120021055; 20120034169; 20120064134; 20120070376; 20120087949; 20120135437; 20120156135; 20120263648; 20120263793; 20120315322; 20130023714; 20130034599; 20130034915; 20130095499; 20130116405; 20130140649; 20130156905; 20130171060; 20130177598; 20130183243; 20130196872; 20130203073; 20130210023; 20130240758; 20130252843; 20130252848; 20130261010; 20130295688; 20140005426; 20140024026; 20140050793; 20140058124; 20140120534; 20140163303; 20140222117; 20140243934; 20140273029; 20140294927; 20140322823; 20140335154; 20140343479; 20140363833; 20140364332; 20140378676; 20150005188; 20150017258; 20150031571; 20150056627; 20150093774; 20150111308; 20150141266; 20150164117; 20150182543; 20150198606; 20150202304; 20150202351; 20150211134; 20150231635; 20150251016; 20150253317; 20150253318; 20150265706; 20150265725; 20150299784; 20150330025; 20160005503; 20160010136; 20160010151; 20160022976; 20160025634; 20160033861; 20160054310; 20160060279; 20160074511; 20160130056; 20160130335; 20160130370; 20160131615; 20160145683; 20160146799; 20160161472; 20160175251; 20160184226; 20160185814; 20160228574; 20160238591; 20160243235; 20160258012; 20160263393; 20160265069; 20160274086; 20160325111; 20160334398; 20160351874; 20170014511; 20170021040; 20170043178; 20170050046; 20170065636; 20170067021; 20170088875; 20170119820; 20170121472; 20170121708; 20170130200; 20170131291; 20170151339; 20170166760; 20170173350; 20170184574; 20170189481; 20170196977; 20170210115; and 20170214020.

Various chemiresistor technologies, and applications thereof, are known: see, U.S. Pat. Nos. 4,636,767; 4,759,210; 4,847,594; 4,886,625; 4,900,817; 4,992,244; 5,045,285; 5,071,770; 5,089,294; 5,210,217; 5,224,972; 5,238,729; 5,279,795; 5,280,183; 5,302,935; 5,321,146; 5,387,462; 5,433,971; 5,469,369; 5,498,323; 5,512,882; 5,536,473; 5,550,062; 5,571,401; 5,589,396; 5,629,435; 5,674,752; 5,698,083; 5,698,089; 5,788,833; 5,858,186; 5,891,398; 5,911,872; 5,951,846; 5,959,191; 5,976,466; 6,004,494; 6,010,616; 6,013,229; 6,015,869; 6,017,440; 6,085,576; 6,093,308; 6,170,318; 6,221,673; 6,238,085; 6,244,096; 6,290,911; 6,319,724; 6,331,244; 6,350,369; 6,359,444; 6,387,329; 6,397,661; 6,408,250; 6,418,783; 6,421,588; 6,422,061; 6,458,327; 7,122,152; 7,136,716; 7,138,090; 7,144,553; 7,144,949; 7,168,294; 7,175,885; 7,179,421; 7,189,353; 7,189,360; 7,189,867; 7,191,805; 7,201,035; 7,211,439; 7,211,637; 7,226,530; 7,229,593; 7,233,781; 7,242,310; 7,253,004; 7,265,560; 7,272,530; 7,288,415; 7,313,447; 7,340,941; 7,342,479; 7,347,974; 7,356,420; 7,359,802; 7,387,010; 7,395,693; 7,397,072; 7,404,928; 7,421,883; 7,438,079; 7,449,050; 7,471,185; 7,477,994; 7,489,252; 7,501,091; 7,527,821; 7,531,136; 7,531,137; 7,538,538; 7,550,310; 7,556,775; 7,595,023; 7,595,734; 7,645,422; 7,708,947; 7,726,175; 7,737,322; 7,760,101; 7,793,675; 7,799,276; 7,801,687; 7,840,359; 7,880,026; 7,889,954; 7,911,010; 7,912,561; 7,927,558; 7,939,130; 7,950,271; 7,955,561; 7,966,132; 7,998,415; 7,998,416; 8,000,903; 8,012,326; 8,012,420; 8,030,100; 8,087,283; 8,088,341; 8,105,538; 8,123,834; 8,123,841; 8,152,908; 8,153,439; 8,168,438; 8,178,045; 8,187,887; 8,231,746; 8,246,910; 8,268,630; 8,269,029; 8,272,250; 8,285,493; 8,309,028; 8,310,016; 8,336,402; 8,352,049; 8,366,630; 8,394,330; 8,409,510; 8,412,147; 8,426,208; 8,426,932; 8,441,081; 8,448,532; 8,449,824; 8,461,354; 8,481,324; 8,497,130; 8,519,726; 8,562,878; 8,567,232; 8,569,691; 8,618,330; 8,691,390; 8,694,267; 8,695,401; 8,703,500; 8,707,760; 8,736,287; 8,771,613; 8,790,400; 8,795,359; 8,808,373; 8,816,116; 8,828,733; 8,846,406; 8,877,636; 8,884,382; 8,889,420; 8,900,516; 8,903,661; 8,904,849; 8,920,731; 8,940,092; 8,951,473; 8,957,253; 8,978,444; 8,986,615; 8,989,053; 8,999,244; 8,999,245; 9,017,773; 9,034,266; 9,034,275; 9,034,659; 9,067,070; 9,080,942; 9,120,677; 9,144,488; 9,144,489; 9,147,338; 9,157,842; 9,182,231; 9,182,232; 9,211,185; 9,212,055; 9,217,722; 9,234,757; 9,254,099; 9,260,683; 9,267,908; 9,267,964; 9,315,848; 9,326,730; 9,333,071; 9,339,372; 9,360,509; 9,377,426; 9,402,242; 9,429,536; 9,442,100; 9,448,219; 9,453,811; 9,459,222; 9,459,223; 9,476,862; 9,494,541; 9,510,316; 9,514,632; 9,518,956; 9,529,385; 9,536,122; 9,536,449; 9,538,657; 9,563,833; 9,567,225; 9,582,035; 9,589,686; 9,591,607; 9,598,282; 9,598,785; 9,606,245; 9,613,521; 9,625,341; 9,632,050; 9,638,653; 9,658,178; 9,658,196; 9,674,812; 9,678,059; 9,683,974; 9,689,826; 9,696,311; 9,714,370; 20010029774; 20010041366; 20020002414; 20020004995; 20020005580; 20020014415; 20020017125; 20020045274; 20020045275; 20020081232; 20020081397; 20020098119; 20020110901; 20020131901; 20020132361; 20020141901; 20020142477; 20020149466; 20020164643; 20020178789; 20020197390; 20020198574; 20030010097; 20030024814; 20030069002; 20030083756; 20030109056; 20030109951; 20030136960; 20030144746; 20030159927; 20030165882; 20030165987; 20040018633; 20040018642; 20040029288; 20040033165; 20040042933; 20040147038; 20040192072; 20040194534; 20040200722; 20040202856; 20040204920; 20040211243; 20040215402; 20040223876; 20040237631; 20050000830; 20050016276; 20050022581; 20050048414; 20050065230; 20050072213; 20050090015; 20050121699; 20050126909; 20050131139; 20050150778; 20050159922; 20050177317; 20050202358; 20050216114; 20050241935; 20050244978; 20050263394; 20050272881; 20050280814; 20060034731; 20060053871; 20060057597; 20060099113; 20060099715; 20060124195; 20060124448; 20060144123; 20060174941; 20060208254; 20060244618; 20060249385; 20060259163; 20060275720; 20060282225; 20060292033; 20070018779; 20070095678; 20070114138; 20070117207; 20070119236; 20070126061; 20070131021; 20070142799; 20070151449; 20070180892; 20070187239; 20070229294; 20070231947; 20070235348; 20070252710; 20070252711; 20070275690; 20080003530; 20080017507; 20080025876; 20080054382; 20080077331; 20080101994; 20080103751; 20080236251; 20080245675; 20080262743; 20080278140; 20080278181; 20080319682; 20090004612; 20090007636; 20090007777; 20090049890; 20090084162; 20090090168; 20090130421; 20090148690; 20090196796; 20090201120; 20090214762; 20090216461; 20090227059; 20090234587; 20090256215; 20090260423; 20090261987; 20090263287; 20090273354; 20090309614; 20090315728; 20100001211; 20100008619; 20100060465; 20100073016; 20100102975; 20100132547; 20100140597; 20100188110; 20100191474; 20100203648; 20100204676; 20100209301; 20100225337; 20100229658; 20100272612; 20100273665; 20100276302; 20110010107; 20110015872;

20110054202; 20110081724; 20110089051; 20110098591; 20110125409; 20110127446; 20110171137; 20110184649; 20110244584; 20110246086; 20110269632; 20110286889; 20110300637; 20110320136; 20120041574; 20120050038; 20120056632; 20120071362; 20120071737; 20120090378; 20120097917; 20120143515; 20120156099; 20120165623; 20120186987; 20120212242; 20120270205; 20120282594; 20120295360; 20120301360; 20130022755; 20130040399; 20130046485; 20130059758; 20130065319; 20130126363; 20130143247; 20130158881; 20130162403; 20130171733; 20130183766; 20130210679; 20130236980; 20130236981; 20130241726; 20130259749; 20130311108; 20130315816; 20130330231; 20130338768; 20130338769; 20130338770; 20130338771; 20130338772; 20130338773; 20140015548; 20140022058; 20140083869; 20140107362; 20140127822; 20140145736; 20140151631; 20140193925; 20140208828; 20140220703; 20140242237; 20140274804; 20140275716; 20140288647; 20140296663; 20140296978; 20140318990; 20140330043; 20140347491; 20140349256; 20140349257; 20140371105; 20150076007; 20150079697; 20150082920; 20150087935; 20150101392; 20150116093; 20150126873; 20150132857; 20150168365; 20150232598; 20150268207; 20150272105; 20150273521; 20150276516; 20150276635; 20150276643; 20150276644; 20150276648; 20150276656; 20150301021; 20150309535; 20150313496; 20150320588; 20150325100; 20150327989; 20150366504; 20150370320; 20160008182; 20160011135; 20160012749; 20160018350; 20160073886; 20160095731; 20160103104; 20160110991; 20160112684; 20160140870; 20160169810; 20160195486; 20160195504; 20160209420; 20160231267; 20160232811; 20160282302; 20160290980; 20160317060; 20160349790; 20160366065; 20160370310; 20170023509; 20170038326; 20170093981; 20170110678; 20170124110; 20170135633; 20170160252; 20170162023; 20170164878; 20170167934; and 20170173262.

Each reference cited herein is expressly incorporated herein by reference in its entirety.

SUMMARY OF THE INVENTION

The ability to tune the sensing properties with nanostructured materials in a flexible scaffold is essential for constructing highly sensitive and wearable sensors or biosensors, especially for secretions, e.g., from skin or mucous membranes. Flexibility provides an ability to conform to the surface, which is important in some applications. Dynamic flexibility can also be important. Typically, the sensor should remain in close contact with the source of the secretion, for example to avoid void space, to speed response, and assure measurement of the secretion itself. It is noted that the sensors provided herein are not limited to biological secretions from skin and mucous membranes, and the form factor of the sensor may be provided based on its application. For example, the sensor may be provided as an implant or intravascular device, in which case the sensor would measure the surrounding medium.

The assembly of functional nanoparticles into nanofibrous membranes represents a new strategy for constructing flexible composite materials with multifunctional and tunable properties. Examples of the scaffold papers or membranes include Whatman filter paper or membrane filter, Minipore filter paper, Fisherbrand paper, Ivory Linen paper, etc. Generally, a suitable paper is chemically pulped cellulose fiber, with no additives or finishes. Commercially-available technical papers may therefore be suitable. One implementation provides a nanocomposite scaffold derived from assembling gold nanoparticles (Au NPs) in a multi-layered nanofibrous membrane through controllable interactions with molecular linking and polymeric electrostatic binding.

A preferred embodiment includes a 3-layer structured membrane consisting of cellulose nanofibers (CN), cross-linked polyethylene glycol diacrylate (PEGDA) and nonwoven polyethylene terephthalate (PET) layers, utilized in combination with either 11-mercaptoundecanoic acid (MUA) as a molecular linker with hydrogen-bonding groups for interlinking alkanethiolate-capped Au NPs or poly(diallyl ammonium) (PDA) as a matrix with positively-changed groups for anchoring negative-charge capped Au NPs.

In one embodiment, gold nanoparticles (Au NPs) are provided in a multilayered fibrous membrane consisting of cellulose nanofiber (CN) top layer (fiber diameter 5 nm), electrospun polyacrylonitrile (PAN) nanofibrous midlayer (fiber diameter 150 nm), and nonwoven polyethyleneterephthalate (PET) fibrous support layer (fiber diameter 20 µm) through interparticle molecular/polymeric linkages and nanoparticle-nanofibrous interactions. 11-mercaptoundecanoic acid (MUA) may be used as a molecular linker having hydrogen-bonding groups for interlinking alkanethiolate-capped Au NPs. Poly(diallyldimethylammonium) (PDA) may be used as a matrix with positively changed groups for anchoring negative-charge capped Au NPs.

Impedance measurements of the nanocomposite membrane (Au NPs/CN/PAN/PET) as a scaffold on chemiresistor-type platforms demonstrate the viability of detecting ionic species in solutions with dissolved salts with different cations and changes of relative humidity in gas phase.

The sensor may be made specific for particular ions, solutes, reagents, or conditions by control over the nanoparticles, the fibers themselves and the arrangement of fiber layers, the environment of use, chemispecific reagents, etc.

This type of nanoparticle-nanofibrous scaffold is further demonstrated as a flexible sensor strip for detecting changes in sweating and perspiration for volunteers before and after exercise. The sensitivity of the electrical responses in this case depends on the nature of molecular interactions in the nanocomposite materials.

In comparison with existing sensor or biosensor thin film technologies, the new type of nanocomposite scaffolds enables tunable sensitivity and selectivity, controllable permeation of water, device flexibility and wearability, and low-cost manufacturing capability.

In comparison with traditional 2D sensing materials in most previous studies of sweat sensors, a 3D scaffold offers intriguing opportunities to address some of the current challenges. Specifically, the incorporation of assemblies of functional nanoparticles into flexible paper or membrane such as nanofibrous membranes represents a new pathway for constructing flexible sensors with tunable and multifunctional properties.

This new technology features new nanocomposite types of scaffolds consisting of functionalized gold nanoparticles and fibrous scaffolds. These types of nanocomposite are demonstrated to function as sensitive materials on a flexible platform for sensor and biosensor applications. The flexible and printable characteristics of nanocomposite scaffolds also feature device flexibility and wearability, and low-cost manufacturing capability.

The nanoparticles may be selectively deposited on the membrane using an additive manufacturing process (e.g., pad printing, mask printing, 3D printing), to pattern the sensor. On the other hand, in some cases, a homogeneous distribution of nanoparticles may be altered after deposition by a selective poisoning, disruption or inactivation, to provide a physical pattern. For example, there the functioning of the sensor is dependent on characteristics of an organic linker or ligand, the organic linker or ligand may be of a type which is degraded by UV light, and thus susceptible to mask-illumination patterning. Further, the hydrophilicity of the fiber matrix surrounding the nanoparticles may be important, and the hydrophilicity/hydrophobicity of one or more of the fiber layers may be controlled or modified before or after the nanoparticles are deposited, e.g., by deposition of a hydrophobicity modulating agent, oxidation or surface modification of the fibers, etc. One reason for patterning the sensor is to control the impedance and sensitivity. In a large area sensor, the output tends to be the average response across the area. On the other hand, a patterned sensor may place regions of the sensor in series with one another, resulting in a long effective sensing distance, and increased sensitivity to regional effects. Another practical reason for patterning is to facilitate electrical connection of the sensor. Another reason is to provide separate sensing channels for different analytes. For example, the patterning may include a gradation of a physical, chemical, or biological property, so that an array of sensor elements is provided with a range of sensing characteristics.

Impedance measurements of the nanocomposite membrane (AuNPs/CN/PEGDA/PET) as a scaffold of chemiresistor platform demonstrated the viability of detecting ionic species in solutions with dissolved salts (e.g., NaCl and KCl) and changes of relative humidity in the atmosphere. This nanoparticle-nanofiber sensor platform is further demonstrated as a flexible sensor strip for detecting changes in sweating and perspiration for individuals before and after excises. These are, of course, prototype applications, and the sensor is not limited to these examples.

A nanocomposite scaffold is fabricated by the assembly of functionalized gold nanoparticles (Au NPs) in a layered nanofibrous membrane through controlled molecular linking and polymeric electrostatic binding interactions. This technology features the nanomaterials of functionalized gold nanoparticles and their assemblies through controlled molecular linking and polymeric electrostatic binding interactions, and the thin-film nanofibrous-cellulose composite membranes with controllable porosity and high permeation flux of water. It is noted that gold nanoparticles are environmentally stable, and thus provide a basis for a durable sensor. However, other types of nanoparticles may be employed, subject to their chemical biolochemical reactivity as a possible advantage or disadvantage.

A preferred class of nanofibrous membranes consists of three-layered structures including a cellulose nanofiber (CN) top layer (fiber diameter around 5 nm), electrospun polyacrylonitrile (PAN) midlayer (fiber diameter around 150 nm), and nonwoven polyethylene terephthalate (PET) substrate layer (fiber diameter around 20 μm), featuring a combination of nano- and microporosities with extremely high surface to volume ratio. Cross-linked polyethylene glycol diacrylate (PEGDA) may be used in place of PAN. To impart electrically responsive function to the nanofibrous membrane toward chemical or biosensing sensing, molecularly mediated nanoparticles assembled in a thin film offer highly tunable molecular interactions and electrical properties.

The present technology provides nanocomposite scaffolds structured by assembling gold nanoparticles (Au NPs) in a flexible multilayered nanofibrous membrane through interactions involving molecular linkage and electrostatic binding.

In one exemplary embodiment, 11-mercaptoundecanoic acid (MUA) was used as a molecular linker with hydrogen-bonding groups for interlinking alkanethiolate-capped Au NPs. In another exemplary embodiment, poly(diallyl ammonium) (PDA) was used as positively-charged matrix for anchoring negative-charge capped Au NPs. The derivatized nanoparticles have an affinity for the fibers, and can be used to assemble a three-layer structured membrane consisting of cellulose nanofiber (CN), cross-linked polyethylene glycol diacrylate (PEGDA) and nonwoven (PET) layers. The resulting membranes were demonstrated as sensitive scaffolds on sensor and biosensor devices for detection of humidity, ionic or biologically-relevant chemical species. The materials have been demonstrated for applications in water contaminants monitoring, sweat monitoring, etc. One example involves using the nanocomposite membrane as a scaffold for detecting ionic species in solutions and changes of relative humidity in the atmosphere. It functions as a sweat sensor strip for detecting changes in sweating and perspiration to provide diagnostic information.

In one embodiment, a CN (thickness <2 μm)/PAN (thickness 40 μm)/PET (thickness 100 μm) three-layer membrane was utilized in combination with assemblies of Au NPs, with different nanoparticle-nanofibrous interactions. One involves 11-mercaptoundecanoic acid (MUA) as a molecular linker having hydrogen-bonding groups for interlinking alkanethiolate-capped Au NPs. Another features poly-(diallyldimethylammonium) (PDA) as a matrix with positively charged groups for anchoring negative-charge capped Au NPs.

These sensors are effective for detection of chemical species relevant to sweating or perspiration, such as moisture and ionic species, demonstrating the viability of potential applications of a new class of nanoparticle-nanofibrous membranes in wearable sweat sensors.

It is an object to provide a sensor, comprising a nanofibrous layer having nanofibers coated with adherent nanoparticles which are derivatized to specifically interact an analyte, to produce an electronic or optical response. The response of the nanoparticles to the analyte is qualitatively different from freely suspended nanoparticles as a result of local interaction with the nanofibers, and is dependent on the derivatization. The nanofibers may also be derivatized to tune the response.

It is an object to provide a chemical sensor, comprising: a sensing medium, comprising a nanofibrous layer and a plurality of nanoparticles, coating nanofibers within the nanofibrous layer, the plurality of nanoparticles being derivatized to interact with the nanofibrous layer and an analyte in a medium, based on at least one of electronic charge, ligand coordination, hydrogen bonding, van der Waals force, polarity, hydrophilicity, and hydrophobicity; and an electrode, configured to sense a state of the sensing medium in response to the analyte in the medium, and to produce an electrical signal output corresponding to the state.

The nanofibrous layer may comprise nanofibrous cellulose. The nanofibrous layer may comprise a porosity of between 10-99%.

The nanofibrous layer may be supported on a permeable layer, e.g., an electrospun fiber layer. The nanofibrous layer may be supported on at least one of a permeable crosslinked polyacrylonitrile (PAN) layer and a permeable crosslinked polyethylene glycol diacrylate (PEGDA) layer. The chemical sensor may further comprise an electrospun fiber permeable layer supporting the nanofibrous layer. The permeable layer may be a crosslinked polyacrylonitrile (PAN) layer or crosslinked polyethylene glycol diacrylate (PEGDA) layer supporting the nanofibrous layer. The permeable layer may be supported on non-woven layer. The nanofibrous layer may be cast from a slurry on an electrospun layer formed on a nonwoven layer.

The sensing medium may comprise the nanofibrous layer having a fiber diameter of less than about 15 nm, supported on a fibrous intervening layer having a fiber diameter of less than about 250 nm, on a flexible support layer.

The nanoparticles may be gold or other metallic nanoparticles. The derivatized nanoparticles may be charged. The plurality of nanoparticles may be at least one of: linked to a thiolate; hydrogen bonded to 11-mercaptoundecanoic acid (MUA) within the nanofibrous layer; linked to a carboxylic acid; and electrostatically bound to poly(diallyl) ammonium) within the nanofibrous layer. The thiolate may be an organic thiolate, such as an alkane thiolate.

The electrical signal output may be selectively responsive to moisture, water, solute concentration, ions, monovalent cations, polyvalent cations, or other organic or inorganic analytes.

The electrode may comprise a printed or otherwise deposited or formed conductive element or patter, for example a pair of interdigitated conductive traces spaced across a gap to sense a change in conductivity or capacitance of the nanofibrous layer coated with the nanoparticles.

The electrical signal output may be fed to an electronic circuit receiving the electrical signal output, configured to determine a quantitative parameter of the analyte. The sensor may be resistive, voltometric; impedometric; amperometric; capacitive; potentiostatic or other 3-electrode configuration, enzymatic, redox, or the like. The sensor may have a measurable response to the analyze over a range from, e.g., 0 to 100 mM. The response may be linear, non-linear, logarithmic, or other response function.

It is also an object to provide a sensor, comprising: a sensing medium, comprising a fibrous layer and a plurality of nanoparticles, coating fibers within the fibrous layer, the plurality of nanoparticles being derivatized to interact with the fibrous layer and an analyte in a medium, based on at least one of electronic charge, ligand coordination, hydrogen bonding, van der Waals force, polarity, hydrophilicity, and hydrophobicity; and an electrode, configured to sense a state of the sensing medium in response to the analyte in the medium, and to produce an electrical signal output corresponding to the state. The fibrous layer may comprise nanofibers, e.g., nanofibrous cellulose. The fibrous layer may also comprise a natural cellulose fiber paper, such as a filter or membrane paper.

The sensor may comprise a permeable layer, and a non-woven layer, the permeable layer being supported on the nonwoven layer, and the fibrous layer being supported on the permeable layer, wherein permeable layer consists essentially of fibers having a diameter larger than a diameter of the fibers within the fibrous layer, and fibers of the nonwoven layer have a larger diameter than fibers of the permeable layer.

The sensor may have a monotonically increasing response to a concentration an ionic species within the analyte over a range from 0 to 100 mM.

It is also an object to provide a method of sensing an analyte, comprising: providing a sensor, comprising an electrode for sensing an electrical state of a sensing medium, and producing as an output an electrical signal corresponding to the state, the sensing medium comprising a fibrous layer and a plurality of nanoparticles, coating fibers of the fibrous layer, the plurality of nanoparticles being derivatized to interact with the nanofibrous layer alter the electrical state of the sensing medium in response to the analyte, based on at least one of an electronic charge, hydrogen bonding, van der Waals force, polarity, hydrophilicity, and hydrophobicity; exposing the sensor to the analyte; and producing the output, dependent on the electrical state of the sensing medium.

It is a further object to provide a method of manufacturing a sensing medium, comprising a nanofibrous layer and a plurality of nanoparticles supported on and embedded in the nanofibrous layer, comprising: providing derivatized insoluble conductive nanoparticles having a diameter less than about 150 nm, the derivatized insoluble conductive nanoparticles being derivatized with a ligand capable of at least one of ionic bonding, hydrogen bonding, and van der Waals bonding; providing organic nanofibers in an aqueous slurry, having a nanofiber diameter of less than about 15 nm, and having exposed groups capable of at least one of ionic bonding, hydrogen bonding, and van der Waals interaction with the derivatized insoluble conductive nanoparticles; providing a fibrous layer having a fiber diameter of between about 5-250 nm, deposited on a non-woven fibrous substrate; casting a layer of the organic nanofibers in the aqueous slurry onto the non-woven fibrous substrate, under conditions which cause the organic nanofibers in the aqueous slurry to gel and remain on a surface of the non-woven fibrous substrate or fibrous layer; and depositing a solution containing the nanoparticles on the layer of the organic nanofibers, to link the nanoparticles with nanofibers within the layer of the organic nanofibers, by at least one of electrostatic bonding, hydrogen bonding, and van der Waals interaction, to thereby produce the sensing medium, comprising a nanofibrous layer, on the non-woven fibrous substrate or the fibrous layer, and a plurality of nanoparticles, coating and interacting with nanofibers within the nanofibrous layer. The layer of organic nanofibers may be cast on the non-woven fibrous substrate as a gel which remains on a surface of the fibrous layer substantially without invading the interior of the non-woven fibrous substrate.

It is also an object to provide a method of sensing an analyte, comprising: providing a sensor, comprising an electrode for sensing an electrical state of a sensing medium, and producing as an output an electrical signal corresponding to the state, the sensing medium comprising a nanofibrous layer and a plurality of nanoparticles, supported on and embedded in the nanofibrous layer, and coating fibers of the nanofibrous layer, the plurality of nanoparticles being derivatized with at least one composition configured to interact with the nanofibrous layer and the analyte to alter the electrical state of the sensing medium, based on at least one of an electronic charge, hydrogen bonding, van der Waals force, polarity, hydrophilicity, and hydrophobicity; exposing the sensor to the analyte; and producing the output, dependent on the electrical state of the sensing medium.

It is an object to provide a chemical sensor, comprising: an electrode, configured to sense an electrical state of an adjacent sensing medium in response to a chemical in the surrounding environment, and to produce as an output an electrical signal corresponding to the state; and a sensing medium, comprising: a nanofibrous layer; and a plurality of nanoparticles, supported on and imbedded in the nanofibrous layer, and coating fibers of the nanofibrous layer, each nanoparticle being derivatized with at least one composition configured to interact with the nanofibrous layer and a chemical based on at least one of electronic charge, ligand coordination, hydrogen bonding, van der Waals force, polarity, hydrophilicity, and hydrophobicity.

It is another object to provide a method of sensing a chemical or biological agent, comprising: providing a sensor, comprising an electrode for sensing an electrical state of a sensing medium, and producing as an output an electrical signal corresponding to the state, and the sensing medium comprising a fibrous or nanofibrous layer and a plurality of nanoparticles, supported on and embedded in the nanofibrous layer, and coating fibers of the fibrous or nanofibrous layer, the plurality of nanoparticles being derivatized with at least one composition configured to interact with the fibrous or nanofibrous layer and the chemical to alter the electrical state of the sensing medium, based on at least one of an electronic charge, hydrogen bonding, van der Waals force, polarity, hydrophilicity, and hydrophobicity; inducing an electrical potential in the sensing medium; and producing the output, dependent on the electrical state of the sensing medium.

It is a further object to provide a method of manufacturing a sensing medium, comprising a nanofibrous layer and a plurality of nanoparticles supported on and embedded in the nanofibrous layer, comprising: providing insoluble conductive nanoparticles derivatized with an organic ligand, capable of at least one of ionic bonding, hydrogen bonding, and van der Waals bonding, having a diameter less than about 150 nm; providing organic nanofibers in an aqueous slurry, having a nanofiber diameter of less than about 15 nm, and having exposed groups capable of at least one of ionic bonding, hydrogen bonding, and van der Waals interaction; providing a fibrous layer having a fiber diameter of between about 50-250 nm, deposited on a non-woven fibrous substrate; casting a layer of the organic nanofibers in the aqueous slurry onto the spun non-woven fiber layer, under chemical conditions which cause the organic nanofibers in the aqueous slurry to gel and remain on a surface of the spun non-woven fiber layer; and depositing a solution containing the nanoparticles on the layer of the organic nanofibers, to bond the nanoparticles with nanofibers within the layer of the organic nanofibers, by at least one of electrostatic bonding, hydrogen bonding, and van der Waals interaction.

The sensing medium may comprise the nanofibrous layer having a fiber diameter of less than about 15 nm, on a fibrous intervening layer having a fiber diameter of less than about 250 nm, on a flexible support layer. The electrode may be a printed electrode formed on the nanofibrous layer, the fibrous intervening layer, or the flexible support layer.

The output may be selectively responsive to moisture, humidity, monovalent cations, divalent cations, multivalent cations, sodium ions, and/or potassium ions. The output may form part of a chemiresistive or chemi-capacitive sensor. The nanoparticles and nanofibrous layer may selectively interact with a chemical based on a chemically charged species in the chemical.

The electrode may comprise a pair of interdigitated conductive traces spaced across a gap to sense a change in conductivity of the nanofibrous layer coated with the nanoparticles. The electrode may comprise a platinum interdigitated microsensor electrode. The electrode may comprise a printed ink, a printed carbon ink, graphite or a graphene ink.

The chemical sensor may be provided in combination with an electronic circuit configured to determine a qualitative parameter of the chemical, or an electronic circuit configured to determine a quantitative parameter of the chemical. The output may correspond to an amount of sweat or perspiration secreted from human skin adjacent to the sensing medium.

The chemical sensor may have a non-linear response of impedance to analyze a concentration of the chemical over a range from 0 to 100 mM, a linear response of impedance to analyze a concentration of the chemical over a range from 10 to 100 mM, and/or a sensitive response to a range of chemical concentration over a range from at least 20 mM to 60 mM.

The nanoparticles may be metallic nanoparticles, or gold nanoparticles, or metallic nanoparticles which are stable in an aqueous solution containing the chemical. The nanoparticles may be negatively charged or positively charged.

The insoluble conductive nanoparticles may comprise gold nanoparticles capped with decanethiolate shells, alkylthiolate shells, acrylate shells, or citrate shells. The nanoparticles may be gold or another metal, linked to an alkanethiolate, such as decanethiolate (DT). The plurality of nanoparticles may be hydrogen bonded to 11-mercaptoundecanoic acid (MUA) within the nanofibrous layer. The plurality of nanoparticles may be linked to a carboxylic acid. The plurality of nanoparticles may be electrostatically bound to poly(diallyl) ammonium) within the nanofibrous layer. The plurality of nanoparticles may be derivatized with at least one composition configured to interact with the nanofibrous layer and the chemical based on at least electronic charge, ligand coordination, hydrogen bonding, van der Waals force, polarity, hydrophilicity, and/or hydrophobicity.

The nanoparticles may be about 1, 2, 3, 4, 5, 6, 7, 8, 9, 10, 12, 15, 17, 20, 25, 30, 35, 40, 42, 45, 50, 55, 60, 65, 70, 75, 80, 90, 100, 110, 120, 125, 130, 140, 150, 160, 170, 180, 190, or 200 nm in diameter.

The insoluble conductive nanoparticles may have a size distribution of less than ±20%, ±17.5%, ±15%, +10%, ±7.5%, ±5%, ±3%, or ±2.5%.

The nanofibrous layer may comprise nanofibrous cellulose and/or oxidized cellulose nanofibers, e.g., having a fiber diameter of about 1, 2, 3, 4, 5, 6, 7, 8, 9, 10, 15, 20, 25, 30, 35, 40, 45, 50, 50, 70, 80, 90, 100, 125, 150, 200, 250, 300, 350 or 400 nm. The nanofibrous layer may comprise nanofibrous cellulose having a fiber diameter of between about 1 nm to 400 nm, about 1-100 nm, about 2-50 nm, or about 5-25 nm.

The nanofibrous layer may comprise nanofibrous cellulose having a controlled porosity. The nanofibrous layer may comprise a porosity of between 10-99%, about 10%, about 20%, about 30%, about 40%, about 50%, about 60%, about 70%, about 80%, about 90%, about 95%, about 97%, about 99%, or about 60-90%.

The nanofibrous layer may be supported on a permeable layer. The permeable layer may be electrospun, and/or formed of crosslinked polyacrylonitrile (PAN) or crosslinked polyethylene glycol diacrylate (PEGDA). The permeable layer may be supported on a nonwoven layer. The nonwoven layer may comprise polyethylene terephthalate. The nonwoven layer may consist of nonwoven polyethylene terephthalate (PET). The nanofibrous layer may be supported on a crosslinked PAN or PEGDA permeable layer, and the permeable layer may be supported on a PET nonwoven layer.

The nanofibrous layer may be cast from a slurry on an electrospun layer formed on a nonwoven layer. The layer of organic nanofibers may be cast on the fibrous layer as a gel which remains on a surface of the layer of organic nanofibers substantially without invading the interior of the fibrous layer. The chemical conditions which cause the organic nanofibers in the aqueous slurry to gel and remain on a surface of the spun non-woven fiber layer may comprise a pH of less than 3, 2.5, or 2.

The solution deposited containing the nanoparticles on the layer of the organic nanofibers may comprise a molecular linker with hydrogen-bonding groups for interlinking the nanoparticles with the organic ligand. The solution deposited containing the nanoparticles on the layer of the organic nanofibers may comprise 11-mercaptoundecanoic acid (MUA). The solution deposited containing the nanoparticles on the layer of the organic nanofibers may comprise a molecular linker with positively charged groups for ionically interlinking nanoparticles with the organic ligand. The solution deposited containing the nanoparticles on the layer of the organic nanofibers may comprise poly(diallyl ammonium) (PDA).

BRIEF DESCRIPTION OF THE DRAWINGS

FIG. 1A shows nanoparticles on the CN and PAN fibers and FIG. 1B shows a magnified image of the nanoparticles on the PAN fibers.

FIG. 3A shows $1/|Z|$ vs concentration curves obtained from Bode impedance plots at 1 kHz; FIG. 3B shows $1/R$ values obtained by semicircle fit to Nyquist impedance plots with MUA-AuNPs/CN/PAN/PET NM on Pt-IME in solutions of K+ (a), Na+ (b), and Li+ (c) as a function of concentration.

FIG. 4A shows plots of $1/|Z|$ values with G-PE on the PET side; FIG. 4B shows plots of $1/|Z|$ values with G-PE on the CN side.

FIG. 5A shows plots in response to water (as a control); FIG. 5B shows plots in response to sweat (perspiration test).

FIG. 7A shows data for scaffolds derived from PDA of constant concentration and Au NPs (70 nm) of different concentrations ($5.0\times10^{10}$ (a), $2.0\times10^{11}$ (b), and $1.0\times10^{11}$ NPs/mL (c), Slopes: $-2.3\times10^{-2}$ (a); $-2.0\times10^{-2}$ (b); and $-4.5\times10^{-2}$ (c)); FIG. 7B shows data for scaffolds derived from PDA with different concentrations (0.4 M (a) and 0.76 M (b)) and the same concentration of Au NPs (70 nm, $5.0\times10^{10}$ NPs/mL, Slopes: $-2.8\times10^{-2}$ (a); and $-3.1\times10^{-2}$ (b)); FIG. 7C shows data for scaffolds derived from PDA of the same concentration (0.4 M) and Au NPs of two different sizes (70 nm (a) and 42 nm (b)). (Slopes: $-2.6\times10^{-2}$ (a) and $-3.6\times10^{-2}$ (b).)

FIG. 8A shows sensor responses before exercise; FIG. 8B shows sensor responses after exercise; FIG. 8C shows a calibration curve for the same sensor device with controlled RH % in air (slope: $2.0\times10^{-2}$).

FIG. 9A shows illustrations of the Nanofibrous Membrane (NM), Gold Nanoparticles and Molecular/Polymeric Linkers.

FIG. 9B shows the Nanocomposite Scaffolds by Molecularly-Mediated Hydrogen-Bonding Linkages of Au NPs (M-NPs) or Polymer-Mediated Electrostatic Linkages of Au NPs (P-NPs) in the NM.

FIG. 10A shows the membrane being placed on top of a Pt IME/glass device; FIG. 10B shows the membrane with graphite printed electrodes (G-PE) in which G-PE is on either the CN or PET side (from left to right); FIG. 10C shows a cross section of the manifold with embedded flow channels and a sample-holding plate with electrical leads for impedance measurement under controlled liquid flow, for e.g., for detection of metal ions, or gas flow, e.g., for detection of relative humidity; FIG. 10D shows a patch with a thin nonwoven scaffold between the membrane and the wrist skin for sweat detection; and FIG. 10E shows a mini-compartment where the NM is placed above the palm for perspiration detection.

FIG. 16A shows data for scaffolds derived from PDA of fixed concentration and Au NPs (70 nm) of different concentrations ($5.0\times10^{10}$ (a), $2.0\times10^{11}$ (b), and $1.6\times10^{11}$ NPs/mL (c)); FIG. 16B shows data for scaffolds derived from PDA of different concentrations (0.4 M (a) and 0.76 M (b)) and the same concentration of Au NPs (70 nm, $5.0\times10^{10}$ NPs/mL); FIG. 16C shows data for scaffolds derived from PDA of the same concentration (0.4 M) and Au NPs of two different sizes (70 nm (a) 42 nm Au NPs (b)).

FIG. 17A shows sweat detection from forearm; FIG. 17B shows perspiration detection from hand, before and after exercise.

FIGS. 20E-20F show TEM images for a sensor device with gold nanoparticles with dendrons (AuNPs@dendrons) embedded in CN/PAN/PET paper as sensing scaffold.

DETAILED DESCRIPTION OF THE PREFERRED EMBODIMENT

Example 1

Figure 1A:
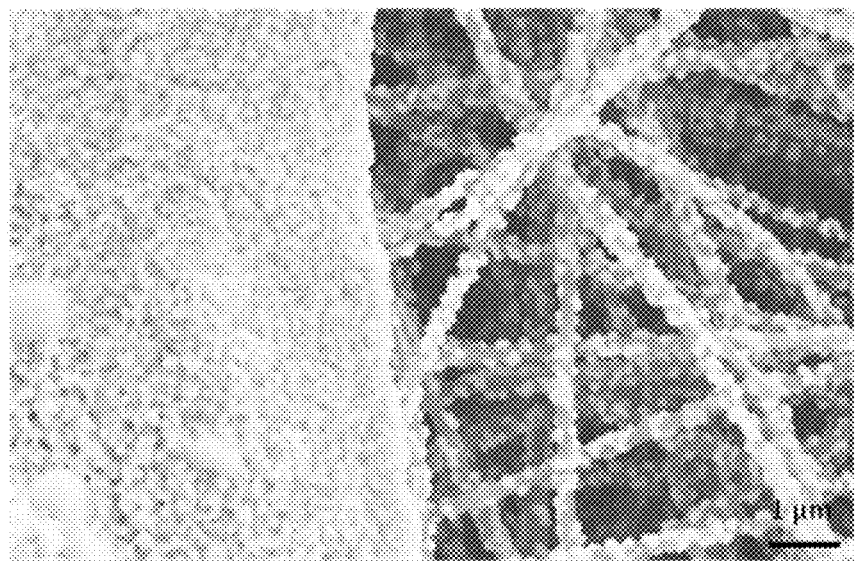
FIGS. 1A and 1B show SEM images of MUA-mediated assembly of DT-capped 7 nm Au NPs (M-NPs/NM) in CN/PAN/PET membrane.

Experimental Section
Chemicals and Synthesis of Gold Nanoparticles.

Hydrogen tetrachloroaurate trihydrate (99%), tetraoctylammonium bromide (99%), decanethiol (DT, 96%), sodium borohydride (99%), 11-mercaptoundecanoic acid (MUA, 95%), (poly)diallyldimethylammonium (PDA) (20%), sodium acrylate, sodium chloride (NaCl), potassium chloride (KCl), lithium chloride (LiCl), and graphite powders were purchased from Aldrich. Solvents included hexane (Hx, 99.9%) and toluene (Tl, 99%) from Fisher, and ethanol (99.9%) from Aldrich. Water was purified with a Millipore Milli-Q water system. 2,2,6,6-Tetramethylpiperidinooxy (TEMPO, 98%) was purchased from Acros. Sodium hypochlorite (NaClO solution, available chlorine 7-10%) was purchased from Sigma-Aldrich. Sodium bromide (NaBr) was obtained from Fisher Scientific Company. Polyacrylonitrile (PAN) having an average molecular weight (Mw) of 150 kDa was purchased from Sigma-Aldrich. Poly(ethylene terephthalate) nonwoven substrate (PET microfilter F02413 with an average fiber diameter of about 30 μm) for the membrane support was provided by Freudenberg Nonwovens (Hopkinsville, Ky.).

Gold nanoparticles of 2 nm (Au2 nm) capped with decanethiolate (DT) monolayer shells were synthesized by two-phase reduction of $AuCl_4$—according to Brust's two-phase protocol and a synthetic modification. DT-capped gold nanoparticles of 7.1±1.0 nm diameter were synthesized from a thermally activated processing of Au2 nm nanoparticles (Maye, M. M.; Zheng, W.; Leibowitz, F. L.; Ly, N. K.; Zhong, C. J. Heating-induced evolution of thiolate-encapsulated gold nano-particles: a strategy for size and shape manipulation. Langmuir 2000, 16, 490-497.) Briefly, the solution containing the as-synthesized DT-Au2 nm nanoparticles was heated at 150° C. to produce larger-sized Au nanoparticles. (Maye, M. M.; Zheng, W.; Leibowitz, F. L.; Ly, N. K.; Zhong, C. J. Heating-induced evolution of thiolate-encapsulated gold nanoparticles: a strategy for size and shape manipulation. Langmuir 2000, 16, 490-497; Han, L.; Luo, J.; Kariuki, N. N.; Maye, M. M.; Jones, V. W.; Zhong, C. J. Novel interparticle spatial properties of hydrogen-bonding mediated nanoparticle assembly. Chem. Mater. 2003, 15, 29-37.) Acrylate-capped gold nanoparticles 42 nm (42.2±6.9 nm) and 70 nm (70.6±2.0 nm) were prepared by a seeded aggregative growth method. Briefly, the synthesis involves reacting mixture of Au seeds (30 nm) and $HAuCl_4$ under controlled concentrations of the reducing and capping agents, which produced acrylate-capped Au NPs of >30 nm. (Njoki, P. N.; Lim, I. I. S.; Mott, D.; Park, H. Y.; Khan, B.; Mishra, S.; Sujakumar, R.; Luo, J.; Zhong, C. J. Size correlation of optical and spectroscopic properties for gold nanoparticles. J. Phys. Chem. C 2007, 111, 14664-14669.)

Preparation of Nanofibrous Membranes.

Ultrafine cellulose nanofibers were prepared by the following procedure. In brief, 10 g of wood pulps (Biofloc 96 supplied by the Tembec Tartas factory in France) was dispersed in 192 g of water. NaBr (0.2 g) and TEMPO (0.04 g) were subsequently dissolved in the suspension. Then 30 g of 10-15% NaClO aqueous solution was added to start this reaction. The pH value of the system was adjusted in the range of 10.0-10.3 by adding sodium hydroxide (NaOH) aqueous solution (0.5 mol/L). After 24 h, the reaction was stopped by adding ethanol (10 mL). The oxidized cellulose product was purified by dialysis process. The resulting cellulose slurry was dispersed in 100 g of water by using a homogenizer (Cole Parmer, VCX-400) for 5 min. The CN concentration was determined by using a Total Organic Carbon analyzer (TOC-500, Shi-madzu Corporation).

To prepare electrospun PAN/PET substrate, PAN was dissolved in DMF at 60° C. for 2 days until the mixture became a homogeneous solution (the solution concentration was 8 wt %). The homogeneous PAN solution was electrospun onto the nonwoven PET substrate under a high electrical voltage of 20 kV. The flow rate during this electrospinning operation was 16 μL/min and the inner diameter of the spinneret was 0.7 mm. The working distance between the spinneret and the collector was 10 cm. The average fiber diameter of the electrospun nanofiber estimated from the SEM image was 150±10 nm.

To complete the three-layered fibrous membrane containing the ultrafine cellulose nanofiber top layer, the electrospun PAN/PET substrate was first immersed in an acidic aqueous solution (pH=2). The cellulose nanofiber aqueous suspension (0.05 wt %) was subsequently cast on top of the electrospun PAN nanofibrous scaffold. The low pH value was used to gel the cellulose nanofiber suspension, thus preventing the penetration of cellulose nanofibers into the electrospun scaffold. The barrier layer thickness was controlled by the gap of the casting knife. After coating, the resulting membrane was dried at room temperature and forms a uniform coating layer of CN.

Preparation of Nanoparticle-Nanofibrous Membranes.

For the assembly of MUA-linked DT-capped Au NPs in NM (M-NPs/NM), typically a controlled volume (e.g., 2 μL) of MUA mediated Au NPs solution ($7.1 \times 10^{14}$ NPs/mL) was directly deposited in the nanofibrous membrane (NM). For the assembly of PDA-linked acrylate-capped Au NPs in the NM (P-NPs/NM), a controlled volume of 10× concentrated acrylate-capped 70 nm Au NPs ($5.0 \times 10^{11}$ NPs/mL), or 2× concentrated 42 nm NPs ($2.7 \times 10^{13}$ NPs/mL), was first mixed with PDA solution (0.4 M) by sonication for 10 min. A controlled volume (2 μL) of the solution was then deposited in the NM, followed by further annealing at room temperature for at least 1 h before use.

Instrumentation and Measurements.

Electrochemical impedance spectroscopic (EIS) measurements were performed on a SP-150 single-channel potentiostat (Biologic). The spectra were recorded at open circuit in a frequency range from 100 kHz to 0.1 Hz.

Transmission electron microscopy (TEM) was employed to determine the morphology of the nanoparticles. TEM was performed on a JEOL JEM-ARM200F instrument operated at 200 kV with a spherical aberration corrector. The nanoparticle samples were suspended in hexane or water before drop casting on a carbon-coated copper grid. The samples were then dried by evaporation in ambient atmosphere.

Scanning electron microscopy (SEM) images of the nanofibrous membrane and nanocomposite were performed with a LEO-1550 (Carl Zeiss) field emission scanning electron microscope. The membrane samples were mounted on a sample holder. It was then followed by carbon-coating with a sputter coater.

Results and Discussion

General Characteristics of Nanocomposite Membranes and Devices.

FIG. 9A shows illustrations of the Nanofibrous Membrane (NM), Gold Nanoparticles and Molecular/Polymeric Linkers. FIG. 9B shows the Nanocomposite Scaffolds by Molecularly-Mediated Hydrogen-Bonding Linkages of Au NPs (M-NPs) or Polymer-Mediated Electrostatic Linkages of Au NPs (P-NPs) in the NM.

As illustrated in FIGS. 9A and 9B, two pathways have been explored for assembling Au NPs in the three-layered CN/PAN/PET membrane by either molecular linkers or polymeric electrostatic interactions. One pathway involves a molecular linker MUA, which forms molecularly mediated thin-film assembly of Au NPs (M-NPs) via hydrogen bonding. In this case, the interaction between the nanoparticle assemblies and the nanofibers feature mainly hydrophobic interactions. The other pathway involves polymeric linker PDA, which forms polymer-mediated thin film assembly of Au NPs (P-NPs) in the membrane via electrostatic interactions. In this case, the polymeric structure provides an adhesive force between the nanoparticle assemblies and the nanofibers.

Figure 13A:
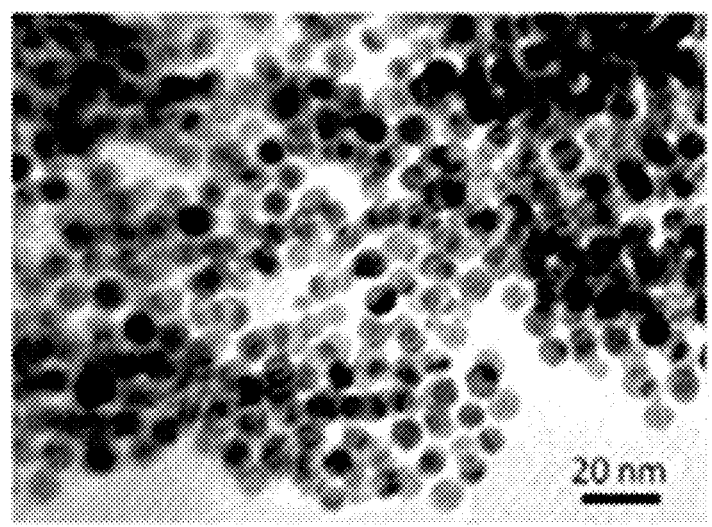
FIGS. 13A-13C show TEM images for DT-capped Au NPs (A, $7.1\pm1.0$ nm) and acrylate-capped Au NPs (B, $42.2\pm6.9$ nm, and C, $70.6\pm2.0$ nm).
Figure 13B:
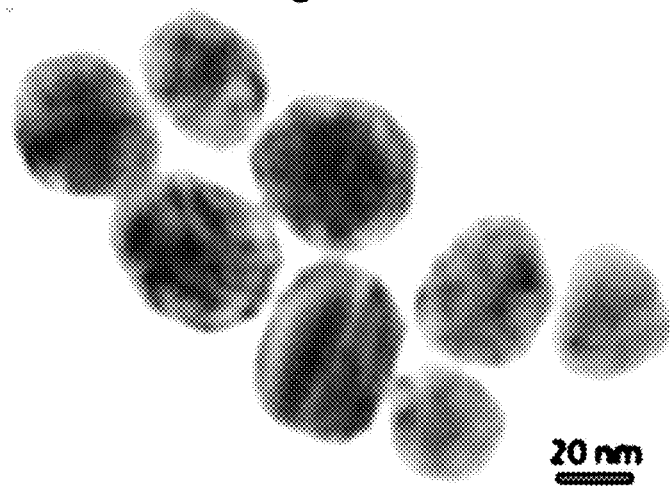
Figure 13C:
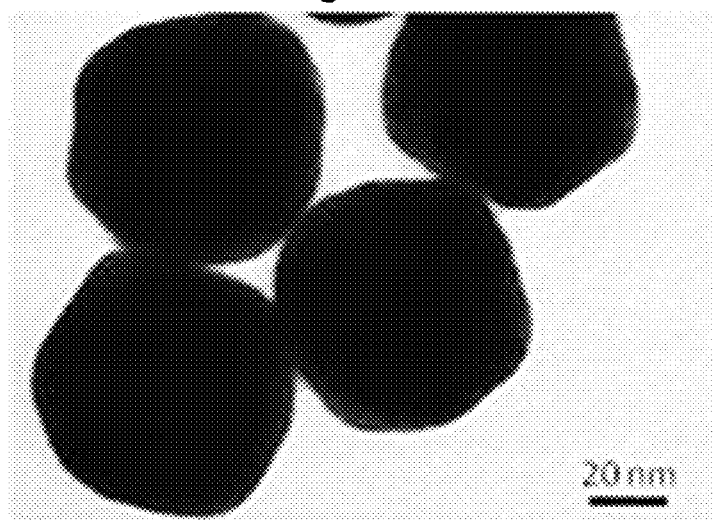

FIGS. 13A-13C show TEM images for DT-capped Au NPs (A, 7.1±1.0 nm) and acrylate-capped Au NPs (B, 42.2±6.9 nm, and C, 70.6±2.0 nm).

Figure 14A:
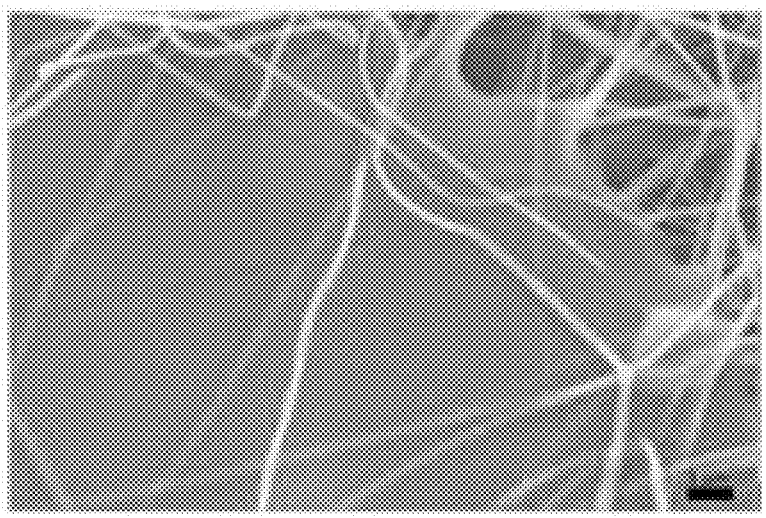
FIGS. 14A-14C show SEM images of the three-layer nanofibrous membrane.
Figure 14B:
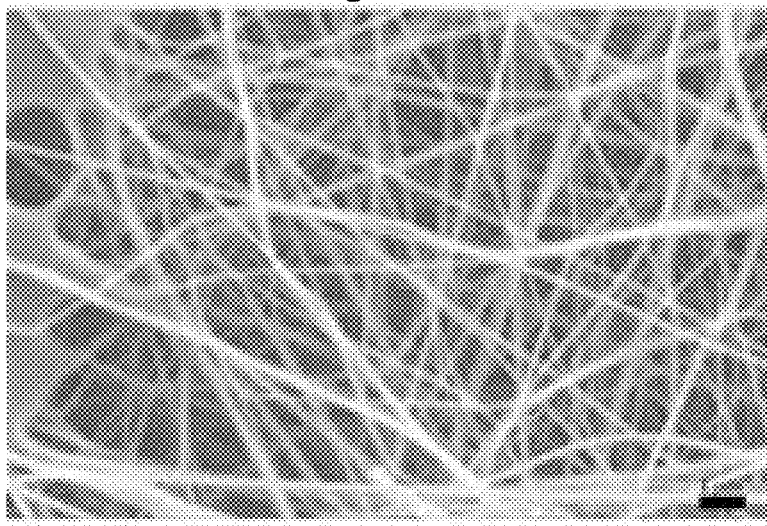
Figure 14C:
Figure 14D:
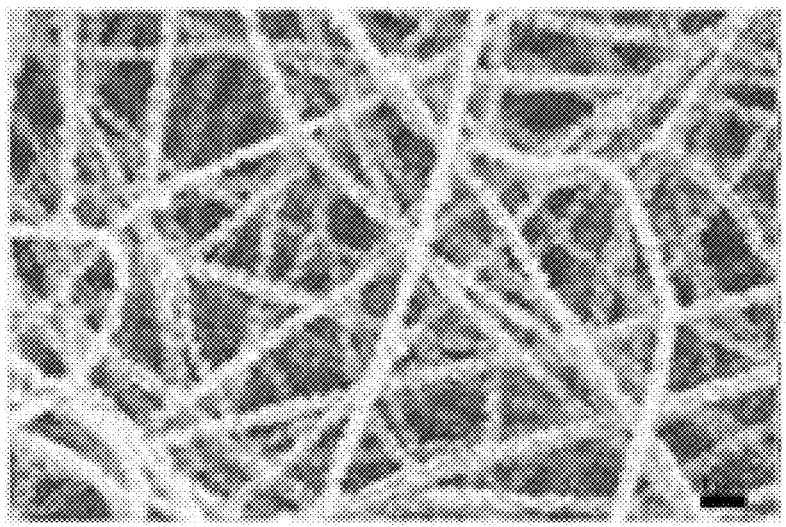
FIG. 14D shows SEM images of MUA-AuNPs (7 nm)/CN/PAN/PET.
Figure 14E:
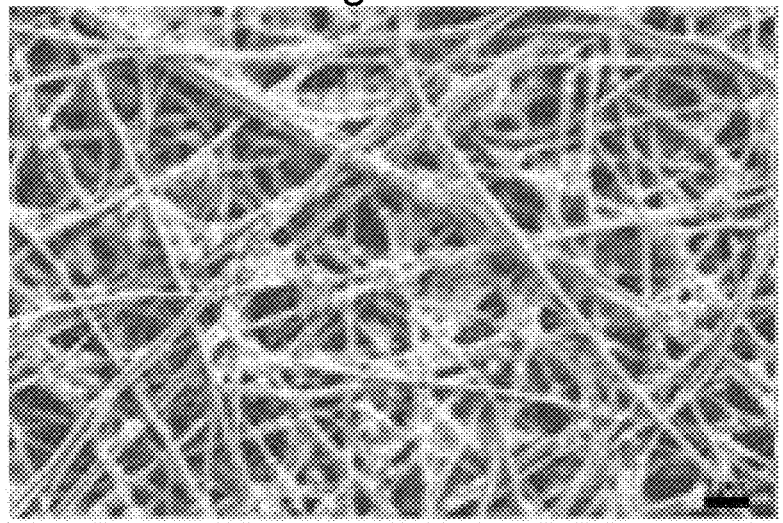
FIG. 14E shows SEM images of PDA-AuNPs (42 nm)/CN/PAN/PET.
Figure 14F:
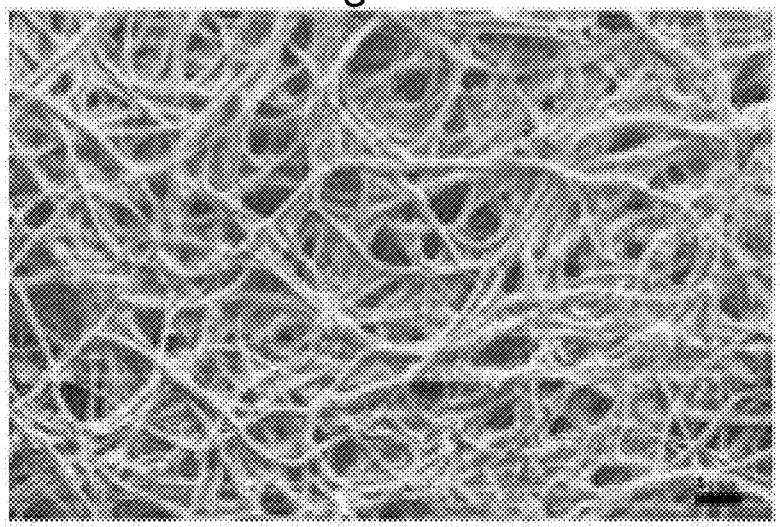
FIG. 14F shows SEM images of PDA-Au NPs (70 nm)/CN/PAN/PET.

FIGS. 14A-14F show SEM images of the three-layer nanofibrous membrane (FIGS. 14A-14C), MUA-AuNPs (7 nm)/CN/PAN/PET (FIG. 14D), PDA-AuNPs (42 nm)/CN/PAN/PET (FIG. 14E), and PDA-Au NPs (70 nm)/CN/PAN/PET (FIG. 14F).

Gold nanoparticles of different sizes and hydrophilicity characteristics were studied for their assembly in the nanofibrous membranes, including hydrophobic DT-capped Au NPs and hydrophilic acrylate-capped Au NPs (FIG. 13A). While the DT-capped Au NPs (7 nm) and acrylate-capped Au NPs (42 nm, or 70 nm) feature highly monodispersed sizes, the nanofibrous membrane features a three-layer CN/PAN/PET structure (FIGS. 14A-14C).

Figure 1B:
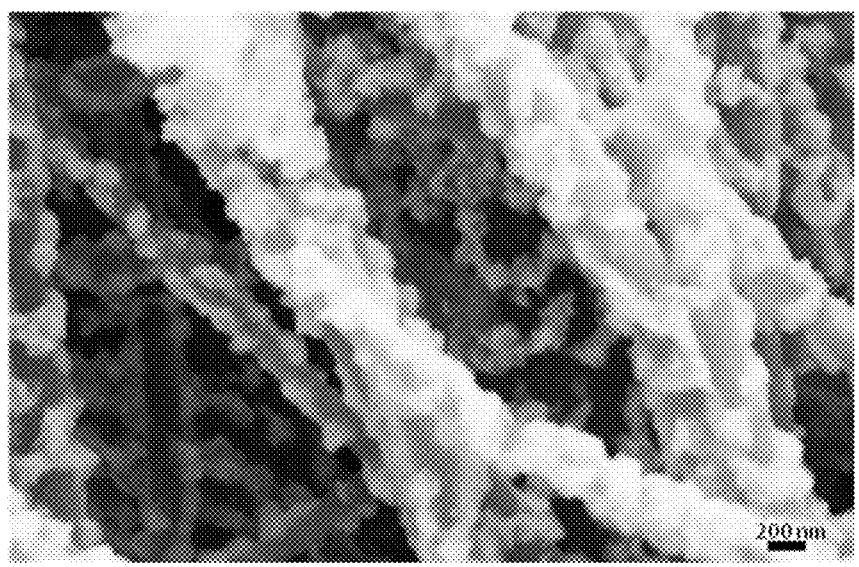

FIGS. 1A and 1B show SEM images of MUA-mediated assembly of DT-capped 7 nm Au NPs (M-NPs/NM) in CN/PAN/PET membrane: FIG. 1A shows nanoparticles on the CN and PAN fibers and FIG. 1B shows a magnified image of the nanoparticles on the PAN fibers. As shown in FIGS. 1A and 1B for the MUA-linked DT-capped 7 nm sized Au NPs in the NM (M-NPs/NM), the nanoparticles are well distributed on the surface of the CN layer and along the PAN fibers (see also FIG. 14D). Similar assemblies were also observed for PDA-linked acrylate-capped 42 or 70 nm Au NPs (P-NPs/NM) in the NM, but with a less even distribution on the fibers and a certain degree of aggregation at cross-fiber junctions (FIGS. 14E, 14F). The fact that M-NPs/NM shows a much better dispersion of NPs along the fibers than that for the P-NPs/NM indicates that the assembly depends on the surface properties of the nanoparticles and the solvent used for the assembly. Au NPs of different sizes have been assembled in the NM, but only selected examples are discussed herein for the exploration of sensing properties.

Figure 10A:
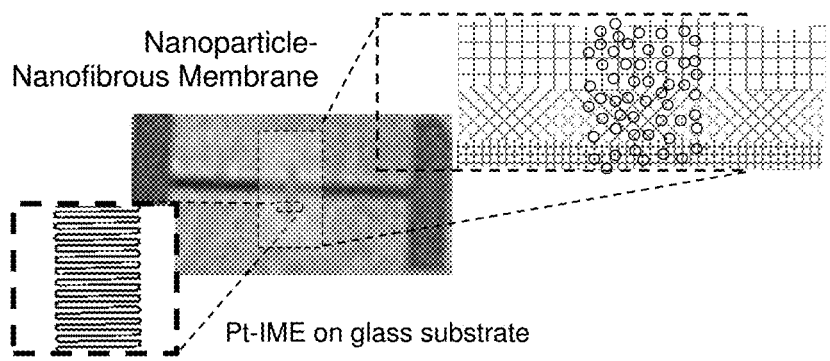
FIGS. 10A-10E show illustrations of the Nanoparticle-Nanofibrous Membrane Sensor Device and Measurement Configurations.
Figure 10B:
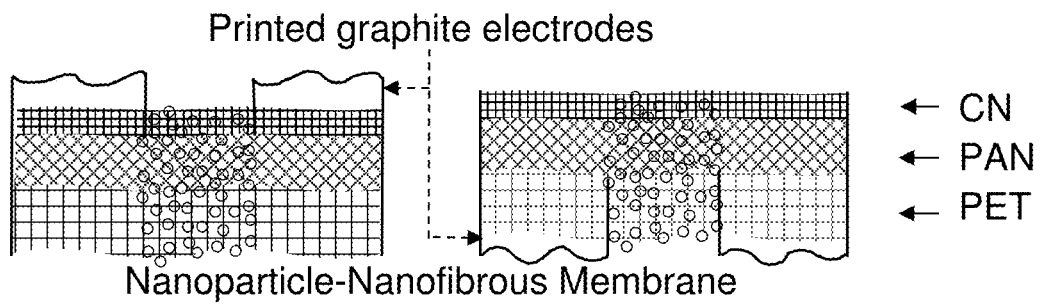
Figure 10C:
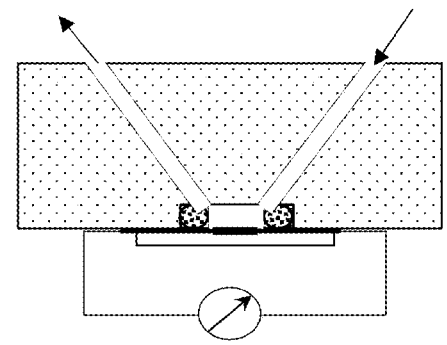
Figure 10D:
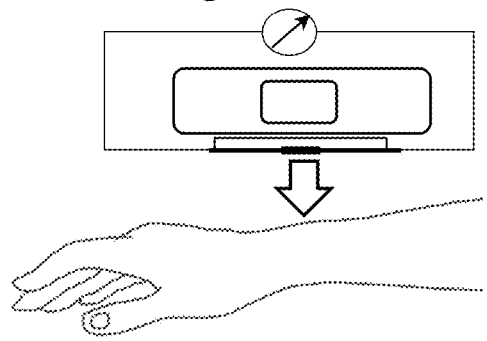
Figure 10E:
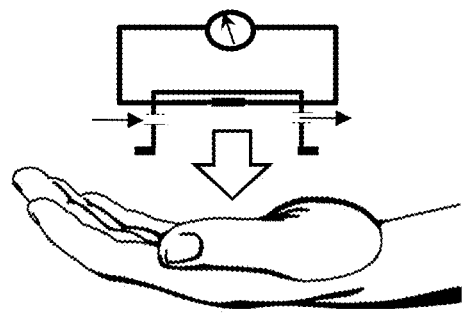

FIGS. 10A-10E show illustrations of the Nanoparticle-Nanofibrous Membrane (NM) Sensor Device and Measurement Configurations. FIG. 10A shows the membrane being placed on top of a Pt IME/glass device; FIG. 10B shows the membrane with graphite printed electrodes (G-PE) in which G-PE is on either the CN or PET side (from left to right), for impedance measurement under either liquid flow for detection of metal ions or gas flow for detection of relative humidity (C); FIG. 10C shows the manifold with embedded flow channels and a sample-holding plate with electrical leads for impedance measurement under controlled liquid or gas flow; FIG. 10D shows a patch with a thin nonwoven scaffold between the membrane and the wrist skin for sweat detection; and FIG. 10E shows a mini-compartment where the NM is placed above the palm for perspiration detection.

The M-NPs/NM, i.e., MUA-AuNPs/CN/PAN/PET, features largely hydrophobic network with partial hydrophilic domains (i.e., the region of hydrogen-bonding of carboxylic acid groups). In contrast, the P-NPs/NM, i.e., PDA-AuNPs/CN/PAN/PET, features largely hydrophilic network with partial hydrophobic polymer backbone structure. Both nanocomposite membranes were studied as resistance- or conductance-responsive scaffolds on chemiresistor-type platform via two different approaches. The first involves placing the NPs/NM on top of a prefabricated Pt-interdigitated micro-electrode (Pt-IME) device (FIG. 10A), whereas the second involves configuring the NPs/NM in between a printed pair of graphite electrodes on CN or PET sides of the membrane with a controlled gap (0.5-1.0 mm) (FIG. 10B). In each approach, the electrical responses to the analytes such as ions in a solution or moisture change in a gas atmosphere were measured by impedance spectroscopy. As illustrated in FIGS. 10C-10E, the measurements were performed in a manifold where the NM is sandwiched between manifold with embedded flow channels and a sample-holding plate with electrical leads (FIG. 10C).

Ideally, the above chemiresistor-type device can be represented by two equivalent circuit models featuring the nanoparticle—nanofibrous membrane with two-electrode configurations (see FIG. 9). One consists of two double layer capacitors (capacitance near the surface of an electrode, $C_{dl}$), one for each set of the electrodes, connected in series with a parallel combination of a membrane resistor ($R_m$) and a membrane dielectric capacitor ($C_m$), and all of them in parallel with a parasitic capacitor. The other model consists of two double layer capacitors ($C_{dl}$), connected in series with a medium resistor ($R_s$), and a dielectric capacitor ($C_{di}$).

Detection of Salts Dissolved in Water and from Sweat.

Detection of Salts in Water.

With a M-NPs/NM scaffold sensor device of M-AuNPs/CN/PAN/PET on Pt-IME (CN facing Pt-IME, FIG. 10A) placed in the test manifold (FIG. 10C), solution samples of K+, Na+, and Li+ with a common anion (Cl—), prepared by dissolving KCl, NaCl or LiCl in aqueous solutions with controlled concentrations, were introduced by a flow controller.

Figure 2A:
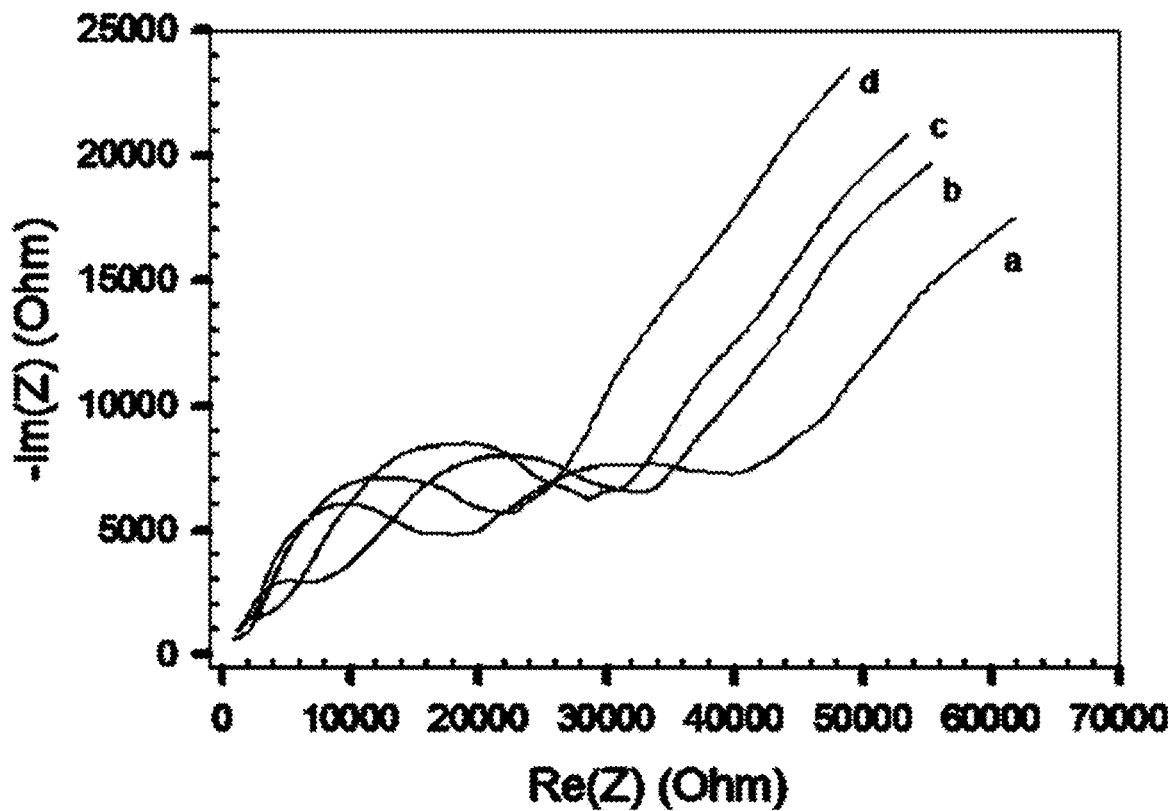
FIG. 2A shows a Nyquist impedance plot.
Figure 2B:
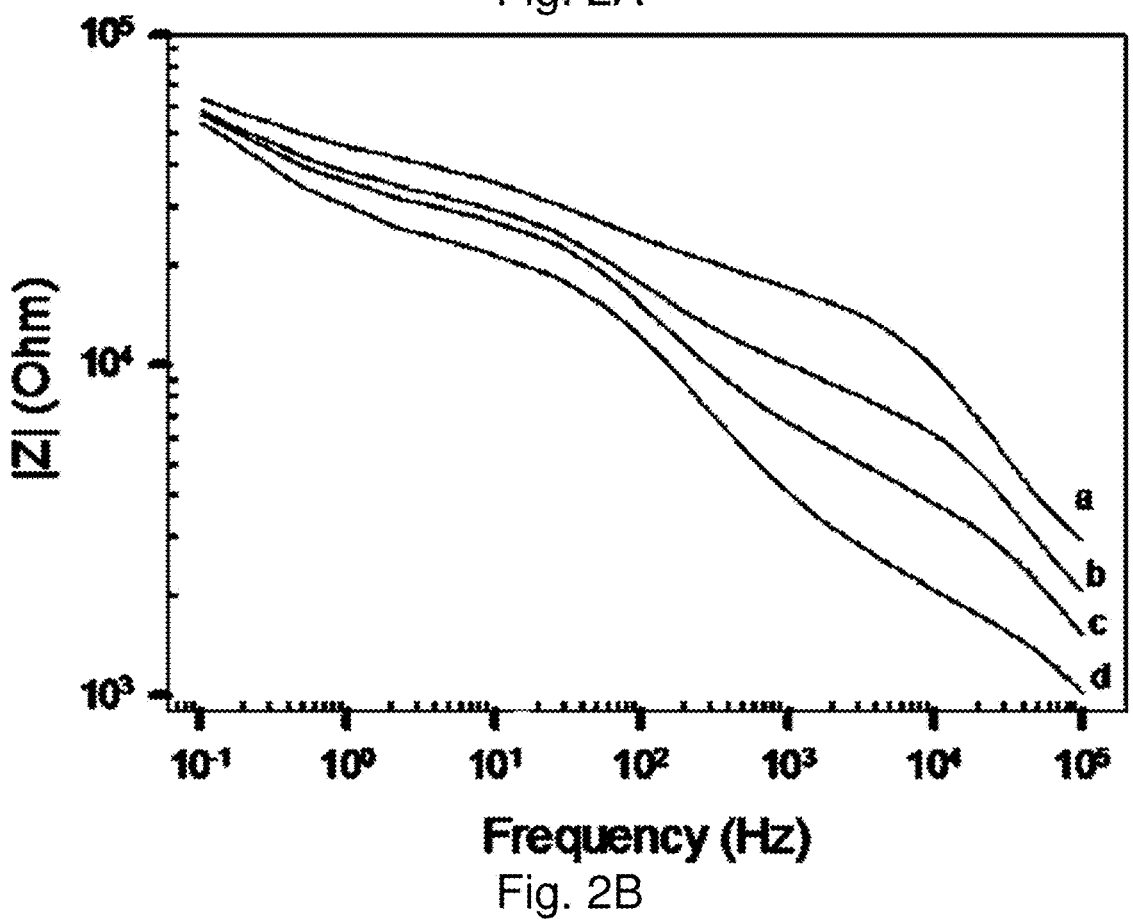
FIG. 2B shows a Bode impedance plot of MUA-AuNPs/CN/PAN/PET NM placed on top of a Pt interdigitated IME device in solutions of Na+ with different concentration (5 (a), 20 (b), 40 (c), and 80 mM (d)).

FIG. 2A shows a Nyquist impedance plot, and FIG. 2B shows a Bode impedance plot of MUA-AuNPs/CN/PAN/PET NM placed on top of a Pt interdigitated IME device in solutions of Na+ with different concentration (5 (a), 20 (b), 40 (c), and 80 mM (d)). FIG. 2A shows a representative set of Nyquist impedance plots of solutions with different Na+ concentrations. Similar results have also been obtained from samples of K+ or Li+ solutions. The semicircle characteristic of the charge transfer region and the slope characteristic of the mass transfer region show clear variations with the concentration of ions. In FIG. 2B, the data are plotted in Bode impedance, which clearly reveals that absolute impedance |Z| depends on the Na+ concentration.

By extracting the impedance values (|Z|) from FIG. 2B in the high frequency region, |Z| is shown to be dependent on the concentration of the ions, especially in the low concentration range.

Figure 3A:
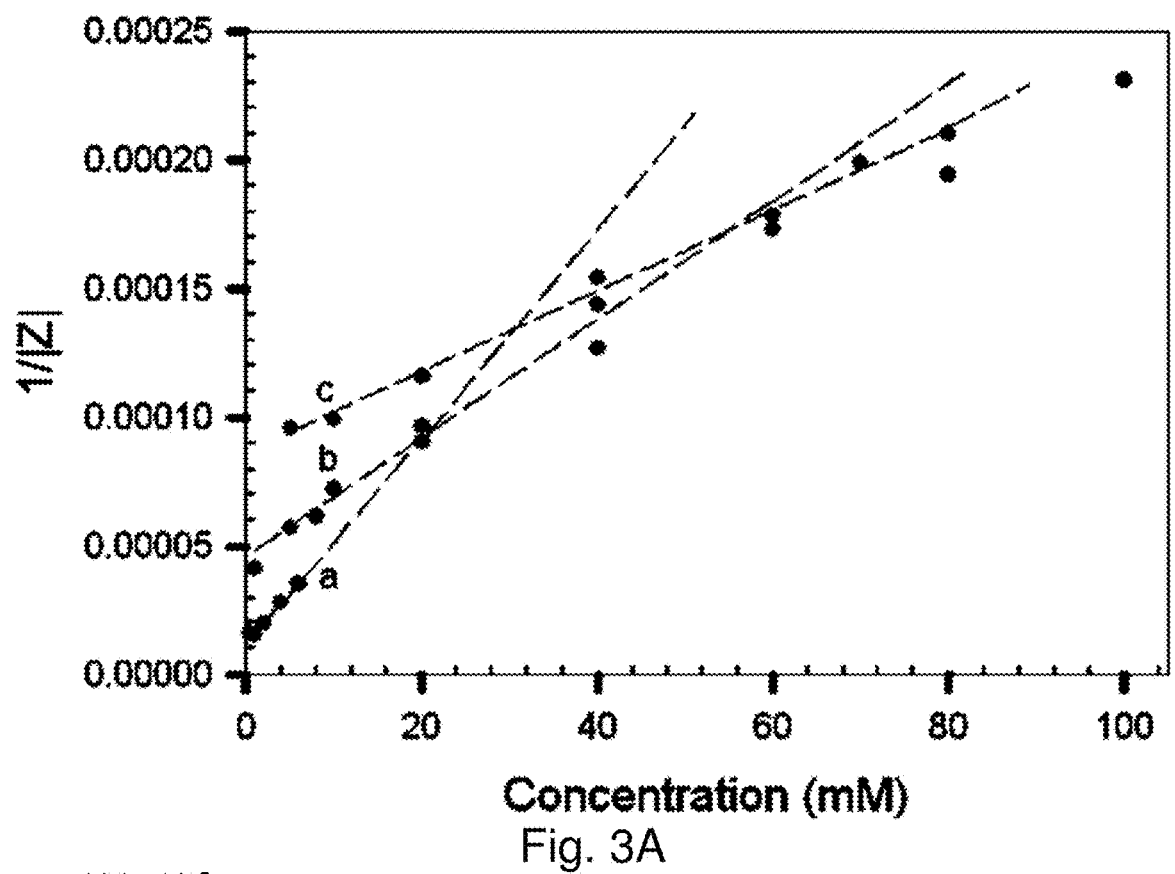
FIGS. 3A and 3B show plots of impedance and resistance values from Bode impedance and Nyquist impedance plots.
Figure 3B:
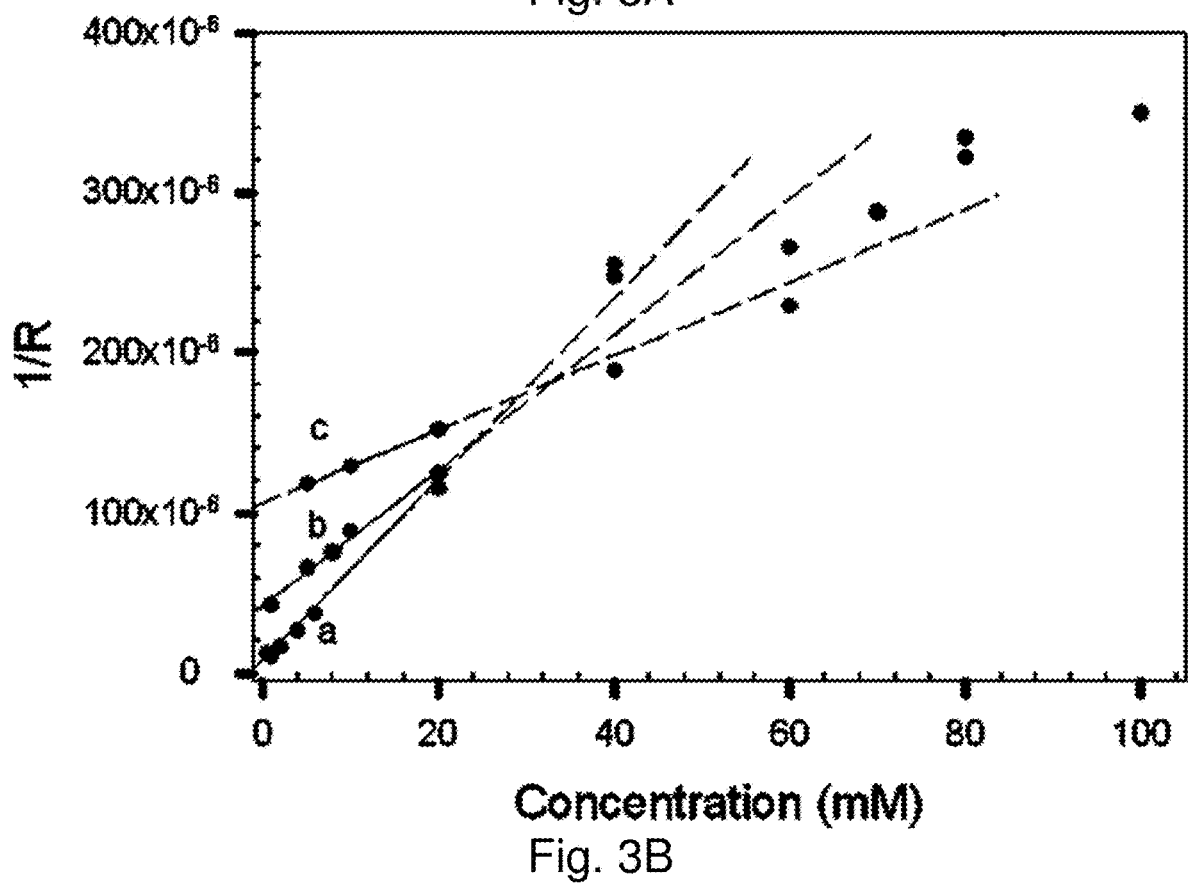

FIGS. 3A and 3B show plots of impedance and resistance values from Bode impedance and Nyquist impedance plots: FIG. 3A shows 1/|Z| vs concentration curves obtained from Bode impedance plots at 1 kHz; FIG. 3B shows 1/R values obtained by semicircle fit to Nyquist impedance plots with MUA-AuNPs/CN/PAN/PET NM on Pt-IME in solutions of K+ (a), Na+ (b), and Li+ (c) as a function of concentration. A representative set of 1/|Z| vs concentration curves is shown in FIG. 3A. In the low concentration range (<20-60 mM), the linear regression slopes of the 1/|Z| vs concentration curves display the order of K+ ($3.9 \times 10^{-6}$)>Na+ ($2.3 \times 10^{-6}$)>Li+ ($1.6 \times 10^{-6}$). The |Z| value becomes smaller when ion concentration increases. In other words, the conductivity increases as the ion concentration increases, and a plateau appears at >60 mM. The slopes are steep when the concentration is <20-60 mM. The nanocomposite membrane appears to be more sensitive to the ions in the lower concentration region. Similar trends are also observed by extracting the charge transfer resistance values from the semicircle fit of Nyquist impedance plots in the high frequency region, as shown in FIG. 3B. The magnitudes for the slopes of 1/R vs concentration curves display the order of K+ ($5.6 \times 10^{-6}$)>Na+ ($4.2 \times 10^{-6}$)>Li+ ($2.3 \times 10^{-6}$), quite similar to those obtained from the data from the Bode impedance plots (FIG. 3A).

These results indicate that the nanocomposite membrane functions as an ion sensitive and selective interfacial scaffold on the interdigitated microelectrode, which is consistent with the cation exchange membrane character of the MUA-Au NP films embedded in the nanofibrous membrane. In a typical cation-exchange membrane as stationary phase in chromatographic column, the relative affinities of different counterions in the mobile phase depend on the ionic charge, polarizability, and size of the solvated ion, and the type and interaction of the functional groups on the stationary phase. An increase of the charge-density (charge/solvated size) of the ion, or higher charge with smaller solvated ion radius, leads to higher electrostatic interactions with the stationary charges in the membrane (carboxylates), typically K+>Na+>Li+. In that case, the ionic conductance of the nanocomposite membranes (1/|Z|) would display the order K+<Na+<Li+, which is consistent with the experimental observation (FIG. 3A).

The same M-Au NPs/CN/PAN/PET scaffold is configured in between a pair of graphite printed electrodes on CN or PET sides of the membrane (FIG. 10B). For example, the impedance responses were measured in the test manifold in which G-PE is on the PET side of the membrane (FIG. 10C).

Figure 15A:
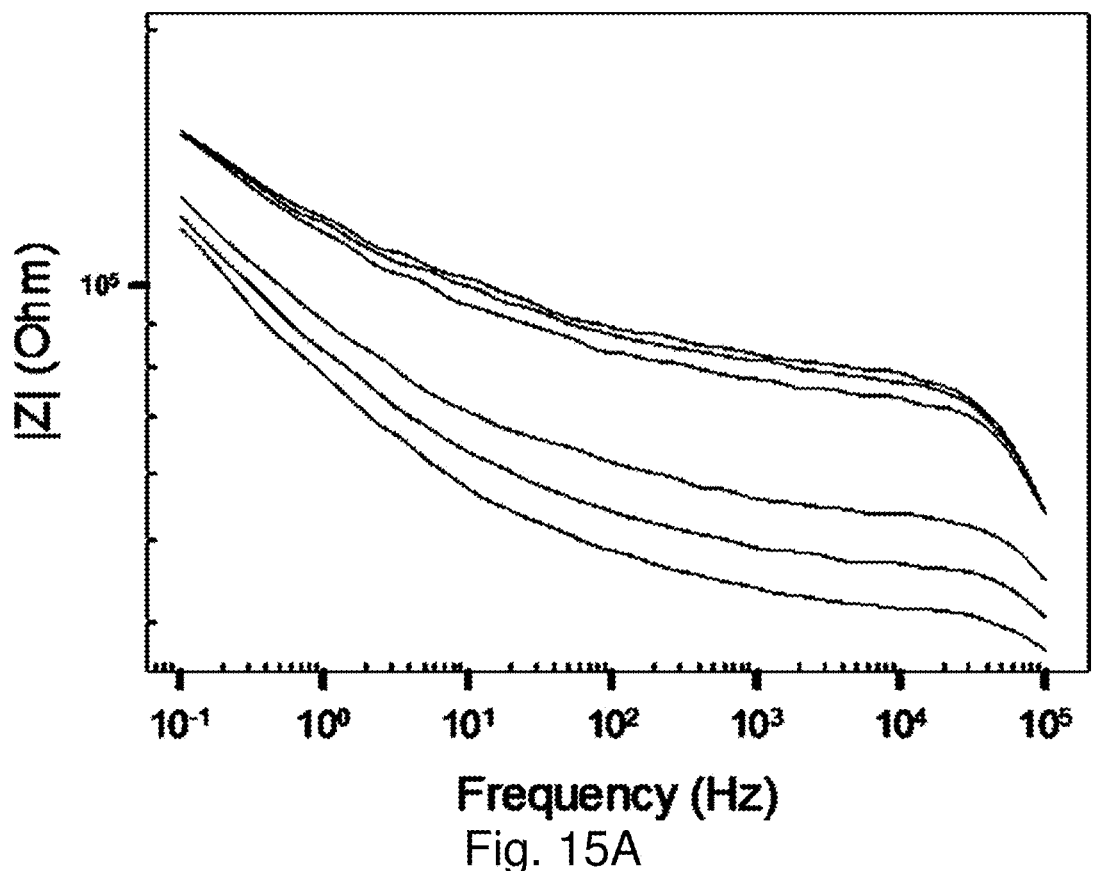
FIG. 15A shows a Bode impedance plots for MUA-AuNPs/CN/PAN/PET with G-PE on the PET side in solution of Na+ with different concentrations (top to bottom: 5, 10, 20, 60, 70, and 100 mM).
Figure 15B:
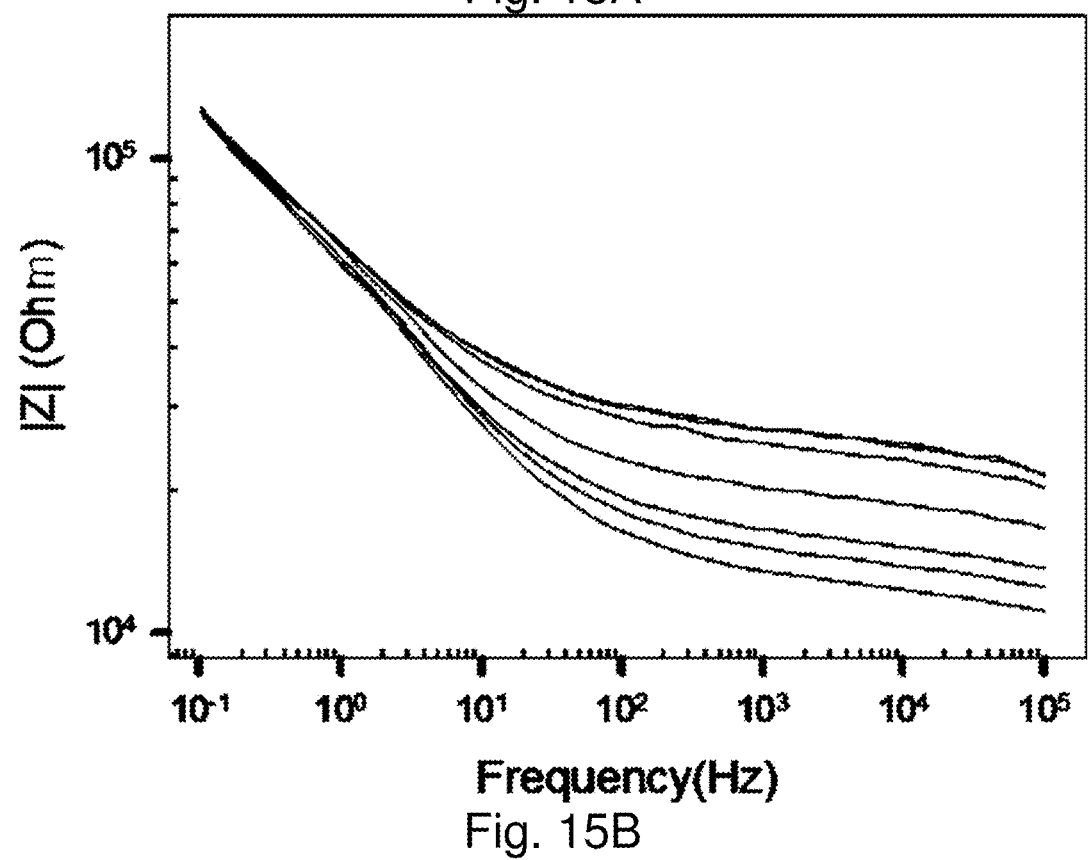
FIG. 15B shows a Bode impedance plots for MUA-AuNPs/CN/PAN/PET with G-PE on the CN side in solutions of Na+ with different concentrations.
Figure 15C:
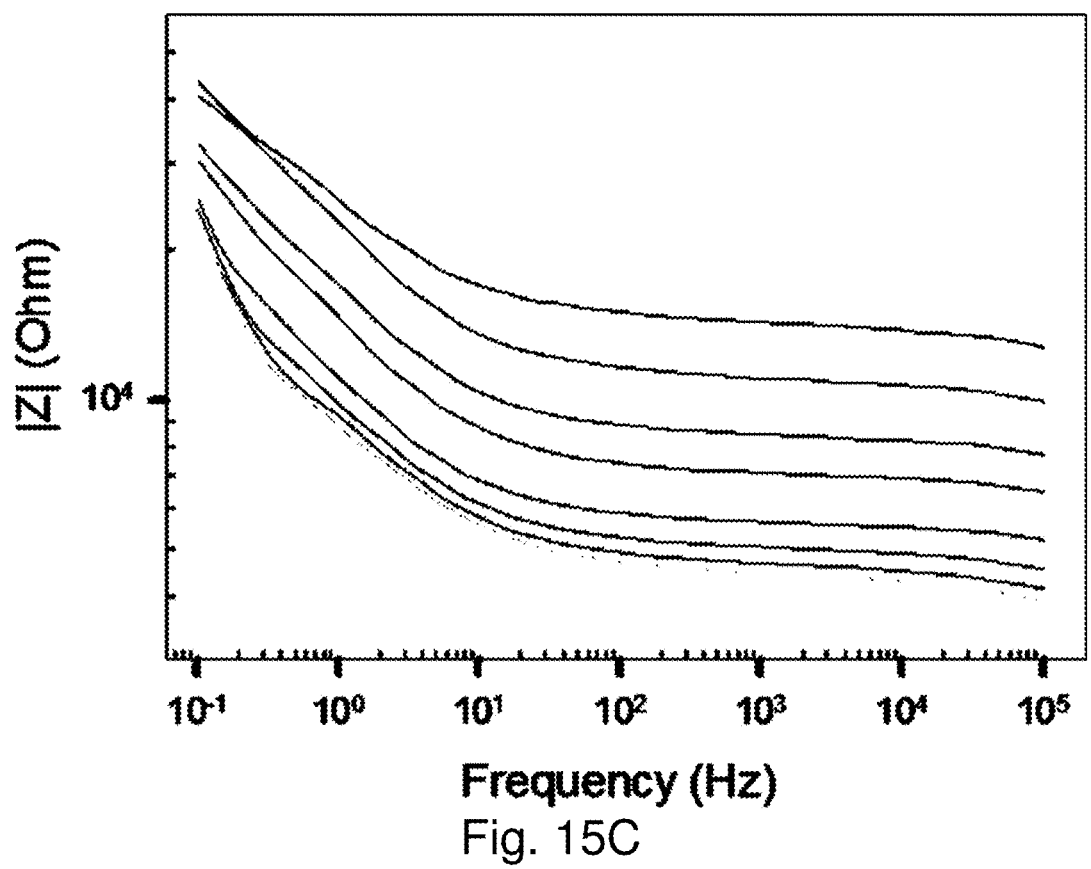
FIG. 15C shows a Bode impedance plots for PDA-AuNPs (42 nm)/CN/PAN/PET with G-PE in solutions of Na+ with different concentrations (top to bottom: 1, 5, 10, 20, 40, 60, 70, and 100 mM).

FIG. 15A shows a Bode impedance plots for MUA-AuNPs/CN/PAN/PET with G-PE on the PET side in solution of Na+ with different concentrations (top to bottom: 5, 10, 20, 60, 70, and 100 mM). FIG. 15B shows a Bode impedance plots for MUA-AuNPs/CN/PAN/PET with G-PE on the CN side in solutions of Na+ with different concentrations. FIG. 15C shows a Bode impedance plots for PDA-AuNPs (42 nm)/CN/PAN/PET with G-PE in solutions of Na+ with different concentrations (top to bottom: 1, 5, 10, 20, 40, 60, 70, and 100 mM). As shown in Bode impedance plots for samples containing Na+ (FIG. 15A), |Z| value starts to differentiate with various concentrations even in the lower frequency region, and the difference becomes greater in the higher frequency region.

Figure 4A:
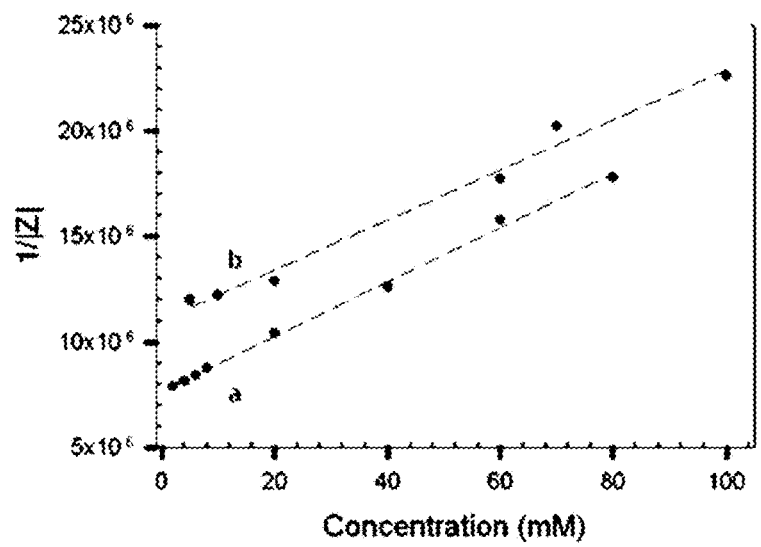
FIGS. 4A and 4B show plots of $1/|Z|$ values obtained from Bode impedance plots at 1 kHz for MUA-AuNPs/CN/PAN/PET, in solutions as a function of K+ (a) and Na+ (b) concentration.
Figure 4B:
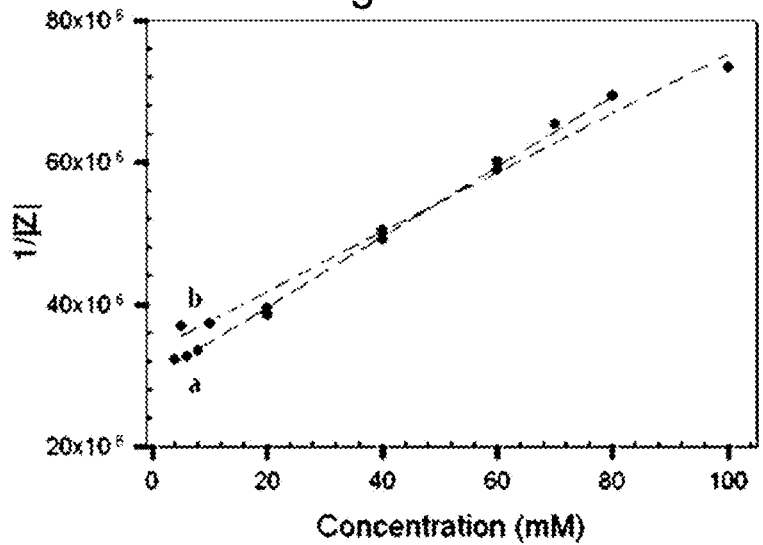
Figure 4C:
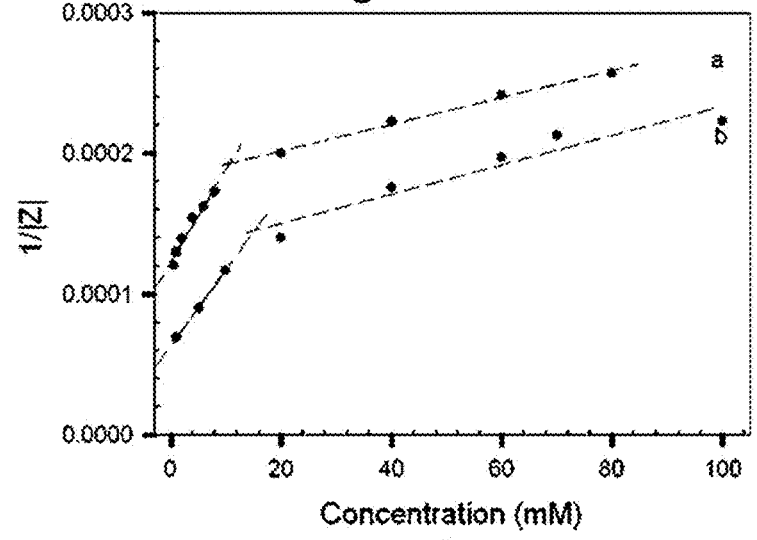
FIG. 4C shows plots of $1/|Z|$ values obtained from Bode impedance plots at 1 kHz for PDA-Au NPs (42 nm)/CN/PAN/PET with G-PE in solutions of K+ (a) and Na+ (b) as a function of salt concentration.

FIGS. 4A and 4B show plots of 1/|Z| values obtained from Bode impedance plots at 1 kHz for MUA-AuNPs/CN/PAN/PET with G-PE on the PET side (FIG. 4A) and the CN side (FIG. 4B) in solutions as a function of K+ (a) and Na+ (b) concentration. FIG. 4C shows plots of 1/|Z| values obtained from Bode impedance plots at 1 kHz for PDA-Au NPs (42 nm)/CN/PAN/PET with G-PE in solutions of K+ (a) and Na+ (b) as a function of salt concentration. FIG. 4A shows plots of 1/|Z| values extracted from Bode impedance at 1 kHz vs ionic concentration. In the high frequency region, 1/|Z| shows a clear dependence of the ion concentration, similar to the results from NM-Pt-IME device (FIG. 3B) except subtle differences in the slope values. The magnitudes for the slopes of 1/|Z| vs concentration curves display the order of K+ ($1.3 \times 10^{-7}$)>Na+ ($1.2 \times 10^{-7}$) in the entire concentration range. A similar trend is also observed by extracting the resistance values from the semicircle fit of Nyquist impedance plots.

For the case of G-PE on the CN side in solutions containing Na+ with different concentrations, the |Z| vs frequency curves (FIG. 15B) in the low frequency region appear to be independent of the concentration of ions. At >10 kHz, the impedance shows changes in the |Z| vs frequency curves, exhibiting a clear dependence of the ion concentration. A similar Bode impedance plot is also observed for samples containing K+. By extracting the impedance values (|Z|) from the Bode impedance plots at three frequencies in the high frequency region, |Z| is shown to be linearly dependent on the ion concentrations (FIG. 4B). The slopes of the 1/|Z| vs concentration curves are quite comparable (K+ ($5.0 \times 10^{-7}$) Na+ ($4.2 \times 10^{-7}$)), showing much smaller differences in comparison with the data shown in FIGS. 4A and 4B. A similar trend is also observed by extracting the resistance values from the semicircle fit of Nyquist impedance plots.

The P-NPs/NM scaffolds were also examined. For example, with PDA-Au NPs (42 nm)/CN/PAN/PET being configured in between a printed pair of graphite electrodes on CN or PET sides of the membrane (see FIG. 10B), the Bode impedance plots of solutions containing different concentrations of Na+ show clear changes (FIG. 15C). For the data at frequency greater than 10 Hz, Bode impedance curves display a clear dependence on the ion concentration. By extracting the impedance values ($|Z|$) at 1 kHz, a comparison between Na+ and K+ shows that the overall $1/|Z|$ values of K+ are greater than those of Na+ (FIG. 4C). This finding is opposite to the results observed from Au-MUA NPs (see FIGS. 3A and 3B), suggesting the operation of a different mechanism in the thin film. In the acrylate-capped Au NPs (42 nm)/CN/PAN/PET membrane, the acrylate-capped Au NPs feature multiple negative charges on the nanoparticle surface. Upon incorporating the positively charged polymer (diallyl ammonium groups), there must be excess negative charges on the NPs which are balanced by the mobile cations in the solution, forming an electrical double layer around the nanoparticles. In this case, it is the ionic mobility that determines the ionic conductance of the membrane. Since K+ ions exhibit a higher ionic mobility than Na+ ions, the overall $1/|Z|$ values of K+ are greater than those of Na+ in the MUA-Au NPs (7 nm)/CN/PAN/PET membrane. It is important to note that the slopes of the $1/|Z|$ vs concentration curves are quite comparable between K+ and Na+ (e.g., K+ ($6.50 \times 10^{-6}$) Na+ ($5.35 \times 10^{-6}$) for <20 mM). Unlike MUA-AuNPs film, the selectivity of the PDA-Au NPs film is apparently very limited.

Detection of Sweat.

On the basis of the above data for the detection of salts in solutions, the viability of the MUA-AuNPs/CN/PAN/PET with G-PE on the PET side was further examined with normal volunteers before and after exercises. While sweat contains different chemical constituents with different concentrations, as stated earlier, the study described in this subsection focused on the salt and moisture detections to demonstrate the sensing properties of the as-prepared nanoparticle-nanofibrous nanocomposites.

The detection of biological species (e.g., glucose, urea, or lactate) is possible by use of enzymatic or nonenzymatic modifications of the nanocomposite.

Figure 5A:
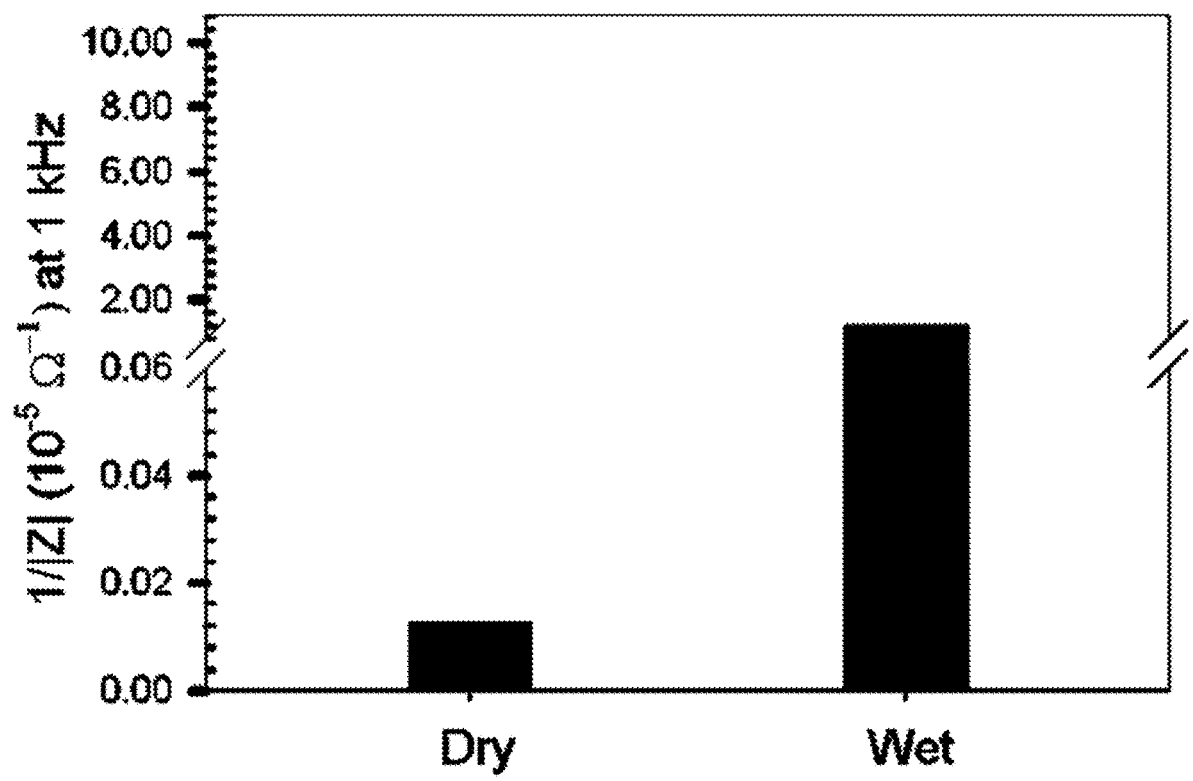
FIGS. 5A and 5B show $1/|Z|$ values extracted from Bode impedance plots for MUA-AuNPs/CN/PAN/PET with G-PE.
Figure 5B:
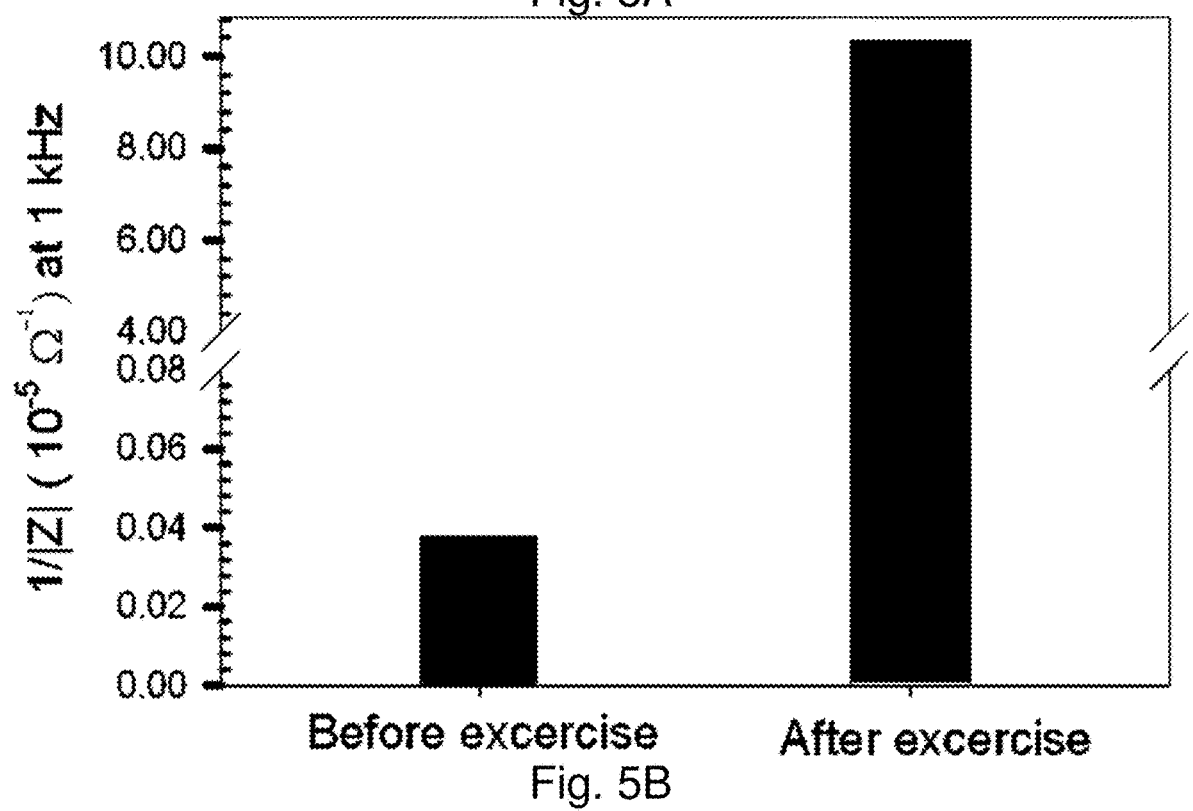

FIGS. 5A and 5B show $1/|Z|$ values extracted from Bode impedance plots for MUA-AuNPs/CN/PAN/PET with G-PE in response to water (as a control, FIG. 5A) and sweat (perspiration test, FIG. 5B). FIGS. 5A and 5B show a representative set of data with the measurement configuration illustrated in FIG. 10D. Data were collected by placing a thin nonwoven scaffold on the sensor surface (CN side) and lightly pressing it against the wrist (see FIG. 10D) before and after 5 min exercise (running stairs). The control experiment was performed by directly placing a drop of water on the dry nanocomposite in between the two electrodes, followed by impedance measurement of the wet membrane.

Figure 19:
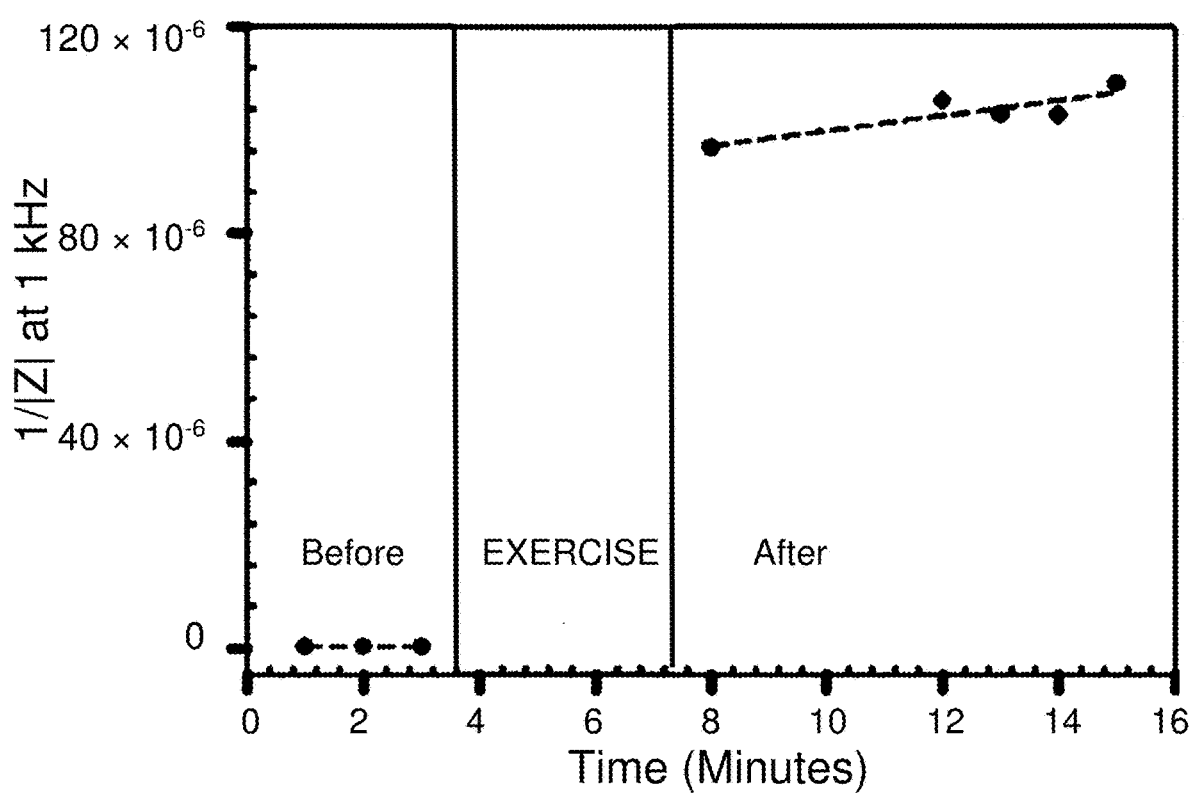
FIG. 19 shows plots showing the real time monitoring of sweat before and after exercise (5 minutes exercise).

FIG. 19 shows plots showing the real time monitoring of sweat before and after exercise (5 minutes exercise) or in real time. A control experiment was also performed by measuring the impedance before and after placing a small drop of pure water onto the sensor surface. In the control experiment, the results clearly show a sharp drop of impedance (or increase of conductance) from dry to wet membrane (FIG. 5A). In comparison, the difference between "before exercise" and "after exercise" is much greater than that observed from the control experiment (FIG. 5B). This is mainly attributed to the presence of salts in the sweat, which is substantiated by rinsing the membrane with water several times after which the impedance values were almost the same as that before subjecting to sweat test.

It is evident that the relative change for the individual before and after exercise (96%) is smaller than that for the control experiment using pure water (99%). This is expected because salts in the sweat greatly increase the conductivity in comparison with pure water.

Detection of Relative Humidity Changes in Air and from Perspiration.

Detection of Relative Humidity Changes in Air.

With devices of Au70 nm/CN/PAN/PET (with G-PE on CN side), the response characteristics between PDA-Au NPs (70 nm) and MUA-Au NPs (7 nm) in NM were first compared. The impedance data at different RH % were collected by flowing air or $N_2$ from a water bubbler with a flow controller, at each flow rate the RH % were recorded by a commercial humidity meter.

Figure 6A:
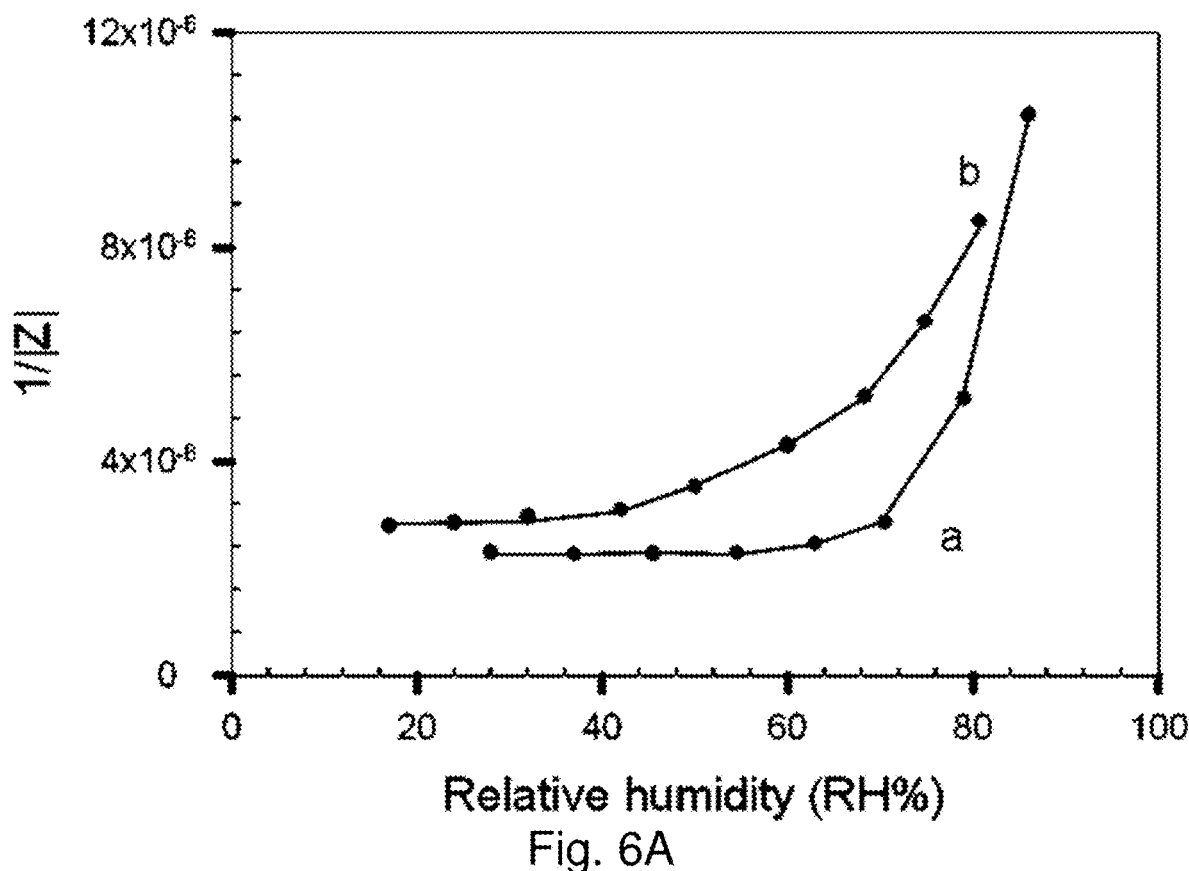
FIGS. 6A and 6B show a comparison of $1/|Z|$ (FIG. 6A) and $\Delta|Z|/|Zi|$ (FIG. 6B) vs RH % curves (extracted from Bode impedance plots at 20 kHz) as a function of relative humidity for two different sensing scaffolds: MUA-Au NPs (7 nm) NM (slope in linear region: $-3.2\times10^{-2}$ (a)) and PDA-Au NPs (70 nm) NM (slope in linear region: $-1.5\times10^{-2}$ (b)).
Figure 6B:
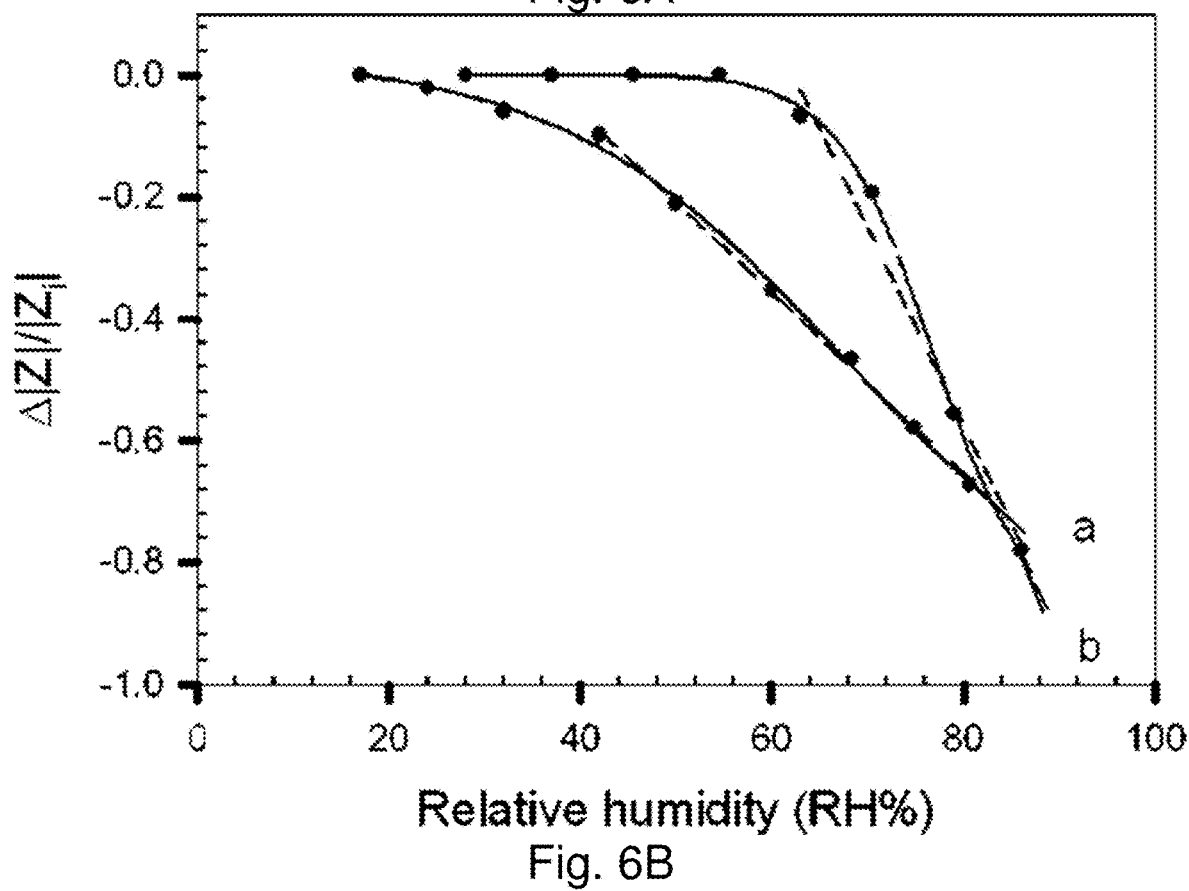

FIGS. 6A and 6B show a comparison of $1/|Z|$ (FIG. 6A) and $\Delta|Z|/|Z_i|$ (FIG. 6B) vs RH % curves (extracted from Bode impedance plots at 20 kHz) as a function of relative humidity for two different sensing scaffolds: MUA-Au NPs (7 nm) NM (slope in linear region: $-3.2 \times 10^{-2}$ (a)) and PDA-Au NPs (70 nm) NM (slope in linear region: $-1.5 \times 10^{-2}$ (b)).

Data were first obtained with a sensor device of MUA-Au NPs/CN/PAN/PET on G-PE in which the G-PE is on CN side. On the basis of impedance data extracted from Bode impedance plots, both $1/|Z|$ (FIG. 6A) and $\Delta|Z|/|Z_i|(=(|Z|-|Z_i|)/|Z_i|$ where $Z_i$ is the initial impedance) (FIG. 6B) are plotted against RH %, in which the $\Delta|Z|/|Z_i|$ RH % plots seem to provide a better comparison of the responses. When RH %>50%, the results display a significant response. When RH %<50%, the response is independent of RH %. The results are likely reflecting the low hydrophilicity of the nanocomposite membrane, which is responsible for the insignificant response sensitivity in the low RH % range.

To manipulate the hydrophilicity, a highly hydrophilic polymer, PDA, was used for the assembly of Au NPs in the nanocomposite membrane. The membranes were fabricated by PDA mediated assembly of acrylate-capped Au NPs of different sizes (70 or 42 nm) in the nanofibrous membranes. Different concentration ratios of PDA vs Au NPs were studied for the assemblies. As shown in FIG. 6B for PDA-Au NPs (70 nm)/CN/PAN/PET NM on G-PE, it is evident that the response to a wider RH % range. Note that the slope in the low RH % range (<50%) is slightly smaller than that in the high RH % range. In comparison with MUA-Au NPs/CN/PAN/PET on G-PE, in the high RH % range (>50%), the sensitivity of PDA-Au NPs (70 nm)/CN/PAN/PET NM on G-PE is relatively smaller, indicating the importance of balancing hydrophobicity and hydrophilicity in the nanocomposite. Note that the sensitivity also depends on the gap between electrodes. A smaller gap shows a great sensitivity, which is evidenced by the impedance changes as a function of relative humidity for PDA-Au NPs (70 nm)/CN/PAN/PET NM with G-PE with different G-electrode gaps. The sensitivity may be optimized by adjusting the electrode gap.

To understand the composition effect of the nanocomposite on response characteristics, the nanocomposite membranes were examined with different ratios of Au NPs vs PDA, as well as different particle sizes using IME as the detection platform. With PDA-Au NPs (70 nm)/CN/PAN/

PET on Pt-IME (FIG. 10A) placed in the test manifold (FIG. 10C), a series of impedance values (|Z|) extracted from the Bode impedance plots at 20 kHz (not shown) as a function of the relative humidity are compared with sensors of PDA-Au NPs/CN/PAN/PET on Pt-IME with subtle differences in PDA and Au NPs.

Figure 7A:
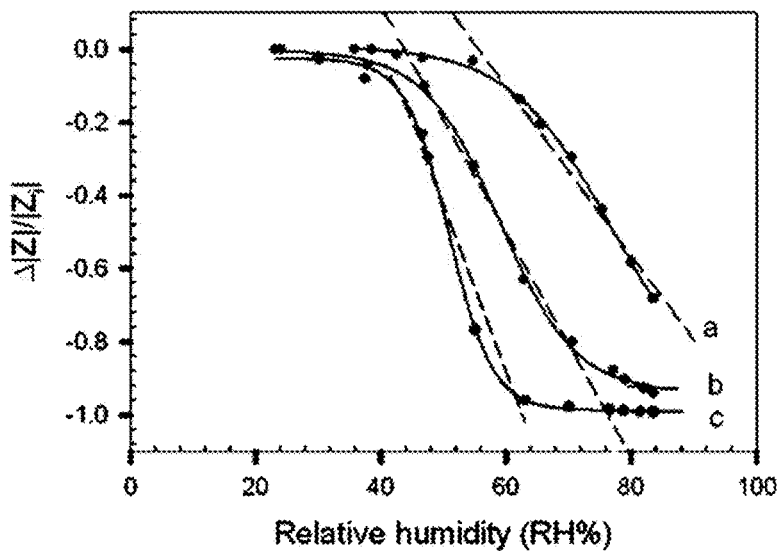
FIGS. 7A, 7B and 7C show plots of $\Delta|Z|/|Zi|$ vs RH % for PDA-AuNPs/CN/PAN/PET NM on Pt-IME.
Figure 7B:
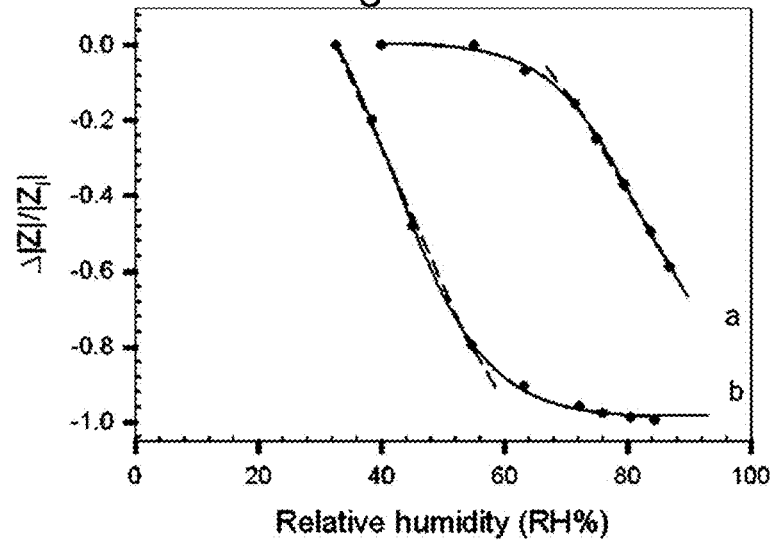
Figure 7C:
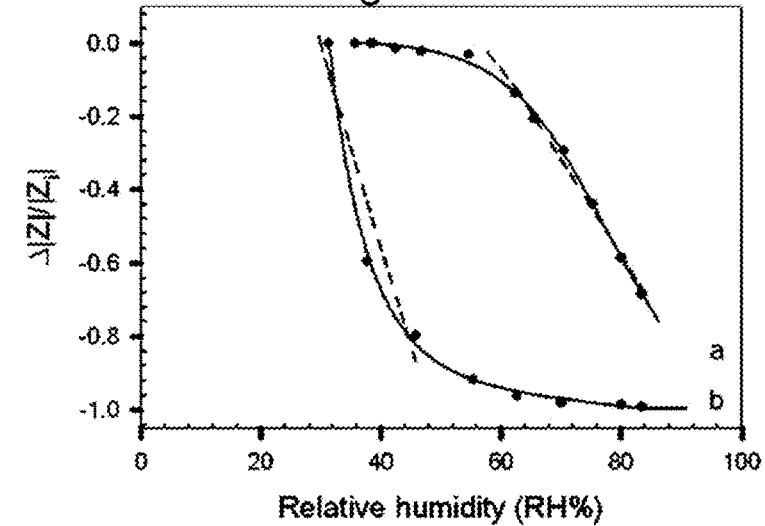

FIGS. 7A, 7B and 7C show plots of $\Delta|Z|/|Z_i|$ vs RH % for PDA-AuNPs/CN/PAN/PET NM on Pt-IME. FIG. 7A shows data for scaffolds derived from PDA of constant concentration and Au NPs (70 nm) of different concentrations (5.0× 1010 (a), 2.0×1011 (b), and 1.0×1011 NPs/mL (c), Slopes: $-2.3\times10^{-2}$ (a); $-2.0\times10^{-2}$ (b); and $-4.5\times10^{-2}$ (c)). FIG. 7B shows data for scaffolds derived from PDA with different concentrations (0.4 M (a) and 0.76 M (b)) and the same concentration of Au NPs (70 nm, $5.0\times10^{10}$ NPs/mL, Slopes: $-2.8\times10^{-2}$ (a); and $-3.1\times10^{-2}$ (b)). FIG. 7C shows data for scaffolds derived from PDA of the same concentration (0.4 M) and Au NPs of two different sizes (70 nm (a) and 42 nm (b)). (Slopes: $-2.6\times10^{-2}$ (a) and $-3.6\times10^{-2}$ (b).)

FIG. 7A shows a set of $\Delta Z/Z_i$ data (also see FIG. 16A) as a function of the relative humidity for PDA-Au NPs/CN/PAN/PET prepared by mixing PDA with a constant concentration and Au NPs (70 nm) with different concentrations. It is evident that both the sensitivity and the sensitive range increase with an increase ratio of Au NPs to PDA in the NM. FIG. 7B shows a set of $\Delta Z/Z_i$ data (also see FIG. 16B) as a function of relative humidity for PDA-Au NPs/CN/PAN/PET prepared by mixing Au NPs with a constant concentration and PDA of different concentrations. The sensitivity in the low RH % range increases with PDA concentration in the NM. However, in the high RH % range the sensitivity increases with a decrease of PDA concentration in the NM. This behavior is consistent with the highly hydrophilic nature of PDA.

Figure 16A:
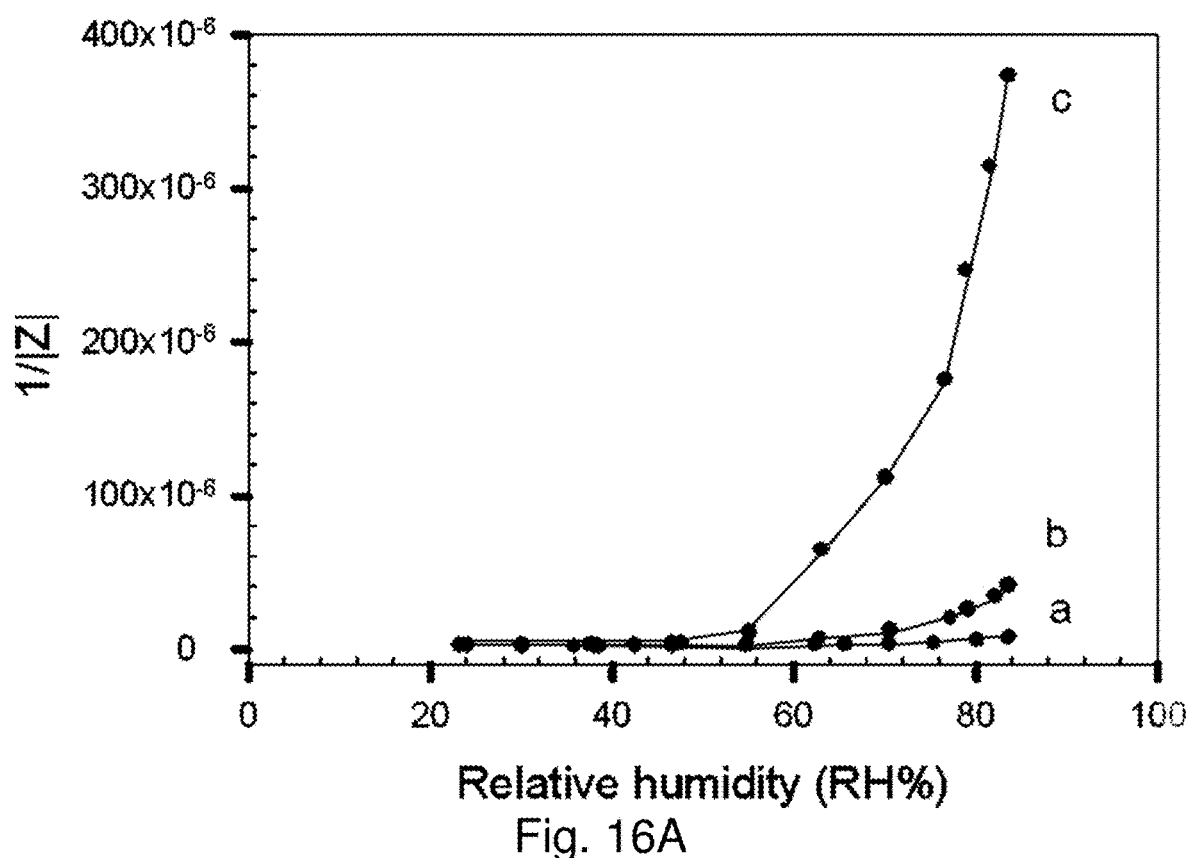
FIGS. 16A-16C show plots of $1/|Z|$ vs RH % (extracted from Bode impedance plots at 20 kHz) for PDA-Au NPs/CN/PAN/PET NM on Pt-IME as a function of relative humidity.
Figure 16B:
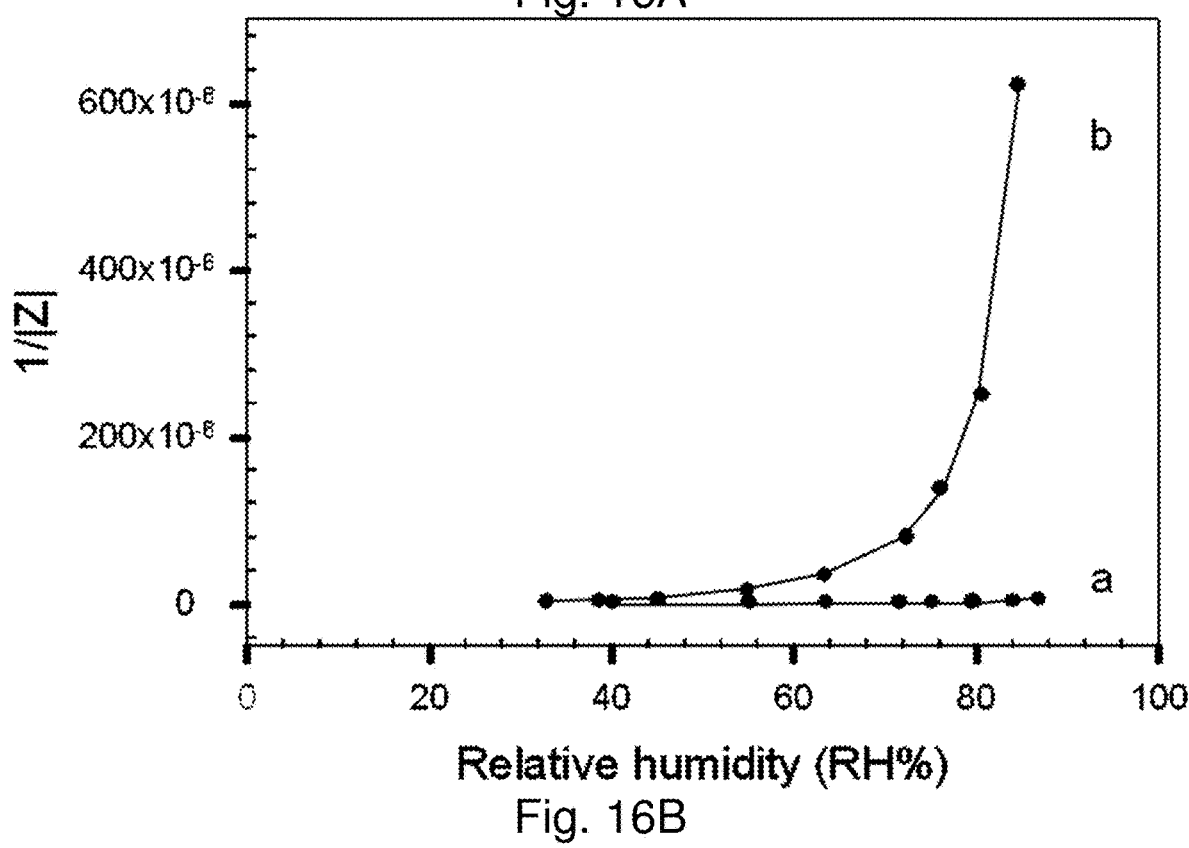
Figure 16C:
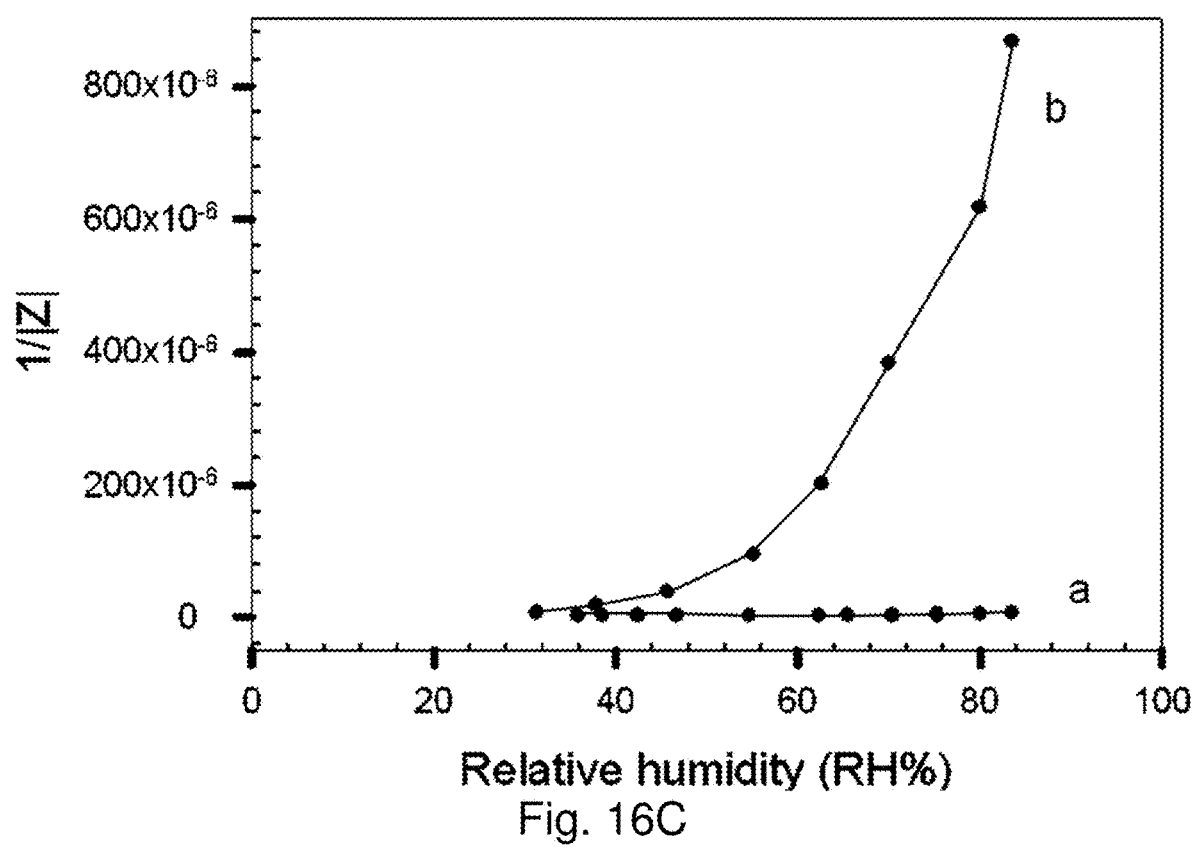
Figure 17A:
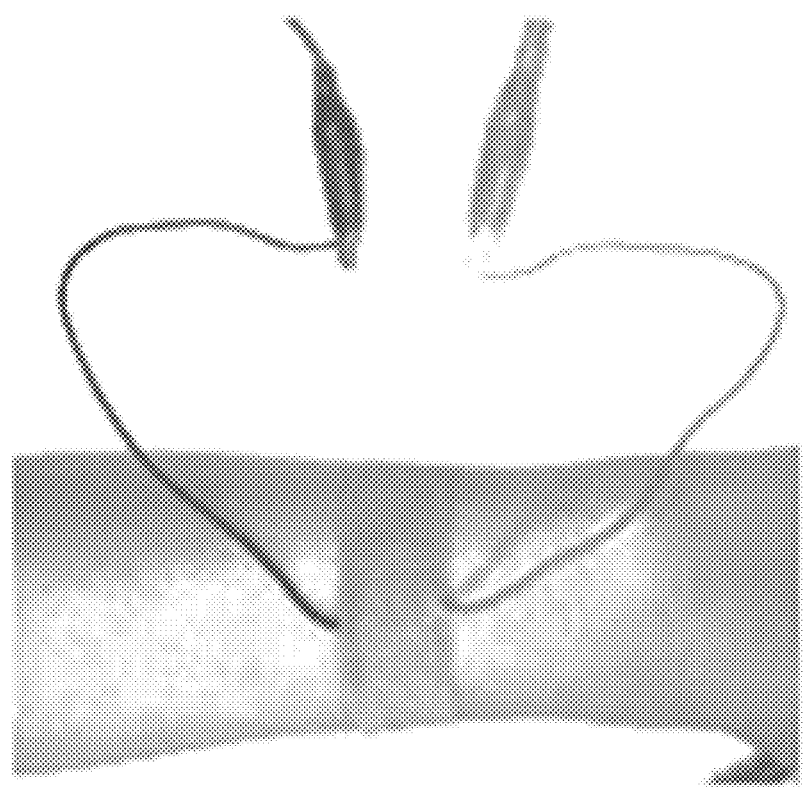
FIGS. 17A and 17B show photos showing the sensor setups for human secretion monitoring.
Figure 17B:
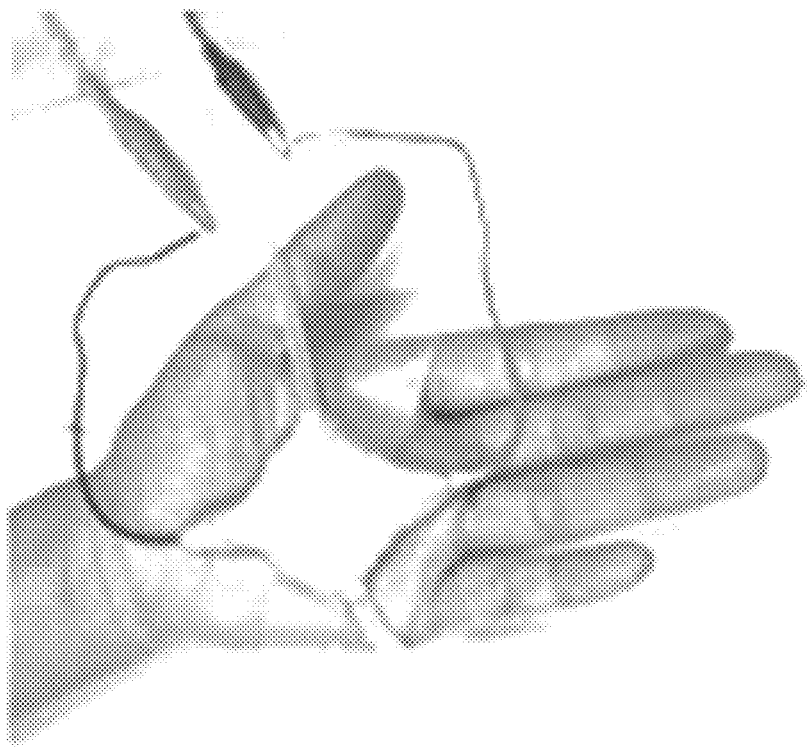
Figure 18A:
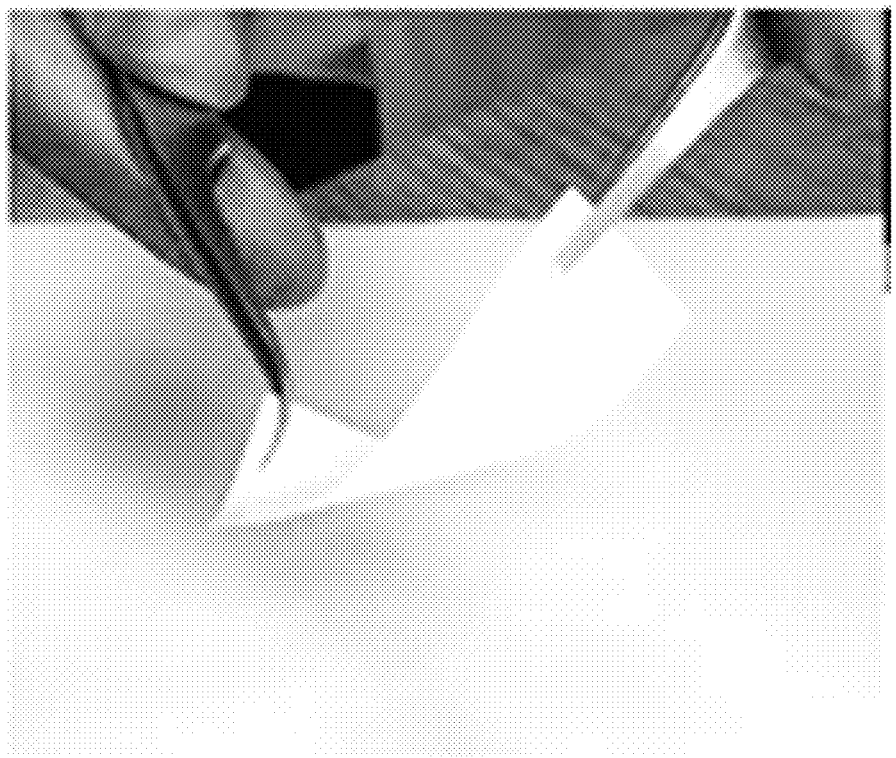
FIGS. 18A and 18B show photos showing the flexibility and bending characteristics for the nanofibrous membrane.
Figure 18B:
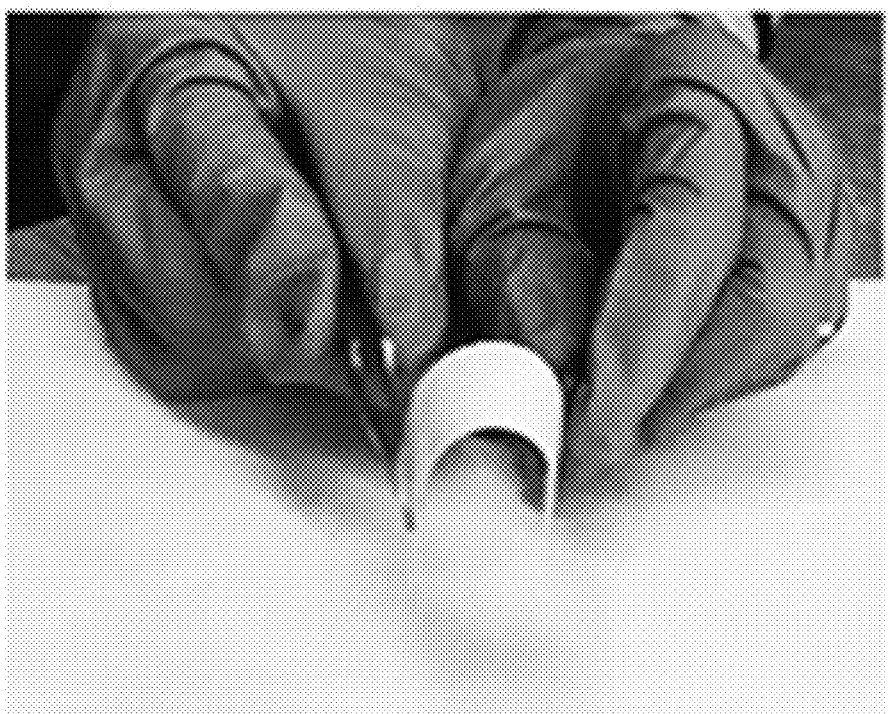

FIGS. 16A-16C show plots of 1/|Z| vs RH % (extracted from Bode impedance plots at 20 kHz) for PDA-Au NPs/CN/PAN/PET NM on Pt-IME as a function of relative humidity. FIG. 16A shows data for scaffolds derived from PDA of fixed concentration and Au NPs (70 nm) of different concentrations ($5.0\times10^{10}$ (a), $2.0\times10^{11}$ (b), and $1.6\times10^{11}$ NPs/mL (c)); FIG. 16B shows data for scaffolds derived from PDA of different concentrations (0.4 M (a) and 0.76 M (b)) and the same concentration of Au NPs (70 nm, 5.0×1010 NPs/mL); FIG. 16C shows data for scaffolds derived from PDA of the same concentration (0.4 M) and Au NPs of two different sizes (70 nm (a) 42 nm Au NPs (b)).

The particle size effect on the response sensitivity was also examined. FIG. 7C shows a set of $\Delta Z/Z_i$ data as a function of relative humidity for PDA-Au NPs/CN/PAN/PET NM/G-PE with Au NPs of two different sizes. It is evident that the NM with small size Au NPs seems to exhibit overall smaller 1/|Z| value in comparison with the large size NPs (see FIG. 16C). The sensitivity clearly depends on the particle size in different RH % ranges. The smaller-sized particles show a higher sensitivity in the low RH % region, whereas the larger-sized particles exhibit a higher sensitivity in the high RH % region.

Detection of Perspiration.

The viability of PDA-AuNPs/CN/PAN/PET devices (with G-PE) for detection of perspiration was examined with normal individual volunteers before and after exercises.

Figure 8A:
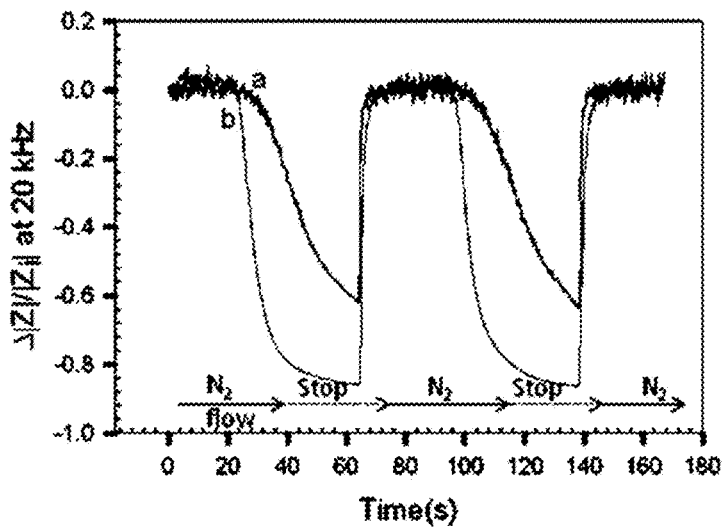
FIGS. 8A, 8B and 8C show sensor responses ($\Delta|Z|/|Zi|$) measured at –20 kHz for a device of PDA-AuNPs (70 nm)/CN/PAN/PET with G-PE for two volunteers (#1 (A) and #2 (B)) before and after exercise (running stairs for ~5 min), and a calibration curve for the sensor.
Figure 8B:
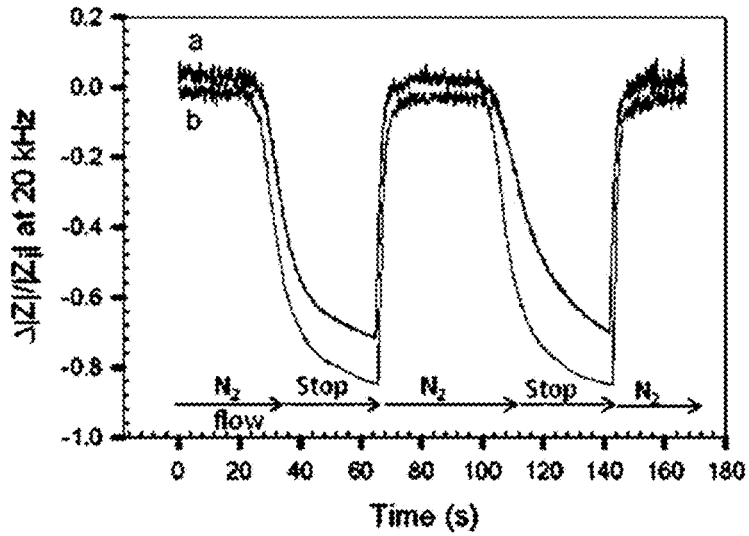
Figure 8C:
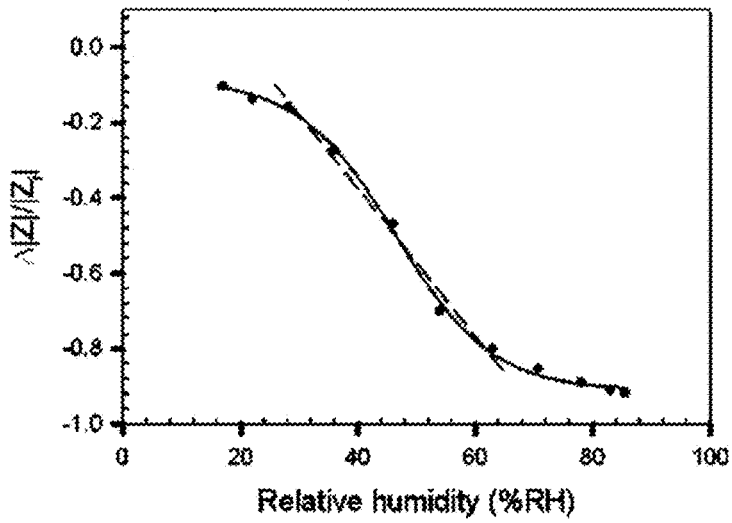

FIGS. 8A and 8B show sensor responses ($\Delta|Z|/|Z_i|$) measured at ~20 kHz for a device of PDA-AuNPs (70 nm)/CN/PAN/PET with G-PE for two volunteers (#1 (A) and #2 (B)) before (FIG. 8A) and after (FIG. 8B) exercise (running stairs for ~5 min). FIG. 8C shows a calibration curve for the same sensor device with controlled RH % in air (slope: $2.0\times10^{-2}$).

FIGS. 8A and 8B show a typical set of $\Delta Z/Z_i$ response (measured at ~20 kHz) of a device of PDA-AuNPs/CN/PAN/PET (with G-PE on CN side) with the measurement configuration illustrated in FIG. 10E. The measurement was performed by placing the sensor compartment on the palm and the perspiration was measured by stopped air flow method. Data were collected from palms of volunteers #1 and #2 before and after ~5 min exercise (running stairs). The measurement was performed by placing the sensor compartment on top of the palm and the perspiration was measured by stopped air flow method. During the initial 30 s, air flows into the device to establish a baseline. The perspiration of the volunteer's palm was monitored for 45 s upon stopping air flow. The baseline returns upon air flowing again. This procedure was repeated for one more time. The responses to exercises are significant and reversible, with the response magnitude being clearly dependent on the individual, as reflected by the difference between #1 and #2.

Based on the relative changes of $\Delta Z/Z_i$ values before and after the exercises, it is evident that the corresponding changes of RH % falls in between 50 and 72% (for #1) and 56-62% (for #2), as estimated from the calibration data shown in FIG. 8C.

Devices with G-PE on the PET side were also tested. For example, the response for PDA-AuNPs/CN/PAN/PET with G-PE on the PET side was found to be much smaller than that with G-PE on the CN side. This finding is indicative of the importance of the nanocomposite membrane-electrode configuration in the sensor response.

Figure 11A:
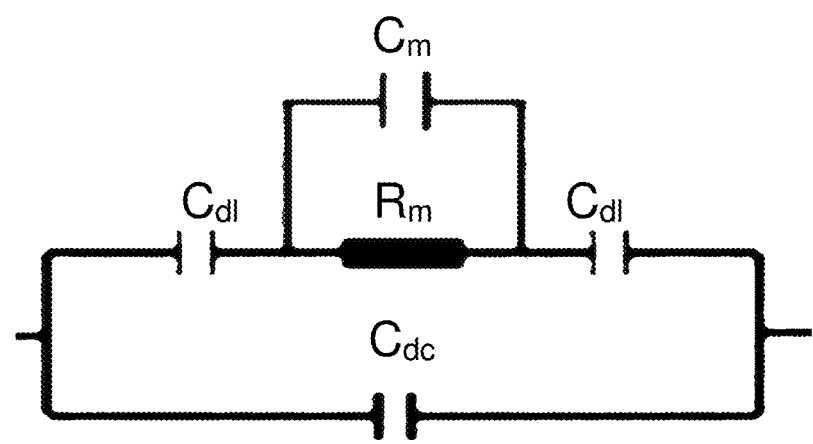
FIGS. 11A and 11B show illustrations of ideal model of an equivalent circuit for the chemiresistor-type device with the nanoparticle-nanofibrous nanocomposite membrane, having Cm in parallel with Rm, and Rs in series with Cdl, respectively.
Figure 11B:
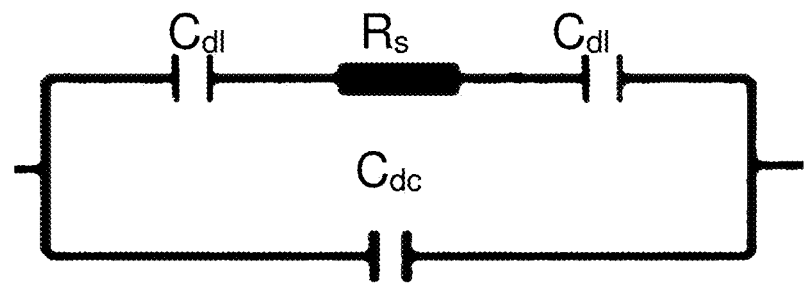

FIGS. 11A and 11B show illustrations of ideal model of an equivalent circuit for the chemiresistor-type device with the nanoparticle-nanofibrous nanocomposite membrane, having Cm in parallel with $R_m$, and $R_s$ in series with $C_{dl}$, respectively.

Figure 12:
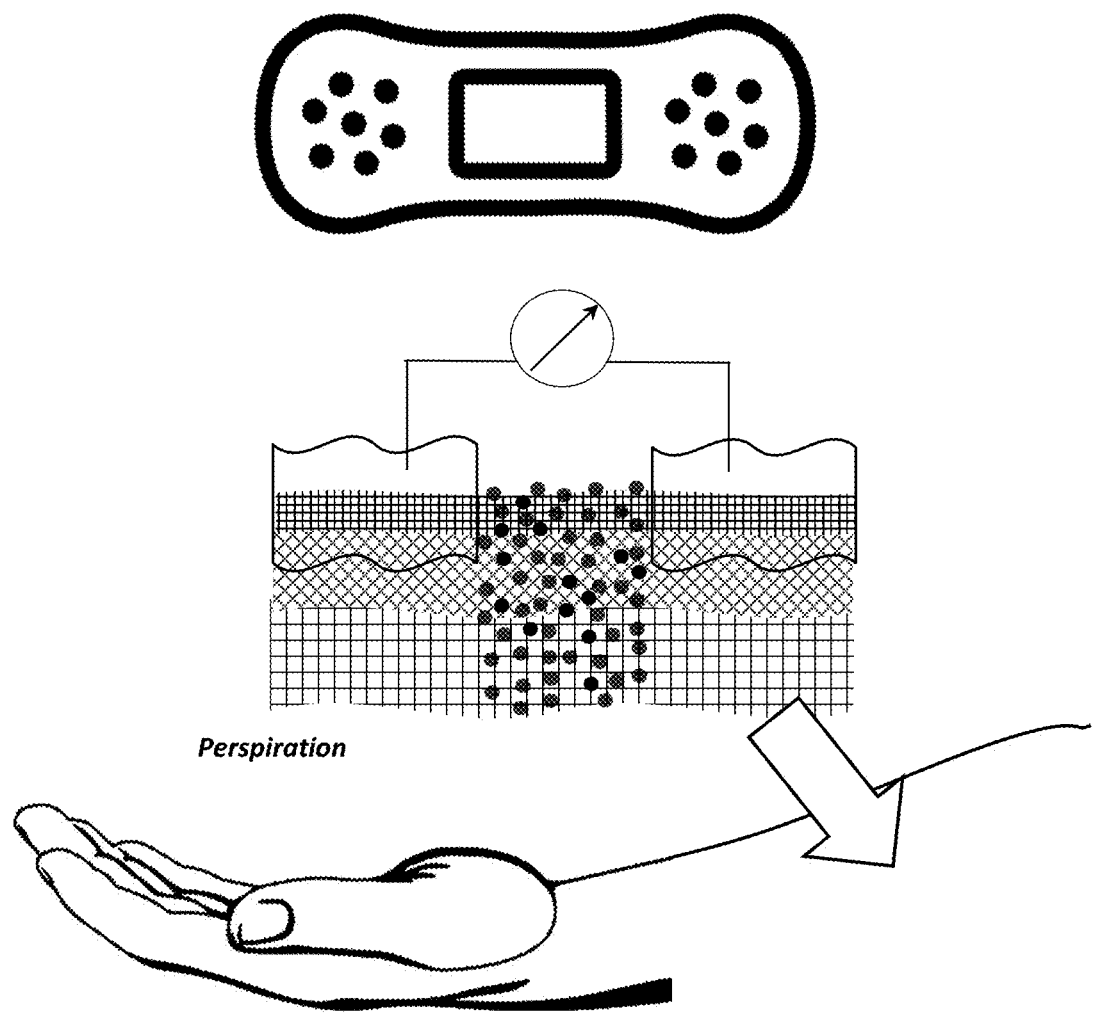
FIG. 12 shows a schematic representation of the sensor incorporated into a self-adhesive strip, which can be applied to the skin.

FIG. 12 shows a schematic representation of the sensor incorporated into a self-adhesive strip, which can be applied to the skin. Electrical interfacing (not shown) can be wired or wireless, and may perform as a data logger or a low power radio frequency transmitter or backscatter (e.g., RF-ID-type) communication device.

Conclusion

A novel class of nanocomposite membranes has been demonstrated for constructing moisture and chemi-sensitive scaffolds for potential applications, such as flexible sweat sensors. The nanocomposites are assembled by molecular or polymeric linkers that incorporate gold nanoparticles into a three-layer structured nanofibrous membrane. Impedance measurements of the nanocomposite membrane as a scaffold of chemiresistor-type platform have demonstrated the capabilities for ion detection in solutions with dissolved salts and changes of relative humidity in the atmosphere. This nanoparticle-nanofiber sensor platform is further demonstrated as a flexible sensor strip for detecting changes in sweating and perspiration of individuals before and after exercises, showing promising potentials for applications of the flexible nanocomposite scaffolds in wearable sweat sensors.

Various embodiments are shown and disclosed herein. The scope of the invention, while exemplified by the embodiments, is not limited thereby.

The word "about" means having a structure and function which is functionally similar with proportional changes in properties, dependent on quantitative changes. Typically, when the properties change linearly over a range, the word "about" may encompass a range of a factor of 2, i.e., 50% to 200%.

Example 2

The nanofibrous paper chemiresistor sensors employ dendronized nanoparticles that exhibit structurally tunable and negative-going responses to human breathing and sweating processes. The device consists of multilayered fibrous paper as a low-cost biocompatible matrix and dendron coated gold nanoparticles as designated sensing elements with tunable sizes, shapes, and structures. The ability to control the interparticle spatial interactions [Edel et al. 2016, Scultz et al. 2013] in a fibrous membrane represents an important pathway to utilize their unique electrical and optical properties for constructing the 3D sensing interfaces. The multilayered fibrous membrane consists of a cellulose nanofiber (CN) and an electrospun poly(acrylonitrile) (PAN), nanofibrous layer, sup-ported on a nonwoven poly(ethylene terephthalate) (PET), film.[Mat et al 2010] The membrane paper features an extremely high surface to volume ratio and nanofiltration capability. With metal nanoparticles, which are widely exploited as sensing or biosensing materials, different molecules or biomolecules have been utilized as interparticle linkers ranging from alkyl dithiols or functionalized thiols to polymers or biopolymers [Ahmad et al. 2015, Lim et al 2007]. In comparison to traditional linkers, dendrimers represent a class of macromolecules with well-defined 3D branched structure exhibiting a high degree of functionality and versatility. Dendrimers featuring multiple "wedges" and dendrons featuring single "wedge" are not only well defined as structural building blocks, but also have controllable sizes ranging from 1 to 30 nm depending on their generation.[Kaga et al. 2016, Albrecht et al. 2016] In particular, dendrimer-nanoparticle conjugates have been attracting considerable interest in medicine [Caminade et al. 2015, Parat et al 2010], drug delivery [Mullen et al. 2010], vapor sorption [Krasteva et al 2007], diagnostics [Astruc 2012] and electrochemical biosensors for enzyme immobilization [Hasanzadeh et al. 2014]. The exploration of size- and structure-tunable dendrons as interparticle linkers for the assembly of gold nanoparticles and the embedding of them in the flexible and nanofibrous membrane paper represent a pathway for design of highly sensitive interfacial materials for addressing some of challenges in wearable sensors and biosensors.

Dendrons or dendrimers are utilized for the coating of gold nanoparticles (Au NPs). The process involves thiolate binding of dendrons on the surface of gold nanoparticles and subsequent interparticle linkage via interactions of the immobilized dendrons. The dependence of the interparticle interactions on both the size and structure of dendrons and nanoparticles leads to intriguing optical and electrical properties of the resulting materials. The optical properties facilitate the assessment of the interparticle interactions and arrangements. The electrical properties of the nanofibrous membrane matrix with dendronized nanoparticles are harnessed for exploring the multiple hydrophilic/hydrogen-bonding sites in a 3D structural interface for sensing applications in moisture-dominant environment such as human breathing and sweating. The structurally tunable negative-going response characteristics, in contrast to the positive-going response characteristics for most chemiresistors, provides a new sensor design strategy for constructing sensor arrays for complex sensing environment. In addition, these low-cost sensing materials are highly versatile in various types of noninvasive and disposable applications due to the high surface area to volume ratio of the fibrous paper and the printable microelectrodes with minimum use of the dendronized nanoparticles. For example, the paper devices can be formatted as strips of different sizes or shapes with embedded electrical plug-in module, and an individual can place such a strip in a premade mask for breath monitoring or in a premade bandage for sweat monitoring.

Experimental Section

Synthesis of Dendrons: LG-$N_3$ dendron was synthesized according to previously published procedure [Wang et al. 2014], and then coupled with lipoic propargyl ester, which upon deprotection of the peripheral OH groups yielded deLG-SS. SG-$N_3$ dendron and the final deSG-SS fragment were synthesized in a similar fashion.

Synthesis and Assembly of gold nanoparticles having dendrons (AuNPs@Dendrons): The synthesis of gold nanoparticles involved the use of acrylate as both reducing and capping agent in an aqueous solution of $HAuCl_4$ [Njoki et al. 2007]. For example, in the synthesis of 30 nm nanoparticle seeds, an aqueous solution of $HAuCl_4$ ($2.0\times10^{-4}$ M) was mixed with sodium acrylate ($12.0\times10^{-3}$ M) and the mixture was stirred at controlled room temperature. Gold nanoparticles with diameters larger than the seeds were prepared by seeded growth via reduction of $AuCl_4$ in the presence of pre-synthesized Au seeds. Briefly, the seeds underwent a seeded aggregative growth reaction in the presence of $HAuCl_4$ under a range of controlled concentrations of the reducing and capping agents (sodium citrates) to form large-sized Au nanoparticles. The particle size was controlled by varying the concentration of the seeds and the concentration of $AuCl_4$. Then Au NPs ($0.73\times10^{-12}$ M) with different sizes (30, 47, and 58 nm) were resuspended into methanol solution or doubly distilled $H_2O$ followed by drop by drop addition of the dendrons in methanol solution. The disulfide functional group of dendrons serves as an anchoring group to gold surface through gold-thiolate binding upon breaking down the disulfide linkage. The concentrations of the gold nanoparticles and the dendrons are precisely controlled so that the relative rates of the dendron-citrate exchange reaction and the dendron-dendron linking reaction can be controlled to achieve the desired interparticle spatial properties. The dendronized nanoparticles were incorporated into the paper by pipetting and casting the solution with controlled concentration and volume, or inkjet printing of the nanoink with a controlled concentration and speed. UV-vis spectra were acquired with an HP 8453 spectrophotometer. Spectra were collected over the range of 200-1100 nm. TEM analysis was performed using an FEI Tecnai T12 Spirit Twin TEM/scanning electron microscopy (SEM) electron microscope (120 kV).

Sensor Measurements: Computer-interfaced multichannel Keithley (Model 2700) instrument was used to measure the lateral resistance of the nanostructured thin films on the laser-written devices, which were housed in a Teflon chamber with tubing connections to vapor and N2 sources (at 22±1° C.). The concentration was controlled by bubbling dry $N_2$ gas through the solvent using a calibrated Aalborg mass-flow controller (AFC-2600). The vapor generating system consisted of multichannel module linked to different vapor sources.

Results and Discussion

The dendronized Au NPs, along with their interparticle linkages, are embedded in the fibrous membranes such as nanofibrous membrane-type paper, forming a physically flexible and chemically tunable nanocomposite scaffold. In the scaffold, the distance between the nanoparticles is well-defined due to the semi-rigid character of the dendrons and lack of in-depth interpenetration among the dendron shells. In other words, the interparticle forces involve a combination of hydrogen-bonding and van der Waals interactions between the partially interpenetrating dendrons.

Figure 20A:
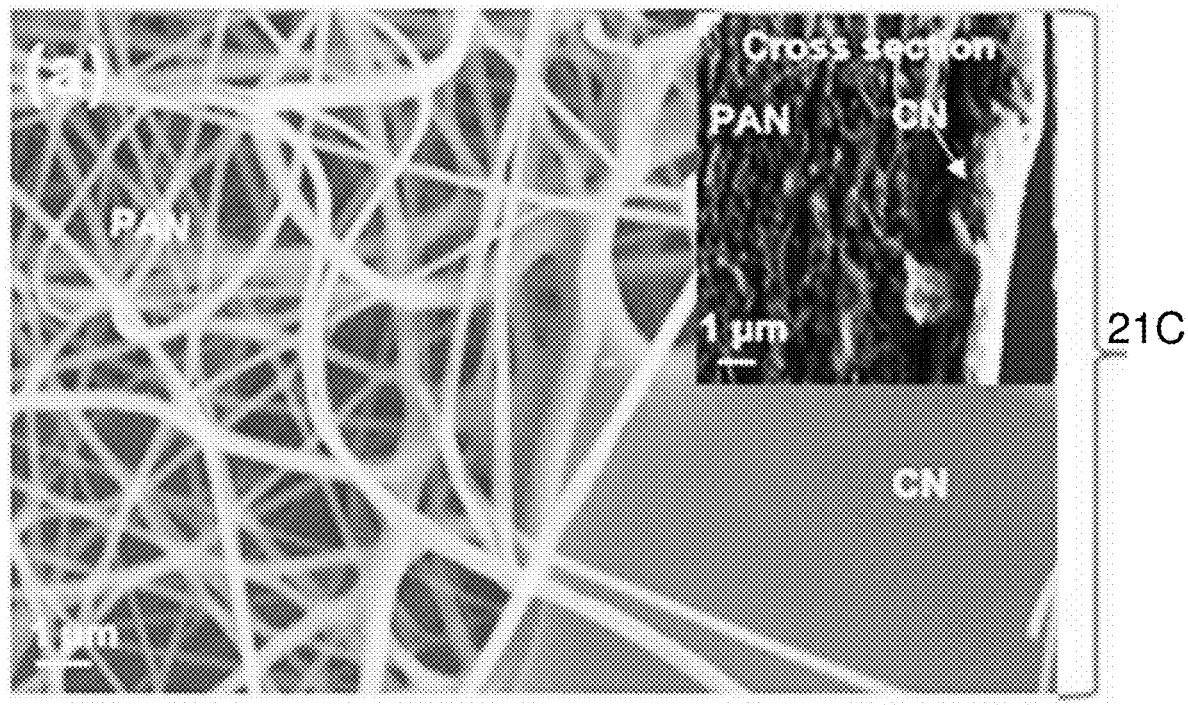
FIGS. 20A, 20B, 20D, 20E, and 20F show SEM (FIG. 20A) and TEM (FIG. 20B) images of the nanofibrous paper (CN/PAN/PET) showing CN layer and PAN fibers, with the cross section being shown in the inset in FIG. 20A.
Figure 20B:
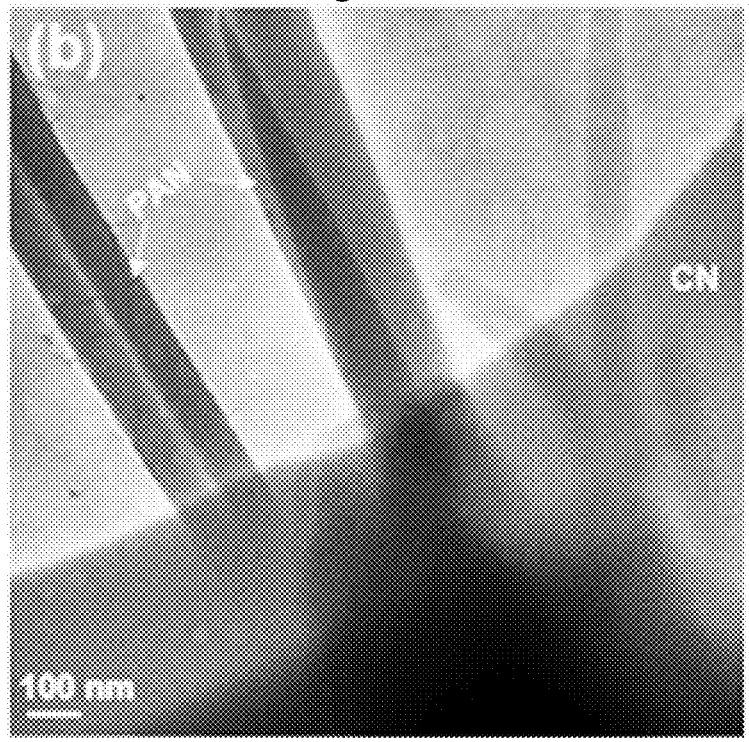
Figure 20C:
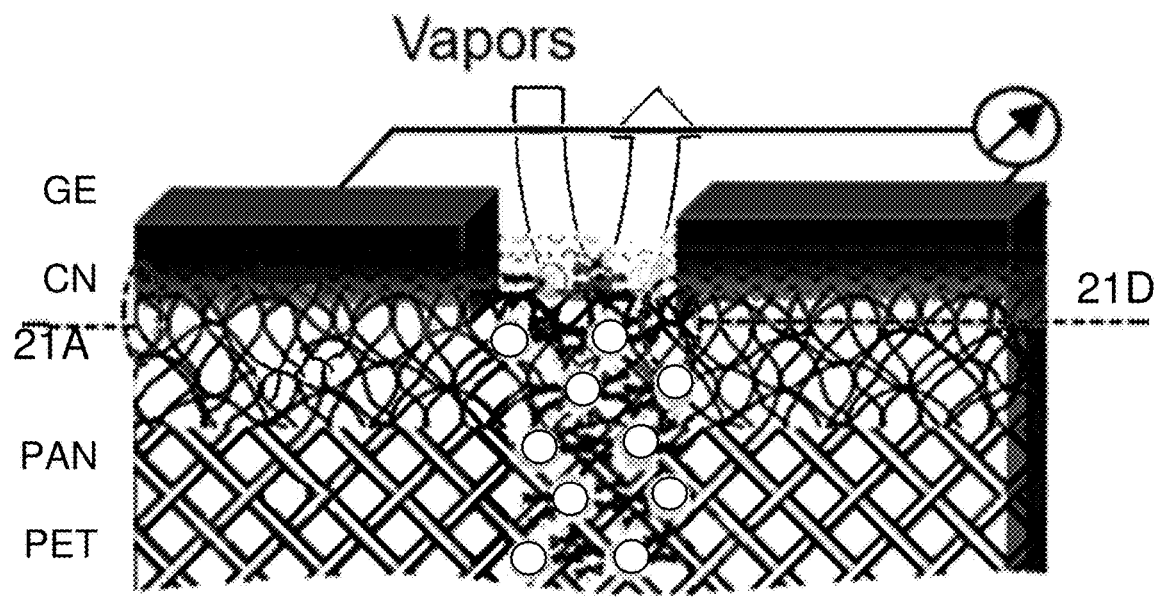
FIG. 20C shows a sensor scheme, and the representative locations from which FIGS. 20A (SEM) and FIG. 20D (TEM) are derived.
Figure 20D:
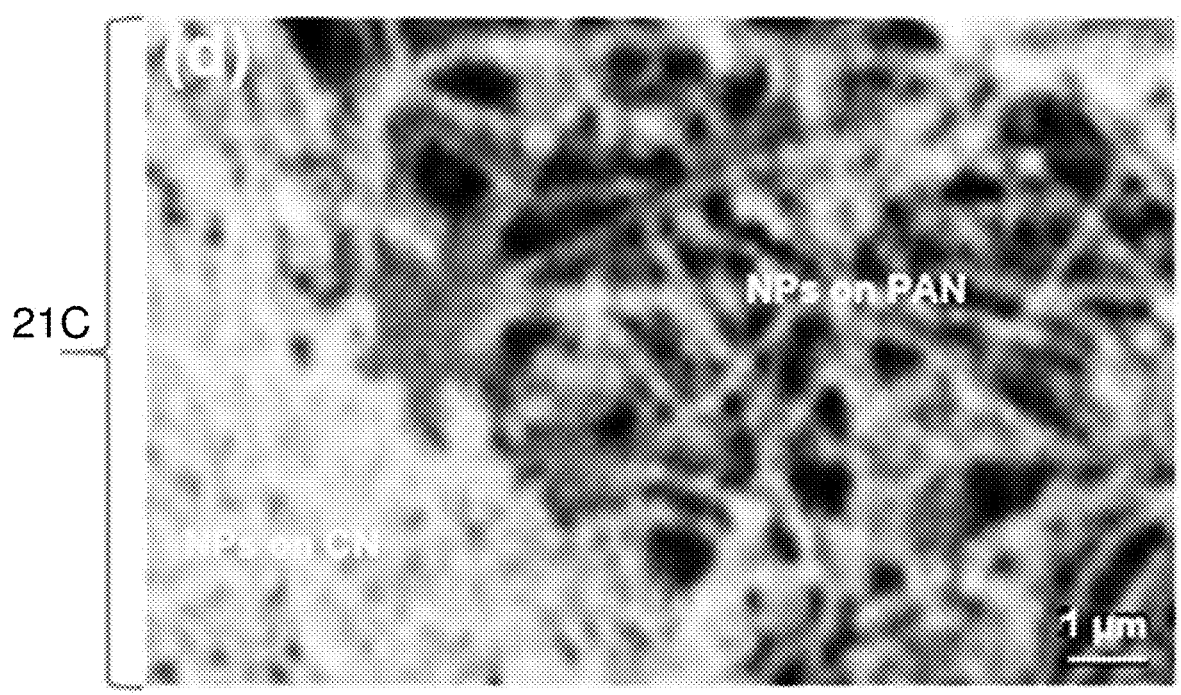
Figure 20E:
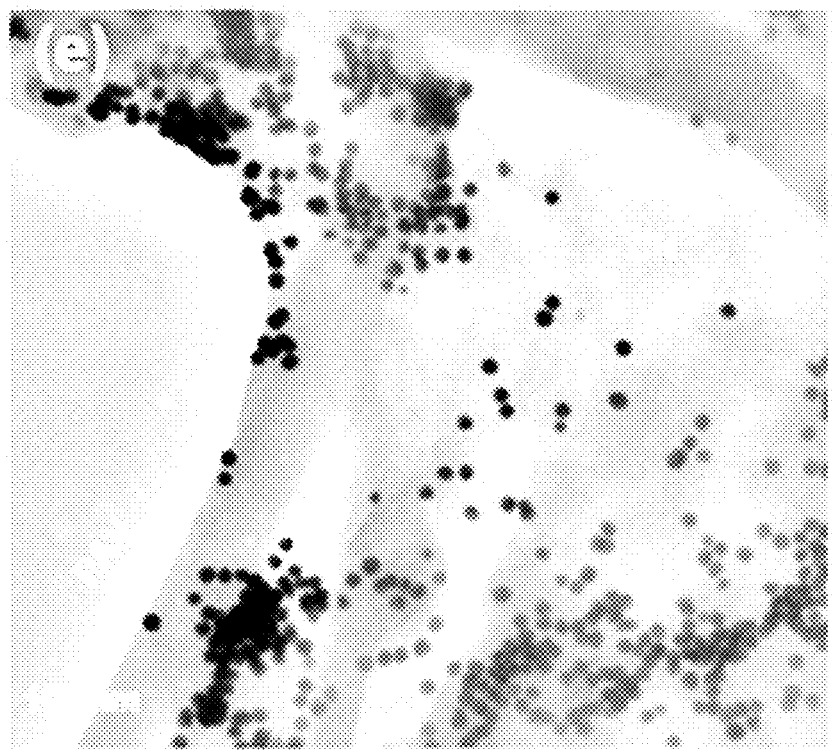
Figure 20F:
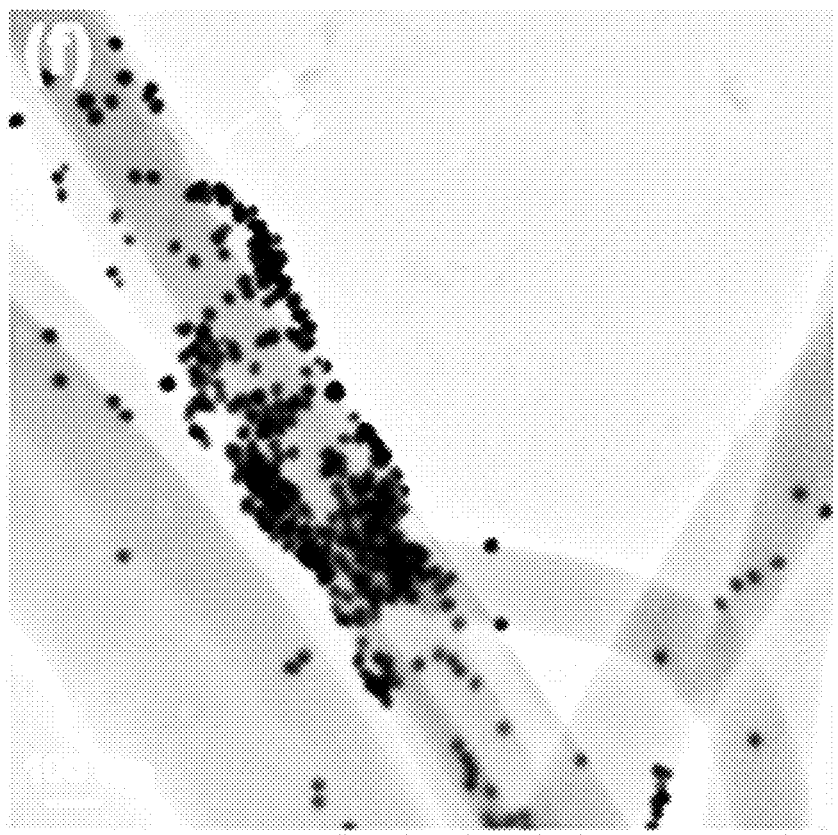

The structural and spatial characteristics defined by the multiple hydrogen-bonding and van der Waals interactions between the individually dendronized nanoparticles constitute the basis for harnessing the structurally and spatially tunable interparticle properties. To exploit such interparticle properties, the AuNP@dendrons are incorporated into a multilayered fibrous membrane-type paper with printed electrodes as an electrically responsive sensing scaffold. The interparticle properties of this type of 3D nanocomposite scaffold are expected to be sensitive to perturbation by molecular adsorption, leading to a change in the electrical properties. As shown in FIGS. 20E and 20F, AuNP@dendron assemblies are embedded in the three-layered fibrous membrane paper, consisting of a cellulose (CN) nanofiber layer, a PAN nanofibrous layer, and a non-woven PET, layer [Ma et al. 2010] On this membrane-type nanocomposite platform, a gap (≈62 µm) defined by spray printed graphite (GE) or aerosol jet printed carbon electrodes (FIG. 20C). In comparison with the CN/PAN (FIGS. 20A, 20B), CN surface and the PAN fibers are clearly decorated with the dendronized Au NPs (FIGS. 20D-20F). Most of these dendronized Au NPs on the CN layer or PAN fibers display a clear aggregation, consistent with the interparticle interactions defined by the dendrons as discussed above.

Figure 21A:
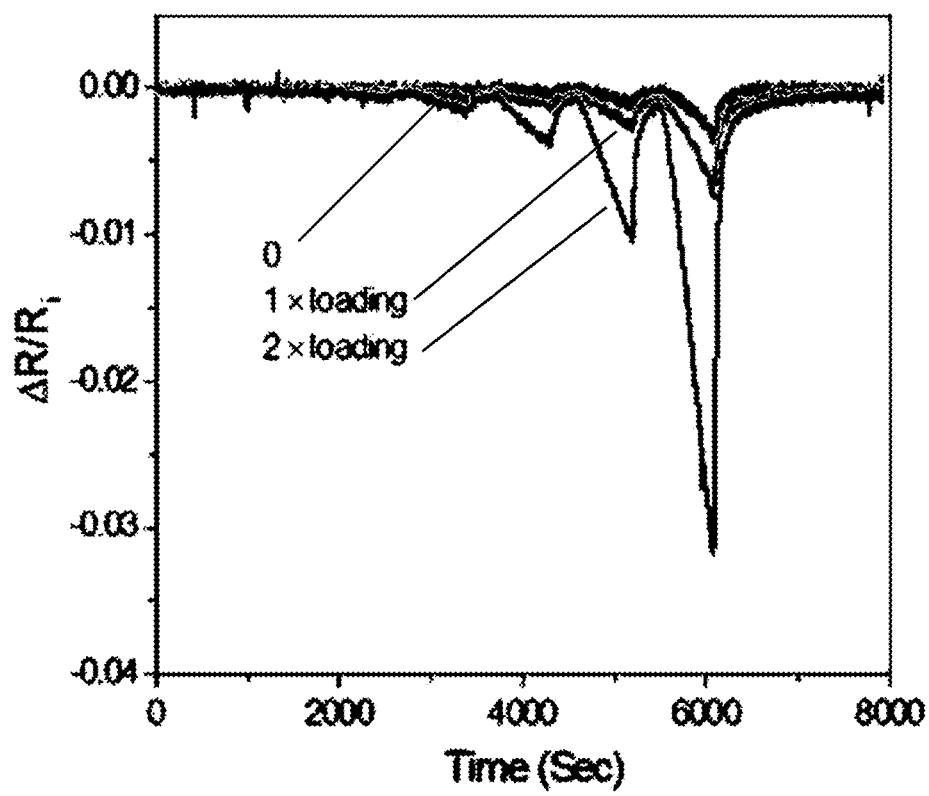
FIGS. 21A-21C show response profiles of the sensing scaffolds with different loading of gold nanoparticles with AuNPs@deSG-SS in the nanofibrous paper (0 upper curve), 1× loading ($2.04 \times 10^9$ NPs $mm^{-2}$, middle curve) and 2× loading ($4.08 \times 10^9$ NPs $mm^{-2}$, lower curve) of the AuNPs@deSG-SS solution, for water (FIG. 21A), ethanol (FIG. 21B), and acetone (FIG. 21C) vapors respectively.
Figure 21B:
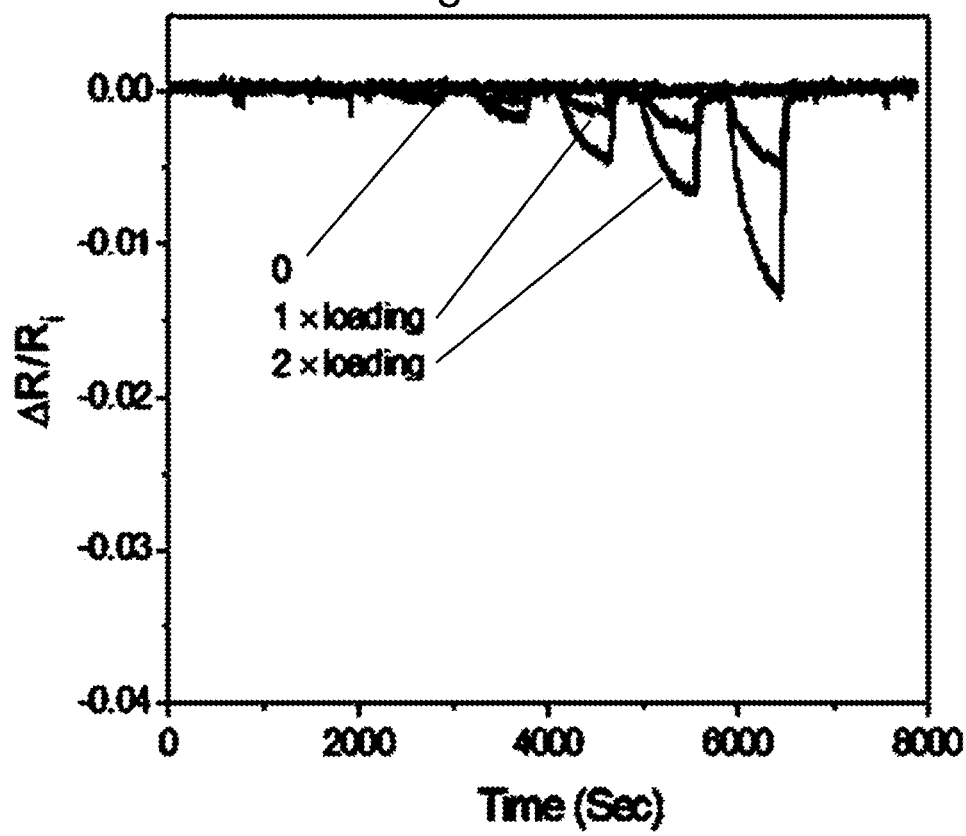
Figure 21C:
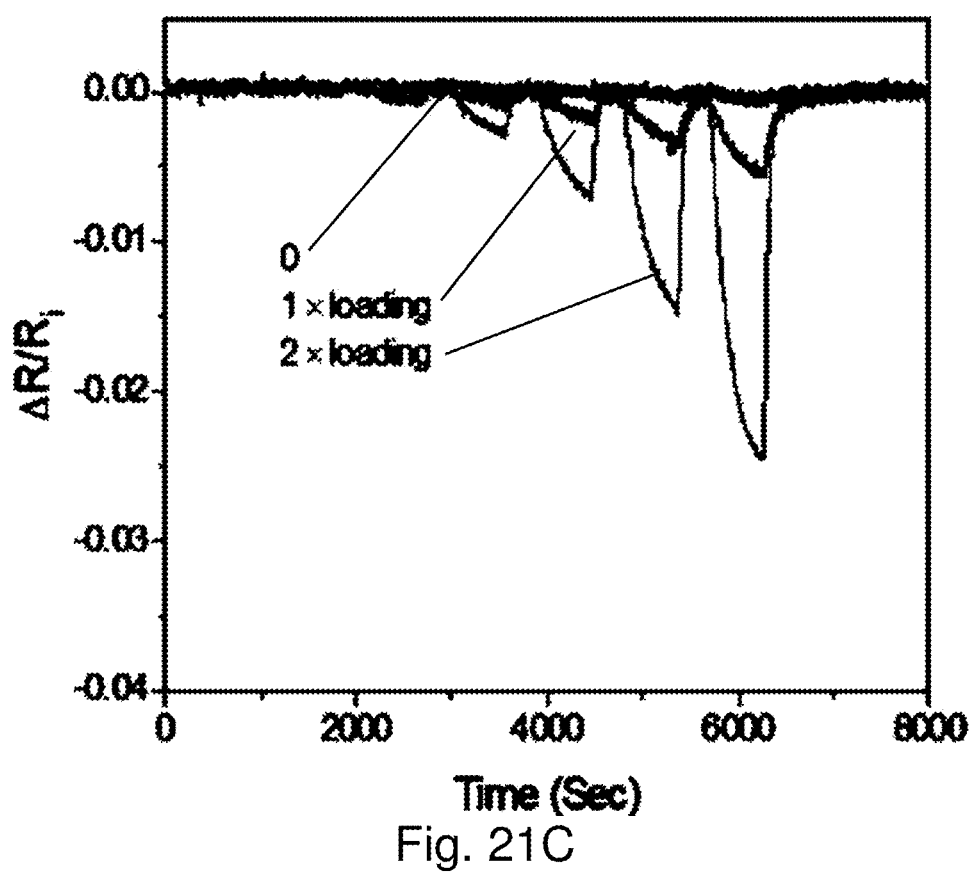

The change in electrical properties as a result of the adsorption of volatile organic compounds (VOCs) in the above nanocomposite can be detected by the printed microelectrodes, which has important applications for environmental monitoring of VOC pollution in air, and of great interest for human breath sensing of VOC biomarkers from various diseases (e.g., acetone as breath biomarker associated with diabetes). As shown in FIGS. 21A-21C, upon exposure to water, ethanol, or acetone vapors, changes in interparticle distances and dielectric properties translate to a change in electrical conductivity with its sensitivity and selectivity depending on the molecular interaction between the VOCs and the interparticle dendron shells. In comparison with the blank CN/PAN/PET paper device without the nanoparticle assemblies, the nanocomposite CN/PAN/PET paper device with different loading of gold nanoparticles with deSG-SS dendrons (AuNPs@deSG-SS) as the sensing element shows a clear negative-going response profile for the relative resistance change ($\Delta R/Ri$) in contact with water (FIG. 21A), ethanol (FIG. 21B), and acetone (FIG. 21C) vapors.

In general, the increase in the amount of AuNPs@deSG-SS assemblies in the fibrous membrane is found to lead to a larger response, which is consistent with the electrical characteristics of the nanoparticle assemblies. Note that the responses to other alcohol vapors such as methanol and propanol also display negative-going response profiles. These response profiles exhibit a remarkable contrast to most of the traditional chemiresistors assembled by polymers or nanoparticles with molecular linkers (alkyl dithiols and alkyl dicarboxylic acid) on flexible or rigid substrates (PET and glass), which exhibited often positively going response characteristics in terms of $\Delta R/Ri$,[Wang et al 2007, Wang et al. 2010, Yin et al. 2011, Shan et al. 2014, Zhao et al. 2015, Olichwer et al. 2016, Ghosh et al. 2017, Segev-Bar et al. 2017] but less often negative-going responses depending on the interparticle dielectric medium properties [Wang et al. 2010, Yin et al. 2011, Kim et al. 2014, Ibanez et al 2012]. In the assembly of the dendronized Au NPs, the persistence of the negative-going response profiles observed in this work is indicative of a significant impact of an increase of the interparticle dielectric medium constant as a result of the highly branched dendrons with both hydrophilic and hydrophobic structures in the 3D matrix on the electrical conductivity. Such an impact imparts a unique response characteristic to the nanofibrous membrane paper embedded with dendronized nanoparticles as novel sensing interface.

Figure 21D:
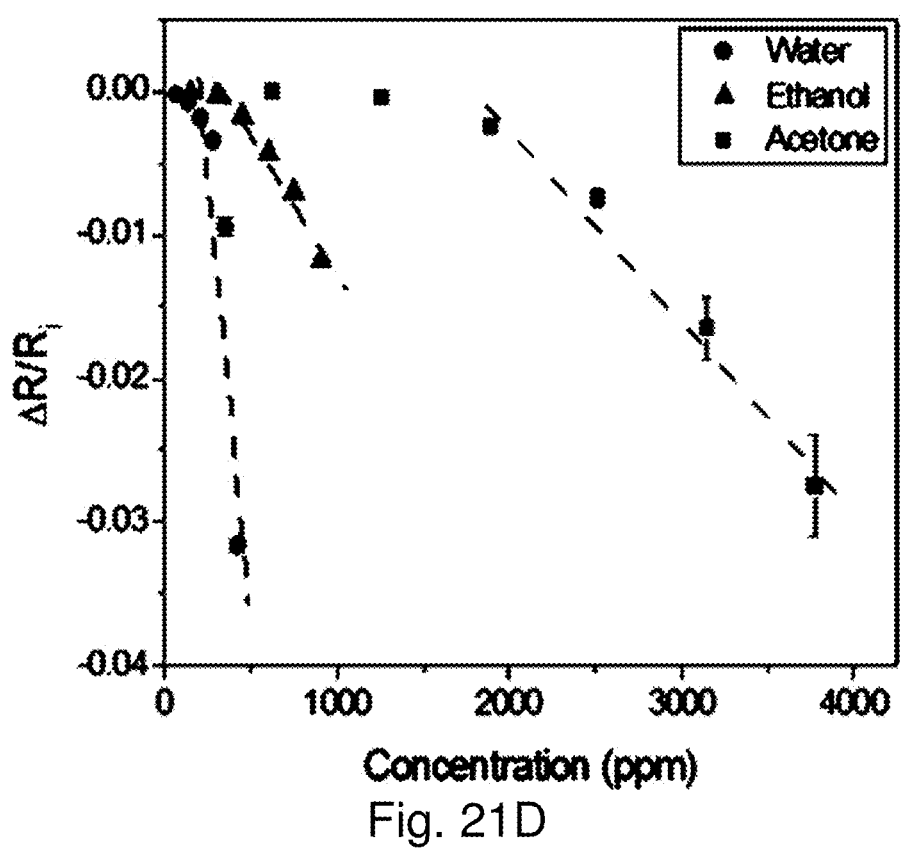
FIG. 21D shows the sensor response sensitivities (ppm (M)) for water ($-1.9 \times 10^{-4}$, circle) ethanol ($-1.5 \times 10^{-5}$, triangle), and acetone ($-1.1 \times 10^{-5}$, rectangle).

It is evident that the magnitude of the negative-going response scales with the vapor concentration. With the same amount of AuNPs@deSG-SS assemblies in the fibrous membrane devices, the response sensitivity (FIG. 21D) for water vapor ($-1.9\times10^{-4}$) is found to be higher than that for ethanol vapor ($-1.5\times10^{-5}$) and acetone vapor $-(-1.1\times10^{-5})$. Note that the 3D-paper based sensor also shows a higher sensitivity than that derived from similar nanoparticle assemblies on a 2D-substrate, such as glass or polyimide. For example, the response sensitivity for acetone was found to be higher than that observed in previous studies with 2D substrates ($4.0\times10^{-6}$) [Zhao et al. 2015].

The AuNPs@deSG-SS embedded membrane paper sensor is further tested as a flexible device for detecting human breathing and sweating. Such tests are significant considering the facts that human breathing relates the physical conditions or performances, and that the human breath exhale contain various volatiles (e.g., under normal conditions, 5% $H_2O$ vapor, a few ppm (V) of $H_2$, $CO_2$, and $NH_3$, and ≈1 ppm (V) of acetone, methanol, ethanol, and other VOCs) [Vaks et al. 2014] which can be used to diagnose some conditions related to human health, such as lung cancer and diabetes [Zhao et al. 2016]. The pattern of exhale breath is either a strong predictor of diseases such as colorectal cancer and gastric cancer, or used as a unique breath print for illnesses such as chronic obstructive pulmonary disease, pneumonia, and asthma [Nakhleh et al. 2016].

To test the viability of the membrane-type paper device as a breath sensor in terms of inhale and exhale cycles, which are the more accessible and useful source for monitoring disorders and health of the human body than blood tests, response profiles of the device to breathing, perspiration, and sweating are measured.

Figure 22A:
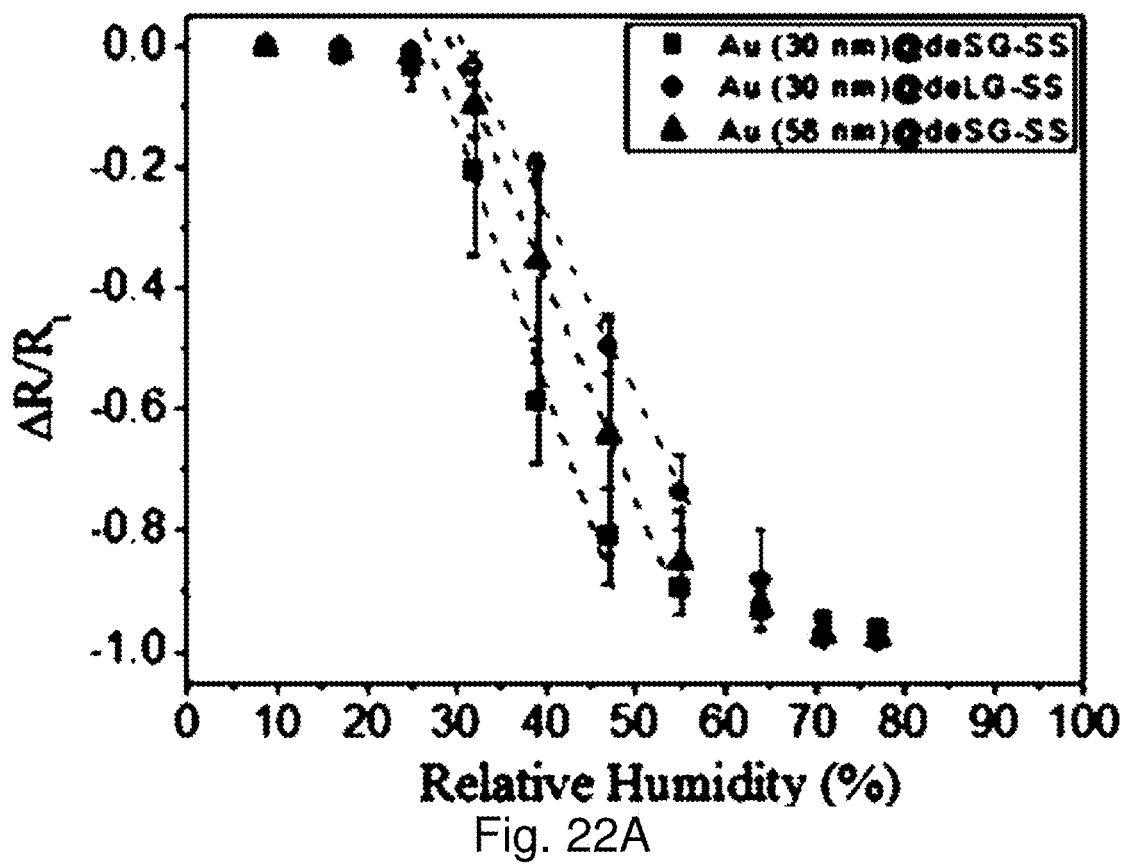
FIG. 22A shows a plots of $\otimes R/R_i$ versus RH %, showing a linear relationship in the range of 22-50% RH %, with slopes of −0.035, −0.029, and −0.031 for Au30 nm@deSG-SS, Au30 nm@deLG-SS, and Au58 nm@deSG-SS.
Figure 22B:
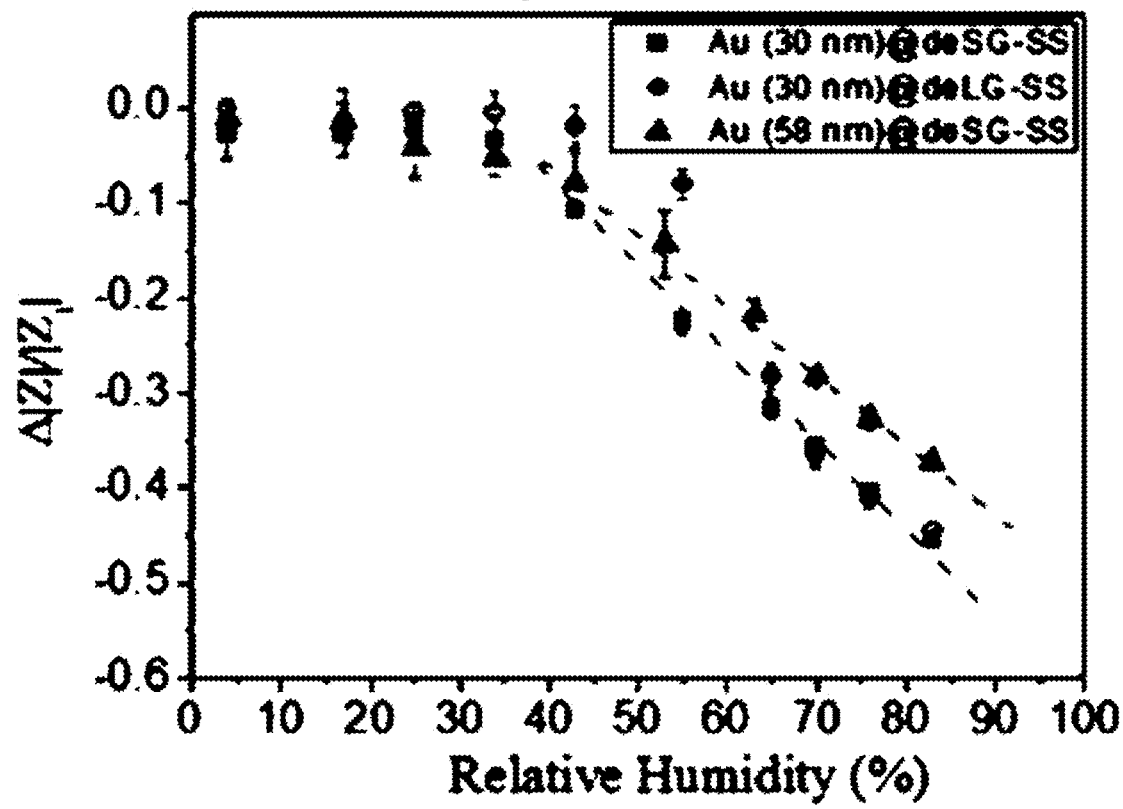
FIG. 22B shows response profiles recorded with three different sensing materials in the scaffolds: Au30 nm@deSG-SS (lower), Au30 nm@deLG-SS (upper), and Au58 nm@deSG-SS (middle), during the individual's normal breathing, holding the breath briefly and then taking deep breathing.

As shown by a typical set of chemiresistive sensing data for moisture exposure of the nanocomposite membrane paper device (FIG. 22A), the sensor responses to the change in relative humidity (RH %), display an approximately linear dependence on RH % in the range of 20-50%. It also depends on the size and structure of the sensing element: Au30 nm@deSG-SS shows a higher sensitivity (slope=−0.035) than that of Au30 nm@ deLG-SS and Au58 nm@deSG-SS. The response sensitivity and reversibility to the relative humidity change is further exploited as a means to monitor the human breathing. The breathing test involved a facemask embedded with the nanocomposite membrane sensor which records an individual's breath inhale and exhale cycles. A typical set of result (FIG. 22B) shows a well-defined and completely reversible pattern of negative-going responses under normal breathing condition. The magnitude of the responses is intensified upon holding the breath briefly and then taking deep breathing cycles of inhale and exhale. As a control, the breathing data collected from the same sensor device but without the nanocomposite sensing element, the response of which is much smaller and poorly defined. It should be noted that the unique porosity of the nanofibrous membrane paper played an important role in the well-defined response pattern and baseline characteristics, which is reflected by the lack of baseline drift as compared to the significant baseline drift for the same devices made using regular copy paper [Güder et al. 2016]. The nanocomposite sensing element (AuNPs@dendrons) is responsible for the response sensitivity due to the interactions between the volatile molecules (mostly water vapor) and the AuNPs@dendrons, which change the interparticle distances and dielectric properties and thus the electrical signal output. Again, the breathing response sensitivity depends on the chemical nature of the molecular and non-structural interactions in the membrane, as evidenced by the variance observed with different dendrons and particle sizes. This is further shown by the data taken under deep breathing condition, in which the magnitude of responses apparently display the following order: Au30 nm@deSG-SS>Au58 nm@deSG-SS for the same dendronized Au NPs, and Au30 nm@deSG-SS>Au30 nm@deLG-SS for the same particle size. In addition, the breathing patterns were also found to depend on the individual's breathing. Au30 nm@deLG-SS, and Au58 nm@ deSG-SS showed high sensitivity in high-moisture environment. This finding serves as an important milestone because the ability to discriminate high humidity changes is a key requirement for developing breath and sweat sensors, which upon introducing sensor array could increase the sensor's selectivity to different analytes, a feature useful for exploitation in personalized wearable sensor applications.

The flexible nanocomposite membrane sensor devices were also tested for monitoring human sweating process. Sweat analysis is known to contain physiologically and metabolically rich information that can be retrieved noninvasively, which is used for applications such as disease diagnosis, drug abuse detection, and athletic performance optimization [Gao et al. 2016, Koh et al. 2016, Kang et al. 2016].

Figure 22C:
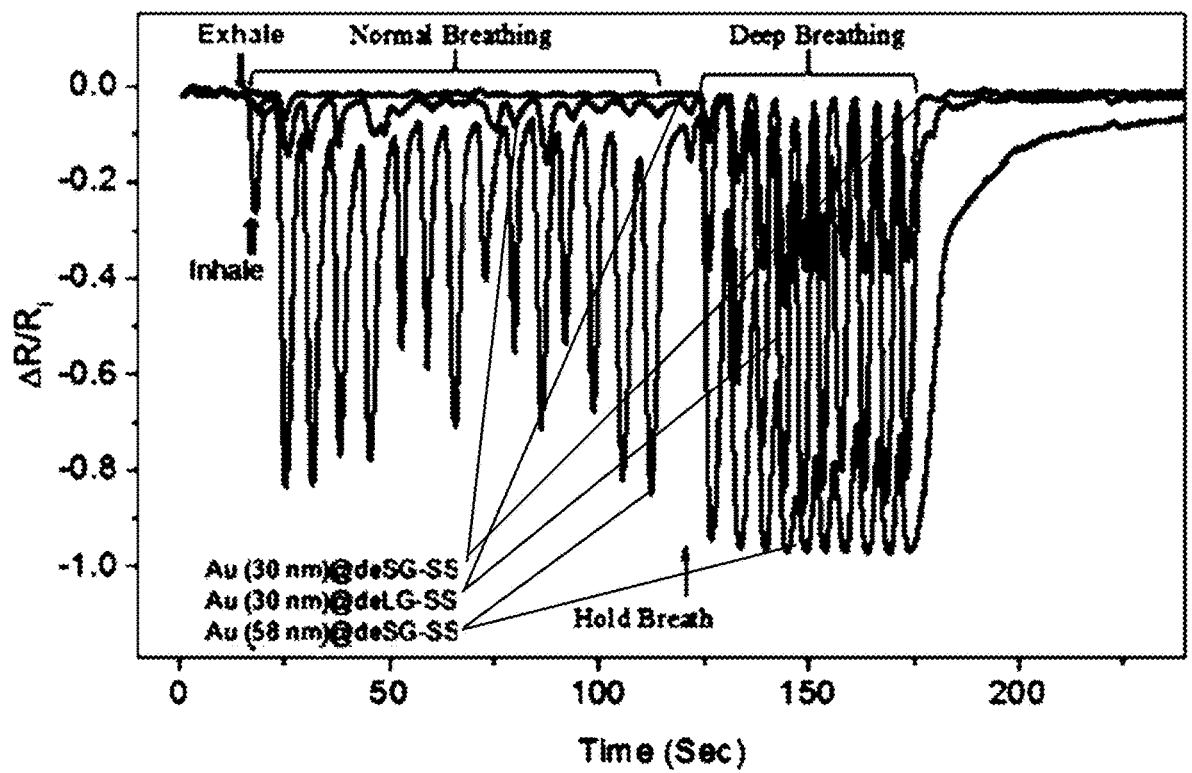
FIG. 22C shows a plot of impedance (at 1.3 kHz) versus RH %, with slopes (RH %>43%) of $-8.7 \times 10^{-3}$ and $-7.3 \times 10^{-3}$ for Au30 nm@deSG-SS and Au58 nm@deSG-SS.
Figure 22D:
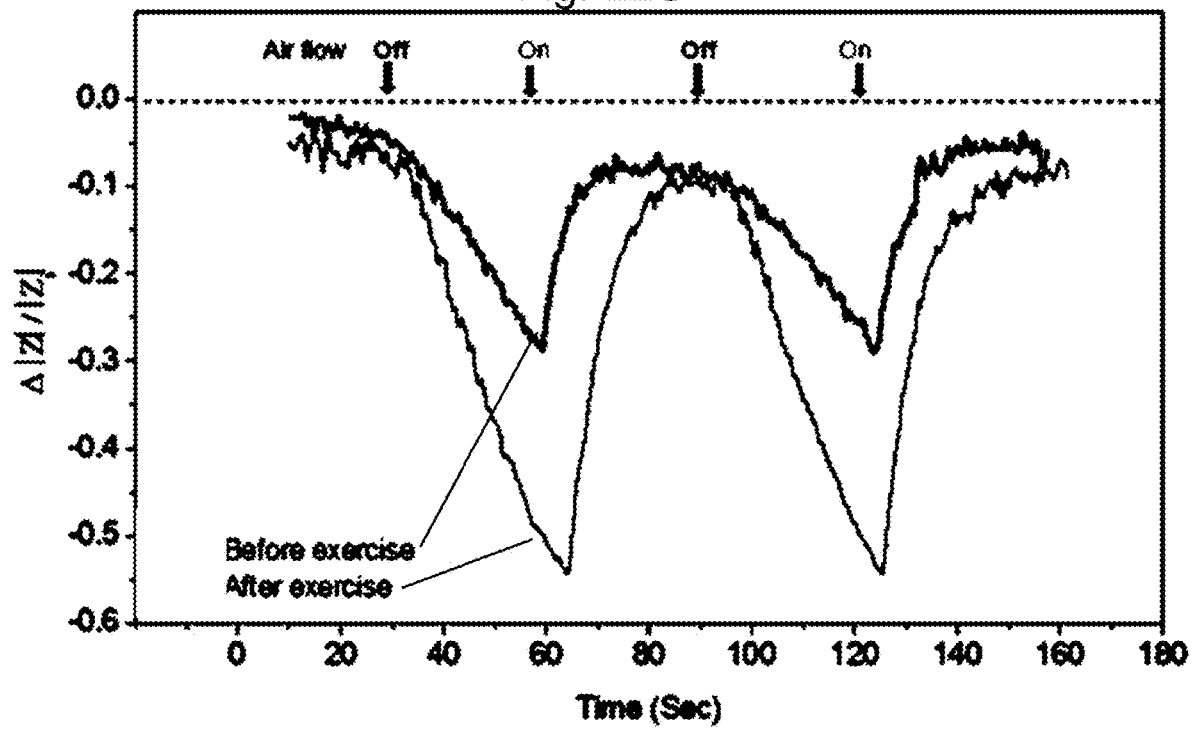
FIG. 22D shows response profiles (in terms of relative impedance change, $\otimes |Z|/|Z_i|$) with a sensor device of Au30 nm@deSG-SS recorded during perspiration test for an individual before (upper) and after (lower) min exercise.

To monitor perspiration, a stopped air-flow manifold with the nanocomposite sensor device being embedded inside was placed on the palm. When the air-flow system was turned off (stopped), the response signal came from sweating. The sensing mechanism takes advantage of the reversible moisture response characteristics of the sensor device, as shown by a typical set of impedance response data as a function of RH % (FIG. 22C), exhibiting an approximate linear dependence in the range of RH %>43%. Similar to the breathing data, the sensor with Au30 nm@deSG-SS displays a higher sensitivity (slope=−8.7×10$^{-3}$) than that of Au30 nm@deLG-SS and Au58 nm@deSG-SS. By collecting data of sweating for an individual before and after exercise (FIG. 22D), reversible response profiles are evident. An analysis of the response data indicates that the perspiration detected in terms of RH % corresponds to 60% before exercise and 87% after exercise, very high sensitivity to the perspiration under such a relatively high moisture condition. The sweat sensing capability is further substantiated by testing volunteers with absent or excessive sweating (hypohidrosis or hyperhidrosis), demonstrating the viability of the flexible nanocomposites for sweat sensor applications.

Conclusions

A membrane-type composite sensing interface consisting of multilayered fibrous paper and dendronized gold nanoparticles with tunable sizes, shapes, and structures has been demonstrated to enable 3D sensitive interface with structural tunability and molecular sensitivity for wearable physiological monitoring. This type of tunability by a combination of nanoparticles, dendrons, and membrane-type 3D scaffold with controllable sizes and structures is to our knowledge the first example in constructing sensing interfaces. Dendrons with tunable molecular sizes, structures, and multiple hydrogenbonding sites function as an interparticle linkage of gold nanoparticles, leading to well-defined interparticle spatial, optical, and electrical properties. The interparticle interactions are shown to be tunable by both dendron size and nanoparticle size, as evidenced by the size dependencies of the red shift of the surface plasmon resonance band of gold nanoparticles and the different kinetics of the assembly processes. The interparticle spacing is characterized by a certain degree of inter interpenetration between deSG-SS and deLG-SS dendron shells immobilized on the nanoparticle surface to maximize the hydrogen-bonding on multiple dendron sites or van der Waals interactions. Theoretical simulation of the SP band spectral evolution shows a good agreement with the experimentally observed SP band, providing insights into the size- and structure-dependent interparticle interactions. The embedding of the sensing nanostructures in the 3D fibrous membrane paper constitutes a promising strategy for the creation of highly sensitive interfaces under conformal conditions to the human body for wearable human performance monitoring and point-of-care sensing applications.

Embedding the dendronized nanoparticle assemblies in a multilayer nanofibrous membrane serves as a nanocomposite scaffold, which was demonstrated as a structurally tunable chemiresistor featuring all negative-going response characteristics, in contrast to most conventional chemiresistive sensing profiles. The electrical properties of the nanofibrous membrane-type paper as a breath and sweat sensing scaffold have shown tunability in terms of sensitivity through manipulating an array of structural parameters including the generation and functional groups for the dendrons, the particle size, and their relative compositions.

REFERENCES

Each patent and publication cited herein is expressly incorporated herein by reference in its entirety.

Technologies for integration of the present sensor into a system are known from the following, each of which is expressly incorporated herein by reference in its entirety: U.S. Pat. Nos. 6,607,484; 6,819,247; 6,893,396; 6,942,615; 6,985,078; 7,029,852; 7,034,677; 7,044,908; 7,128,716; 7,171,312; 7,171,331; 7,174,277; 7,285,090; 7,353,136; 7,353,137; 7,407,484; 7,440,844; 7,463,142; 7,486,979; 7,552,031; 7,555,327; 7,559,902; 7,574,244; 7,574,245; 7,590,439; 7,598,878; 7,620,520; 7,627,451; 7,647,084; 7,650,177; 7,657,294; 7,657,295; 7,657,296; 7,658,612; 7,673,528; 7,684,843; 7,693,559; 7,701,332; 7,711,506; 7,731,517; 7,738,937; 7,753,685; 7,811,234; 7,825,815; 7,827,011; 7,856,339; 7,860,725; 7,869,850; 7,881,762; 7,881,862; 7,904,285; 7,959,567; 8,036,842; 8,060,171; 8,063,307; 8,070,508; 8,071,935; 8,094,009; 8,097,926; 8,107,920; 8,125,331; 8,126,675; 8,157,730; 8,157,731; 8,175,671; 8,190,224; 8,190,225; 8,195,264; 8,199,007; 8,204,786; 8,219,170; 8,228,188; 8,251,903; 8,275,635; 8,280,469; 8,280,681; 8,280,682; 8,284,046; 8,285,560; 8,308,489; 8,311,602; 8,315,685; 8,323,188; 8,323,982; 8,352,010; 8,352,172; 8,358,214; 8,369,936; 8,374,825; 8,382,590; 8,386,002; 8,396,527; 8,396,687; 8,398,546; 8,426,932; 8,428,675; 8,428,904; 8,449,471; 8,452,366; 8,467,133; 8,472,120; 8,477,425; 8,482,859; 8,488,246; 8,498,811; 8,512,242; 8,515,515; 8,515,537; 8,527,213; 8,528,185; 8,536,667; 8,553,223; 8,571,620; 8,579,834; 8,636,670; 8,638,228; 8,641,612; 8,652,409; 8,655,441; 8,660,814; 8,665,087; 8,684,900; 8,688,406; 8,690,799; 8,696,616; 8,702,607; 8,702,627; 8,708,904; 8,714,983;

8,715,206; 8,731,512; 8,744,783; 8,755,535; 8,759,791; 8,764,657; 8,781,548; 8,788,002; 8,795,173; 8,798,702; 8,805,465; 8,812,130; 8,844,057; 8,852,098; 8,870,766; 8,888,701; 8,929,963; 8,929,965; 8,935,195; 8,942,776; 8,961,414; 8,961,415; 8,964,298; 8,965,473; 8,968,196; 8,984,954; 9,020,752; 9,028,405; 9,033,876; 9,042,596; 9,044,180; 9,050,471; 9,058,703; 9,060,714; 9,072,941; 9,078,610; 9,097,890; 9,097,891; 9,119,533; 9,125,625; 9,128,281; 9,129,295; 9,132,217; 9,134,534; 9,141,994; 9,147,144; 9,162,063; 9,165,117; 9,174,055; 9,182,596; 9,186,060; 9,186,098; 9,215,992; 9,216,528; 9,223,134; 9,229,227; 9,254,099; 9,254,383; 9,256,906; 9,258,350; 9,262,772; 9,265,453; 9,265,949; 9,267,793; 9,269,000; 9,270,627; 9,272,091; 9,282,574; 9,285,589; 9,289,175; 9,301,092; 9,301,719; 9,320,842; 9,326,731; 9,341,843; 9,349,234; 9,351,669; 9,366,862; 9,384,609; 9,389,260; 9,396,486; 9,398,856; 9,408,572; 9,412,273; 9,415,125; 9,426,433; 9,439,566; 9,439,567; 9,439,797; 9,442,070; 9,442,100; 9,445,720; 9,445,767; 9,453,774; 9,456,755; 9,462,979; 9,504,423; 9,514,278; 9,515,417; 9,521,962; 9,522,317; 9,524,597; 9,529,385; 9,532,737; 9,536,449; 9,538,921; 9,538,980; 9,572,647; 9,582,035; 9,582,072; 9,582,080; 9,582,833; 9,590,438; 9,592,007; 9,594,402; 9,597,004; 9,598,282; 9,613,659; 9,615,798; 9,619,213; 9,620,000; 9,625,330; 9,630,011; 9,636,992; 9,636,993; 9,643,091; 9,654,200; 9,662,069; 9,669,699; 9,669,700; 9,687,183; 9,691,428; 9,696,833; 9,701,190; 9,703,751; 9,707,466; 9,717,455; RE44,408; RE45,766; 20010049471; 20020028988; 20020120203; 20030076968; 20030163287; 20030181795; 20030194205; 20030195398; 20030204132; 20040029183; 20040133081; 20040135684; 20040152956; 20040152957; 20040158194; 20040204915; 20050080322; 20050080566; 20050148828; 20060052983; 20060143645; 20060252999; 20060254369; 20060293714; 20070016096; 20070063850; 20070100666; 20070106138; 20070111753; 20070112542; 20070118328; 20070152811; 20070197881; 20070208542; 20070255176; 20070270672; 20080030330; 20080077440; 20080146334; 20080146892; 20080161654; 20080161655; 20080162088; 20080167535; 20080167536; 20080167537; 20080167538; 20080167539; 20080171919; 20080171920; 20080171921; 20080171922; 20080220535; 20080246629; 20080262376; 20080275309; 20080306357; 20080318678; 20080319781; 20080319786; 20080319787; 20080319796; 20080319855; 20080320029; 20080320030; 20090006457; 20090006458; 20090093985; 20090112071; 20090171166; 20090174547; 20090177068; 20090212941; 20090322513; 20100076692; 20100081895; 20100121227; 20100122832; 20100152621; 20100176952; 20100217099; 20100241464; 20100241465; 20100249557; 20100286532; 20110003610; 20110004072; 20110034912; 20110035190; 20110054359; 20110070835; 20110082484; 20110092825; 20110098112; 20110106627; 20110145162; 20110191044; 20110213225; 20110213271; 20110213272; 20110213273; 20110213274; 20110223583; 20110282828; 20110288574; 20110298613; 20110319729; 20120010642; 20120050038; 20120075168; 20120095352; 20120123232; 20120123960; 20120143495; 20120143514; 20120146784; 20120149996; 20120150483; 20120165617; 20120172783; 20120172792; 20120190941; 20120190942; 20120190943; 20120190951; 20120194418; 20120194419; 20120194420; 20120194549; 20120194550; 20120194551; 20120194552; 20120194553; 20120197093; 20120197098; 20120197222; 20120197737; 20120200488; 20120200499; 20120200601; 20120203081; 20120203453; 20120203491; 20120203511; 20120206322; 20120206323; 20120206334; 20120206335; 20120206485; 20120209088; 20120212398; 20120212399; 20120212400; 20120212406; 20120212414; 20120212484; 20120212499; 20120218172; 20120218301; 20120226111; 20120226112; 20120226130; 20120235883; 20120235884; 20120235885; 20120235886; 20120235887; 20120235900; 20120236030; 20120236031; 20120242678; 20120242697; 20120242698; 20120244807; 20120245439; 20120245447; 20120246788; 20120249797; 20120265296; 20120265477; 20120273354; 20120277546; 20120283577; 20120283578; 20120296175; 20120296184; 20120296191; 20130013333; 20130030711; 20130059396; 20130060480; 20130066395; 20130096466; 20130103416; 20130127980; 20130131519; 20130144564; 20130151699; 20130172691; 20130211788; 20130216989; 20130238276; 20130245486; 20130274642; 20130278631; 20130311084; 20130314303; 20130338470; 20130346148; 20140012105; 20140018638; 20140039290; 20140051946; 20140052567; 20140058272; 20140063054; 20140063055; 20140081175; 20140081578; 20140081667; 20140088442; 20140091811; 20140094136; 20140095102; 20140107495; 20140107498; 20140107932; 20140114699; 20140115008; 20140122496; 20140122536; 20140122537; 20140143064; 20140156698; 20140172358; 20140180018; 20140180024; 20140180025; 20140180598; 20140180720; 20140180993; 20140181108; 20140187872; 20140187873; 20140188874; 20140197947; 20140200426; 20140202264; 20140203797; 20140203972; 20140206955; 20140213854; 20140213855; 20140213856; 20140213857; 20140213938; 20140214552; 20140214836; 20140214873; 20140214874; 20140214903; 20140220525; 20140221730; 20140221769; 20140221770; 20140221773; 20140221774; 20140221775; 20140221776; 20140221849; 20140221850; 20140222174; 20140222732; 20140222733; 20140222734; 20140222735; 20140222804; 20140222847; 20140222848; 20140222849; 20140222850; 20140222851; 20140223406; 20140223407; 20140223421; 20140232516; 20140249381; 20140267299; 20140274216; 20140275824; 20140275855; 20140275898; 20140285402; 20140287833; 20140288394; 20140288396; 20140303452; 20140303508; 20140303520; 20140306814; 20140306834; 20140306835; 20140308636; 20140308639; 20140308902; 20140309838; 20140309919; 20140309930; 20140309939; 20140309940; 20140310105; 20140310223; 20140310274; 20140310275; 20140310276; 20140310284; 20140310294; 20140310295; 20140310296; 20140310297; 20140310298; 20140310379; 20140310702; 20140316229; 20140316885; 20140317039; 20140317042; 20140317119; 20140317135; 20140343370; 20140343371; 20140343380; 20140344208; 20140344282; 20140347491; 20140349256; 20140349257; 20140350883; 20140368643; 20140378853; 20150005680; 20150025338; 20150031967; 20150032505; 20150047091; 20150054628; 20150057512; 20150057516; 20150058110; 20150058133; 20150061895; 20150063202; 20150078140; 20150080741; 20150080746; 20150088007; 20150102208; 20150111088; 20150119657; 20150123641; 20150126824; 20150126873; 20150140397; 20150141772; 20150148623; 20150148624; 20150148625; 20150148632; 20150148635; 20150148636; 20150157220; 20150164404; 20150168365; 20150170540; 20150173674; 20150178915; 20150181840; 20150182322; 20150182843; 20150185088; 20150199010; 20150216484; 20150245797; 20150248833; 20150254724; 20150254964; 20150259110; 20150261254; 20150265214; 20150265217; 20150269369; 20150271164; 20150272494; 20150276396; 20150281424; 20150281811; 20150282767; 20150305682; 20150306505; 20150309316; 20150309535; 20150309563; 20150312712; 20150316419; 20150320588; 20150331512; 20150331997; 20150335283; 20150335284; 20150339570; 20150340891; 20150350752; 20150351655; 20150351670; 20150351671; 20150351672; 20150351673; 20150355045; 20150356093; 20150359457; 20150359489; 20150363563; 20150370320; 20150374289; 20150379238;

20160007933; 20160009169; 20160009179; 20160009181; 20160009223; 20160009293; 20160009334; 20160009335; 20160009336; 20160009337; 20160009338; 20160009339; 20160011003; 20160011598; 20160011599; 20160012545; 20160012652; 20160012721; 20160012723; 20160012749; 20160014205; 20160014252; 20160015267; 20160015268; 20160015280; 20160015299; 20160015303; 20160015972; 20160018257; 20160019813; 20160022210; 20160030078; 20160030809; 20160034663; 20160034764; 20160040998; 20160041820; 20160042534; 20160045162; 20160045654; 20160051184; 20160051185; 20160051806; 20160058328; 20160058378; 20160058380; 20160062333; 20160066716; 20160066894; 20160067494; 20160073886; 20160074276; 20160074661; 20160075175; 20160075177; 20160075226; 20160082772; 20160086193; 20160089089; 20160112684; 20160112775; 20160113503; 20160117937; 20160118640; 20160120433; 20160120434; 20160128615; 20160128638; 20160129280; 20160134642; 20160140870; 20160141718; 20160143547; 20160148103; 20160148215; 20160148531; 20160148597; 20160151628; 20160157779; 20160165852; 20160165853; 20160166203; 20160166786; 20160166930; 20160169930; 20160171623; 20160171846; 20160174039; 20160174099; 20160174857; 20160174891; 20160174903; 20160178392; 20160180222; 20160182625; 20160184703; 20160187654; 20160189534; 20160195566; 20160199249; 20160202755; 20160205450; 20160206232; 20160209648; 20160210416; 20160217259; 20160222539; 20160228640; 20160232811; 20160233469; 20160233946; 20160234176; 20160242646; 20160243927; 20160245686; 20160249832; 20160249853; 20160258758; 20160267238; 20160269692; 20160270126; 20160270671; 20160270700; 20160274048; 20160277528; 20160278647; 20160280069; 20160287089; 20160287164; 20160287166; 20160296839; 20160301581; 20160307284; 20160313798; 20160314564; 20160317049; 20160317060; 20160321677; 20160322744; 20160324478; 20160338626; 20160338627; 20160338644; 20160338646; 20160339428; 20160342744; 20160349090; 20160349305; 20160349790; 20160351045; 20160354543; 20160360153; 20160361014; 20160367151; 20160367202; 20160374577; 20160374621; 20160375308; 20160376650; 20170000359; 20170000936; 20170005958; 20170010658; 20170010664; 20170010665; 20170010667; 20170010672; 20170011182; 20170011602; 20170014067; 20170020390; 20170020391; 20170020417; 20170020431; 20170020440; 20170020441; 20170020442; 20170023509; 20170024530; 20170024535; 20170024555; 20170024771; 20170026790; 20170027511; 20170030877; 20170032258; 20170046740; 20170048257; 20170055851; 20170055882; 20170055887; 20170055896; 20170068790; 20170078223; 20170079594; 20170080346; 20170086291; 20170086709; 20170087363; 20170090466; 20170091412; 20170091426; 20170091498; 20170095153; 20170095233; 20170095670; 20170095721; 20170100064; 20170105622; 20170109829; 20170112379; 20170112422; 20170112447; 20170112671; 20170113641; 20170113702; 20170118551; 20170119255; 20170120052; 20170120107; 20170124110; 20170124276; 20170127957; 20170131163; 20170133873; 20170136264; 20170136265; 20170140482; 20170142023; 20170142113; 20170156635; 20170156662; 20170164876; 20170164878; 20170168566; 20170172424; 20170172463; 20170172470; 20170177025; 20170181711; 20170185731; 20170185743; 20170185745; 20170188872; 20170189751; 20170193395; 20170199979; 20170200296; 20170200898; 20170205221; 20170206721; 20170209095; 20170214963; 20170215742; 20170215745; 20170216671; 20170216672; 20170216673; and 20170220772.

Ahmad, R., N. Griffete, A. Lamouri, N. Felidj, M. M. Chehimi, C. Mangeney, Chem. Mater. 2015, 27, 5464.

Albrecht, K., Y. Hirabayashi, M. Otake, S. Mendori, Y. Tobari, Y. Azuma, Y. Majima, K. Yamamoto, Sci. Adv. 2016, 2, e1601414.

Al-Omari, M.; Sel, K.; Mueller, A.; Edwards, J.; Kaya, T. Detection of relative [Na+] and [K+] levels in sweat with optical measurements. J. Appl. Phys. 2014, 115, 203107.

Astruc, D., Nat. Chem. 2012, 4, 255.

Bandodkar, A. J.; Hung, V. W.; Jia, W.; Valdés-Ramírez, G.; Windmiller, J. R.; Martinez, A. G.; Ramírez, J.; Chan, G.; Kerman, K.; Wang, J. Tattoo-based potentiometric ion-selective sensors for epidermal pH monitoring. Analyst 2013, 138, 123-128.

Bandodkar, A. J.; Molinnus, D.; Mirza, O.; Guinovart, T.; Windmiller, J. R.; Valdés-Ramírez, G.; Andrade, F. J.; Schöning, M. J.; Wang, J. Epidermal tattoo potentiometric sodium sensors with wireless signal transduction for continuous non-invasive sweat monitoring. Biosens. Bioelectron. 2014, 54, 603-609.

Brust, M.; Walker, M.; Bethell, D.; Schiffrin, D. J.; Whyman, R. Synthesis of thiol-derivatised gold nanoparticles in a two-phase liquid-liquid system. J. Chem. Soc., Chem. Commun. 1994, 7, 801-802.

Caminade, A. M., S. Fruchon, C. O. Turrin, M. Poupot, A. Ouali, A. Maraval, M. Garzoni, M. Maly, V. Furer, V. Kovalenko, J. P. Majoral, G. M. Pavan, R. Poupot, Nat. Commun. 2015, 6, 7722.

Cerda, B. A.; Wesdemiotis, C. Li+, Na+, and K+ binding to the DNA and RNA nucleobases. Bond energies and attachment sites from the dissociation of metal ion-bound heterodimers. J. Am. Chem. Soc. 1996, 118, 11884-11892.

Chaga, G. S. Twenty-five years of immobilized metal ion affinity chromatography: past, present and future. J. Biochem. Biophys. Methods 2001, 49, 313-334.

Chami Khazraji, A., S. Robert, J. Nanomater. 2013, 2013, 1.

Chang, B. W.; Yeh, S. J.; Tsai, P. P.; Chang, H. C. Monitoring perspiration from palms of hypohidrosis patients with a stopped-flow conductometric mini-system. Clin. Chim. Acta 2004, 348, 107-111.

Cheung, R. C. F.; Wong, J. H.; Ng, T. B. Immobilized metal ion affinity chromatography: a review on its applications. Appl. Microbiol. Biotechnol. 2012, 96, 1411-1420.

Corrie, S. R.; Coffey, J. W.; Islam, J.; Markey, K. A.; Kendall, M. A. F. Blood, sweat, and tears: developing clinically relevant protein biosensors for integrated body fluid analysis. Analyst 2015, 140, 4350-4364.

Curto, V. F.; Coyle, S.; Byrne, R.; Angelov, N.; Diamond, D.; Benito-Lopez, F. Concept and development of an autonomous wearable micro-fluidic platform for real time pH sweat analysis. Sens. Actuators, B 2012, 175, 263-270.

Curto, V. F.; Fay, C.; Coyle, S.; Byrne, R.; O'Toole, C.; Barry, C.; Hughes, S.; Moyna, N.; Diamond, D.; Benito-Lopez, F. Real-time sweat pH monitoring based on a wearable chemical barcode micro-fluidic platform incorporating ionic liquids. Sens. Actuators, B 2012, 171, 1327-1334.

Edel, J. B., A. A. Kornyshev, A. R. Kucernak, M. Urbakh, Chem. Soc. Rev. 2016, 45, 1581.

Eisenach, J. H.; Atkinson, J. L. D.; Fealey, R. D. Hyperhidrosis: Evolving Therapies for a Well-Established Phenomenon. Mayo Clin. Proc. 2005, 80, 657-666.

Gaberc-Porekar, V.; Menart, V. Perspectives of immobilized-metal affinity chromatography. J. Biochem. Biophys. Methods 2001, 49, 335-360.

Gao, W.; Emaminejad, S.; Nyein, H. Y.; Challa, S.; Chen, K.; Peck, A.; Fahad, H. M.; Ota, H.; Shiraki, H.; Kiriya, D.;

Lien, D. H.; Brooks, G. A.; Davis, R. W.; Javey, A. Fully integrated wearable sensor arrays for multiplexed in situ perspiration analysis. Nature 2016, 529, 509-514.

Ghosh, A., A. Maity, R. Banerjee, S. B. Majumder, J. Alloys Compd. 2017, 692, 108.

Gong, S., W. Schwalb, Y. Wang, Y. Chen, Y. Tang, J. Si, B. Shirinzadeh, W. Cheng, Nat. Commun. 2014, 5, 4132.

Güder, F., A. Ainla, J. Redston, B. Mosadegh, A. Glavan, T. Martin, G. M. Whitesides, Angew. Chem. 2016, 128, 5821.

Guinovart, T.; Bandodkar, A. J.; Windmiller, J. R.; Andrade, F. J.; Wang, J. A potentiometric tattoo sensor for monitoring ammonium in sweat. Analyst 2013, 138, 7031-7038.

Han, L.; Luo, J.; Kariuki, N. N.; Maye, M. M.; Jones, V. W.; Zhong, C. J. Novel interparticle spatial properties of hydrogen-bonding mediated nanoparticle assembly. Chem. Mater. 2003, 15, 29-37.

Hasanzadeh, M., N. Shadjou, M. Eskandani, J. Soleymani, F. Jafari, M. de la Guardia, Trends Anal. Chem. 2014, 53, 137.

Hohenester, U., A. Trügler, Comput. Phys. Commun. 2012, 183, 370. [42] Z. Skeete, H. W. Cheng, Q. M. Ngo, C. Salazar, W. Sun, J. Luo, C. J. Zhong, Nanotechnology 2016, 27, 325706.

Hostetler, M. J.; Wingate, J. E.; Zhong, C. J.; Harris, J. E.; Vachet, R. W.; Clark, M. R.; Londono, J. D.; Green, S. J.; Stokes, J. J.; Wignall, G. D.; Glish, G. L.; et al. Alkanethiolate gold cluster molecules with core diameters from 1.5 to 5.2 nm: core and monolayer properties as a function of core size. Langmuir 1998, 14, 17-30.

Ibanez, F. J., F. P. Zamborini, Small 2012, 8, 174.

Imani, S., A. J. Bandodkar, A. M. Mohan, R. Kumar, S. Yu, J. Wang, P. P. Mercier, Nat. Commun. 2016, 7, 11650.

Indo, Y.; Tsuruta, M.; Hayashida, Y.; Karim, M. A.; Ohta, K.; Kawano, T.; Mitsubuchi, H.; Tonoki, H.; Awaya, Y.; Matsuda, I. Mutations in the TRKA/NGF receptor gene in patients with congenital insensitivity to pain with anhidrosis. Nat. Genet. 1996, 13, 485-488.

Jishkariani, D., B. T. Diroll, M. Cargnello, D. R. Klein, L. A. Hough, C. B. Murray, B. Donnio, J. Am. Chem. Soc. 2015, 137, 10728.

Kaga, S., M. Arslan, R. Sanyal, A. Sanyal, Molecules 2016, 21, 497.

Kang, N., F. Lin, W. Zhao, J. P. Lombardi, M. Almihdhar, K. Liu, S. Yan, J. Kim, J. Luo, B. S. Hsiao, C. J. Zhong, ACS Sens. 2016, 1, 1060.

Khodagholy, D.; Curto, V. F.; Fraser, K. J.; Gurfinkel, M.; Byrne, R.; Diamond, D.; Malliaras, G. G.; Benito-Lopez, F.; Owens, R. M. Organic electrochemical transistor incorporating an ionogel as a solid state electrolyte for lactate sensing. J. Mater. Chem. 2012, 22, 4440-4443.

Kim, J. S., H. W. Yoo, H. O. Choi, H. T. Jung, Nano Lett. 2014, 14, 5941.

Kim, J.; de Araujo, W. R.; Samek, I. A.; Bandodkar, A. J.; Jia, W.; Brunetti, B.; Paixão, T. R.; Wang, J. Wearable temporary tattoo sensor for real-time trace metal monitoring in human sweat. Electrochem. Commun. 2015, 51, 41-45.

Koh, A., D. Kang, Y. Xue, S. Lee, R. M. Pielak, J. Kim, T. Hwang, S. Min, A. Banks, P. Bastien, Sci. Transl. Med. 2016, 8, 366ra165.

Krasteva, N., Y. Fogel, R. E. Bauer, K. Müllen, Y. Joseph, N. Matsuzawa, A. Yasuda, T. Vossmeyer, Adv. Funct. Mater. 2007, 17, 881.

Lao, L. M.; Kumakiri, M.; Mima, H.; Kuwahara, H.; Ishida, H.; Ishiguro, K.; Fujita, T.; Ueda, K. The ultrastructural characteristics of eccrine sweat glands in a Fabry disease patient with hypohidrosis. J. Dermatol. Sci. 1998, 18, 109-117.

Lee, H., T. K. Choi, Y. B. Lee, H. R. Cho, R. Ghaffari, L. Wang, H. J. Choi, T. D. Chung, N. Lu, T. Hyeon, S. H. Choi, D. H. Kim, Nat. Nanotechnol. 2016, 11, 566.

Lee, J.; Pyo, M.; Lee, S. H.; Kim, J.; Ra, M.; Kim, W. Y.; Park, B. J.; Lee, C. W.; Kim, J. M. Hydrochromic conjugated polymers for human sweat pore mapping. Nat. Commun. 2014, 5, 1-10.

Lee, S. H.; Rasaiah, J. C. Molecular dynamics simulation of ionic mobility. I. Alkali metal cations in water at 25° C. J. Chem. Phys. 1994, 101, 6964-6974.

Lim, I. I. S., C. Vaiana, Z. Y. Zhang, Y. J. Zhang, D. L. An, C. J. Zhong, J. Am. Chem. Soc. 2007, 129, 5368.

Ma, H., K. Yoon, L. Rong, Y. Mao, Z. Mo, D. Fang, Z. Hollander, J. Gaiteri, B. S. Hsiao, B. Chu, J. Mater. Chem. 2010, 20, 4692.

Ma, H.; Burger, C.; Hsiao, B. S.; Chu, B. Ultrafine polysaccharide nanofibrous membranes for water purification. Biomacromolecules 2011, 12, 970-976.

Ma, H.; Hsiao, B. S.; Chu, B. Thin-film nanofibrous composite membranes containing cellulose or chitin barrier layers fabricated by ionic liquids. Polymer 2011, 52, 2594-2599.

Mahfouz, M. R.; Kuhn, M. J.; To, G. Wireless medical devices: A review of current research and commercial systems. In Biomedical Wireless Technologies, Networks, and Sensing Systems (BioWireleSS); IEEE Topical Conference; IEEE: New York, 2013, pp 16-18.10.1109/Bio-WireleSS.2013.6613660

Marino, T.; Russo, N.; Toscano, M. Interaction of Li+, Na+, and K+ with the proline amino acid. Complexation modes, potential energy profiles, and metal ion affinities. J. Phys. Chem. B 2003, 107, 2588-2594.

Matzeu, G.; Florea, L.; Diamond, D. Advances in wearable chemical sensor design for monitoring biological fluids. Sens. Actuators, B 2015, 211, 403-418.

Maye, M. M.; Zheng, W.; Leibowitz, F. L.; Ly, N. K.; Zhong, C. J. Heating-induced evolution of thiolate-encapsulated gold nano-particles: a strategy for size and shape manipulation. Langmuir 2000, 16, 490-497.

Morgan, R. M.; Patterson, M. J.; Nimmo, M. A. Acute effects of dehydration on sweat composition in men during prolonged exercise in the heat. Acta Physiol. Scand. 2004, 182, 37-43.

Mullen, D. G., M. Fang, A. Desai, J. R. Baker Jr., B. G. Orr, M. M. Banaszak Holl, ACS Nano 2010, 4, 657.

Nakhleh, M. K., H. Amal, R. Jeries, Y. Y. Broza, M. Aboud, A. Gharra, H. Ivgi, S. Khatib, S. Badarneh, L. Har-Shai, L. Glass-Marmor, I. Lejbkowicz, A. Miller, S. Badarny, R. Winer, J. Finberg, S. Cohen-Kaminsky, F. Perros, D. Montani, B. Girerd, G. Garcia, G. Simonneau, F. Nakhoul, S. Baram, R. Salim, M. Hakim, M. Gruber, O. Ronen, T. Marshak, I. Doweck, O. Nativ, Z. Bahouth, D. Y. Shi, W. Zhang, Q. L. Hua, Y. Y. Pan, L. Tao, H. Liu, A. Karban, E. Koifman, T. Rainis, R. Skapars, A. Sivins, G. Ancans, I. Liepniece-Karele, I. Kikuste, I. Lasina, I. Tolmanis, D. Johnson, S. Z. Millstone, J. Fulton, J. W. Wells, L. H. Wilf, M. Humbert, M. Leja, N. Peled, H. Haick, ACS Nano 2016, 11, 112.

Njoki, P. N.; Lim, I. I. S.; Mott, D.; Park, H. Y.; Khan, B.; Mishra, S.; Sujakumar, R.; Luo, J.; Zhong, C. J. Size correlation of optical and spectroscopic properties for gold nanoparticles. J. Phys. Chem. C 2007, 111, 14664-14669.

Oh, J. Y., S. Rondeau-Gagne, Y. C. Chiu, A. Chortos, F. Lissel, G. N. Wang, B. C. Schroeder, T. Kurosawa, J. Lopez, T. Katsumata, J. Xu, C. Zhu, X. Gu, W. G. Bae, Y. Kim, L. Jin, J. W. Chung, J. B. Tok, Z. Bao, Nature 2016, 539, 411.

Olichwer, N., A. Meyer, M. Yesilmen, T. Vossmeyer, J. Mater. Chem. C 2016, 4, 8214.

Parat, A., C. Bordeianu, H. Dib, A. Garofalo, A. Walter, S. Begin-Colin, D. Felder-Flesch, Nanomedicine 2015, 10, 977.

Remko, M.; Rode, B. M. Effect of metal ions (Li+, Na+, K+, Mg2+, Ca2+, Ni2+, Cu2+, and Zn2+) and water coordination on the structure of glycine and zwitterionic glycine. J. Phys. Chem. A 2006, 110, 1960-1967.

Schazmann, B.; Morris, D.; Slater, C.; Beirne, S.; Fay, C.; Reuveny, R.; Moyna, N.; Diamond, D. A wearable electrochemical sensor for the real-time measurement of sweat sodium concentration. Anal. Methods 2010, 2, 342-348.

Schittek, B.; Hipfel, R.; Sauer, B.; Bauer, J.; Kalbacher, H.; Stevanovic, S.; Schirle, M.; Schroeder, K.; Blin, N.; Meier, F.; Rassner, G.; Garbe, C. Dermcidin: a novel human antibiotic peptide secreted by sweat glands. Nat. Immunol. 2001, 2, 1133-1137.

Schulz, F., T. Vossmeyer, N. G. Bastus, H. Weller, Langmuir 2013, 29, 9897.

Segev-Bar, M., N. Bachar, Y. Wolf, B. Ukrainsky, L. Sarraf, H. Haick, Adv. Funct. Mater. 2017, 2, 1600206.

Shan, S.; Zhao, W.; Luo, J.; Yin, J.; Switzer, J. C.; Joseph, P.; Lu, S.; Poliks, M.; Zhong, C. J. Flexibility characteristics of a polyethylene terephthalate chemiresistor coated with a nanoparticle thin film assembly. J. Mater. Chem. C 2014, 2, 1893-1903.

Sonner, Z.; Wilder, E.; Heikenfeld, J.; Kasting, G.; Beyette, F.; Swaile, D.; Sherman, F.; Joyce, J.; Hagen, J.; Kelley-Loughnane, N.; Naik, R. The microfluidics of the eccrine sweat gland, including biomarker partitioning, transport, and biosensing implications. Biomicrofluidics 2015, 9, 031301.

Srivastava, S., B. L. Frankamp, V. M. Rotello, Chem. Mater. 2005, 17, 487.

Teesch, L. M.; Adams, J. Fragmentations of gas-phase complexes between alkali metal ions and peptides: metal ion binding to carbonyl oxygens and other neutral functional groups. J. Am. Chem. Soc. 1991, 113, 812-820.

Vaks, V. L., E. G. Domracheva, E. A. Sobakinskaya, M. B. Chernyaeva, Phys.-Usp. 2014, 57, 684.

Wang, L., D. J. Kiemle, C. J. Boyle, E. L. Connors, I. Gitsov, Macromolecules 2014, 47, 2199.

Wang, L., J. Luo, J. Yin, H. Zhang, J. Wu, X. Shi, E. Crew, Z. Xu, Q. Rendeng, S. Lu, C. J. Zhong, J. Mater. Chem. 2010, 20, 907.

Wang, L., L. Wang, X. Shi, N. N. Kariuki, M. Schadt, G. R. Wang, Q. Rendeng, J. Choi, J. Luo, S. Lu, C. J. Zhong, J. Am. Chem. Soc. 2007, 129, 2161.

Wang, X., Z. Liu, T. Zhang, Small 2017, 13, 1602790.

Wang, X.; Fang, D.; Hsiao, B. S.; Chu, B. Nanofiltration membranes based on thin-film nanofibrous composites. J. Membr. Sci. 2014, 469, 188-197.

Yin, J., P. Hu, J. Luo, L. Wang, M. F. Cohen, C. J. Zhong, ACS Nano 2011, 5, 6516.

Zhao, W., T. Rovere, D. Weerawarne, G. Osterhoudt, N. Kang, P. Joseph, J. Luo, B. Shim, M. Poliks, C. J. Zhong, ACS Nano 2015, 9, 6168.

Zhao, W.; Al-Nasser, L. F.; Shan, S.; Li, J.; Skeete, Z.; Kang, N.; Luo, J.; Lu, S.; Zhong, C. J.; Grausgruber, C. J.; Harris, R. Detection of mixed volatile organic compounds and lung cancer breaths using chemiresistor arrays with crosslinked nanoparticle thin films. Sens. Actuators, B 2016, 232, 292-299.

Zhao, W.; Luo, J.; Shan, S.; Lombardi, J. P.; Xu, Y.; Cartwright, K.; Lu, S.; Poliks, M.; Zhong, C. J. Sensors: Nanoparticle-Structured Highly Sensitive and Anisotropic Gauge Sensors. Small 2015, 11, 4508-4508.

Zhao, W.; Rovere, T.; Weerawarne, D.; Osterhoudt, G.; Kang, N.; Joseph, P.; Luo, J.; Shim, B.; Poliks, M.; Zhong, C. J. Nanoalloy Printed and Pulse-Laser Sintered Flexible Sensor Devices with Enhanced Stability and Materials Compatibility. ACS Nano 2015, 9, 6168-6177.

What is claimed is:

1. A sensor, comprising:
   a sensing medium, comprising a plurality of fibers within a fibrous layer, and a plurality of metallic nanoparticles coating the plurality of fibers within the fibrous layer, the plurality of metallic nanoparticles being derivatized to reversibly interact with the fibrous layer and a chemical analyte, based on at least one of electronic charge, ligand coordination, hydrogen bonding, van der Waals force, polarity, hydrophilicity, and hydrophobicity; and
   an electrode, configured to sense a change in a state of the sensing medium over time responsive to the chemical analyte, and to produce an electrical signal output corresponding to the change in the state.

2. The sensor according to claim 1, wherein the plurality of fibers within the fibrous layer comprise nanofibers.

3. The sensor according to claim 1, wherein the plurality of fibers within the fibrous layer comprise nanofibrous cellulose.

4. The sensor according to claim 1, wherein the plurality of fibers comprise a plurality of nanofibers, and the plurality of metallic nanoparticles are derivatized with an alkanethiolate shell.

5. The sensor according to claim 1, wherein the fibrous layer comprises a natural cellulose fiber paper.

6. The sensor according to claim 1, wherein the plurality of metallic nanoparticles are gold nanoparticles.

7. The sensor according to claim 1, wherein the plurality of metallic nanoparticles are derivatized to be electronically charged.

8. The sensor according to claim 1, further comprising a permeable electrospun fiber layer supporting the fibrous layer.

9. The sensor according to claim 1, further comprising a permeable layer formed of fibers having a first diameter, and a non-woven fiber layer formed of fibers having a second diameter, the permeable layer being supported on the non-woven fiber layer, and the fibrous layer being formed of fibers having a third diameter and being supported on the permeable layer,
   wherein the second diameter is larger than the first diameter, and the first diameter larger than the third diameter.

10. The sensor according to claim 1, further comprising:
   a permeable layer comprising at least one polymer selected from the group consisting of crosslinked polyacrylonitrile (PAN) and crosslinked polyethylene glycol diacrylate (PEGDA); and
   a polyethylene terephthalate (PET) non-woven layer,
   the permeable layer being supported on the polyethylene terephthalate (PET) non-woven layer, and the fibrous layer being supported on the permeable layer.

11. The sensor according to claim 1,
wherein the fibrous layer consists essentially of fibers having a fiber diameter of between 1 nm and 15 nm,
the fibrous layer being supported on a fibrous intervening layer comprising fibers having a fiber diameter of between 50 nm and 250 nm, and
the fibrous intervening layer is disposed on a flexible support layer.

12. The sensor according to claim 1, wherein the plurality of metallic nanoparticles are at least one of:
linked to a thiolate through a thiol bond;
linked to 11-mercaptoundecanoic acid (MUA) within the fibrous layer through a hydrogen bond;
linked to a carboxylic acid; and
electrostatically bound to poly(diallyl ammonium) within the fibrous layer.

13. The sensor according to claim 1, wherein the fibrous layer is cast from a slurry of nanofibers on an electrospun layer.

14. The sensor according to claim 1, wherein the electrical signal output is selectively responsive to a concentration of at least one of moisture and ions of the chemical analyte.

15. The sensor according to claim 1, wherein the electrode comprises a pair of spaced interdigitated conductive traces separated by a gap, configured to sense a change in at least one of a conductivity and a capacitance of the fibrous layer, further comprising an electronic circuit configured to receive the electrical signal output, and to determine a quantitative parameter of the chemical analyte.

16. The sensor according to claim 1, wherein the electrical signal output has a monotonically increasing electrical response to a concentration of an ionic species within the chemical analyte over a range from 0 to 100 mM.

17. A method of sensing chemical analyte, comprising:
providing a sensor, the sensor comprising:
a sensing medium comprising a fibrous layer and a plurality of derivatized conductive nanoparticles, the plurality of derivatized conductive nanoparticles coating fibers within the fibrous layer, and the derivatized conductive nanoparticles being derivatized to reversibly interact with the fibrous layer to alter an electrical state of the sensing medium in response to the chemical analyte, based on at least one of an electronic charge, hydrogen bonding, van der Waals force, polarity, hydrophilicity, and hydrophobicity of the derivatized conductive nanoparticles; and
an electrode for sensing a change in the electrical state of the sensing medium and producing as an output an electrical signal corresponding to the sensed change in electrical state;
exposing the sensor to the chemical analyte; and
producing the output, representing the sensed electrical state of the sensing medium dependent on the reversible interaction between the chemical analyte and the derivatized conductive nanoparticles.

18. The method according to claim 17, wherein the fibers of the fibrous layer have a nanofiber diameter of between 1 nm and 15 nm, and have exposed groups capable of at least one of ionic bonding, hydrogen bonding, and van der Waals interaction with the derivatized conductive nanoparticles, and the derivatized conductive nanoparticles comprise gold nanoparticles having a diameter between 2 and 70 nm, derivatized to have at least one sulfur linkage.

19. A sensor, comprising:
a sensing medium, comprising a mat of nanofibers coated with derivatized conductive metallic nanoparticles, wherein the derivatized conductive metallic nanoparticles reversibly interact with the mat of fibers and a chemical analyte, based on at least one of electronic charge, ligand coordination, hydrogen bonding, van der Waals force, polarity, hydrophilicity, and hydrophobicity, to have an electrical impedance responsive to a concentration of the chemical analyte; and
an electrode, configured to sense a change in the electrical impedance of the sensing medium in response to a change in the concentration of the chemical analyte, and to conduct an electrical signal output in dependence on the electrical impedance,
wherein the nanofibers comprise organic nanofibers having a nanofiber diameter of between 1 nm and 100 nm, and the derivatized conductive metallic nanoparticles having a nanoparticle diameter of between 1 nm and 200 nm.

20. The sensor according to claim 19, wherein:
the derivatized conductive metallic nanoparticles comprise gold nanoparticles having a diameter between 2 and 70 nm, derivatized to have sulfur linkages; and
the nanofibers comprise cellulose nanofibers,
wherein the chemical analyte is human sweat, and the sensor has an impedance which varies selectively responsive to a presence of the human sweat.

* * * * *